(12) United States Patent
Seefeldt et al.

(10) Patent No.: US 7,829,681 B2
(45) Date of Patent: Nov. 9, 2010

(54) HIGH-PRESSURE INCLUSION BODY SOLUBILIZATION AND PROTEASE CLIPPING OF RECOMBINANT FUSION PROTEINS

(75) Inventors: Matthew B. Seefeldt, Boulder, CO (US); Lyndal K. Hesterberg, Boulder, CO (US); Theodore W. Randolph, Niwot, CO (US); John F. Carpenter, Littleton, CO (US)

(73) Assignee: Barofold Inc., Aurora, CO (US)

( * ) Notice: Subject to any disclaimer, the term of this patent is extended or adjusted under 35 U.S.C. 154(b) by 51 days.

(21) Appl. No.: 12/098,877

(22) Filed: Apr. 7, 2008

(65) Prior Publication Data

US 2008/0248522 A1 Oct. 9, 2008

Related U.S. Application Data

(60) Provisional application No. 60/922,250, filed on Apr. 5, 2007.

(51) Int. Cl.
*C07K 14/00* (2006.01)
*C12N 9/48* (2006.01)
*C12P 21/04* (2006.01)

(52) U.S. Cl. .................. 530/427; 435/212; 435/69.7

(58) Field of Classification Search ................. None
See application file for complete search history.

(56) References Cited

U.S. PATENT DOCUMENTS 6,489,450 B2 * 12/2002 Randolph et al. ........... 530/427

OTHER PUBLICATIONS

Seefeldt et al. 2009, Application of High Hydrostatic Pressure to Dissociate Aggregates and Refold Protein, Current Pharmaceutical Biotechnology, 2009, vol. 10, pp. 447-555.*
Shoner et al. Reconstitution of functional nuclear receptor proteins using high pressure refolding. Molecular Genetics and Metabolism, 2005, vol. 85, pp. 318-322.*

* cited by examiner

*Primary Examiner*—Suzanne M. Noakes
(74) *Attorney, Agent, or Firm*—Cooley LLP

(57) ABSTRACT

Described herein are methods for the solubilization and proteolytic cleavage of fusion protein aggregates, including autocatalytic fusion proteins, at pressures greater than atmospheric pressure to yield soluble target polypeptides.

24 Claims, 10 Drawing Sheets

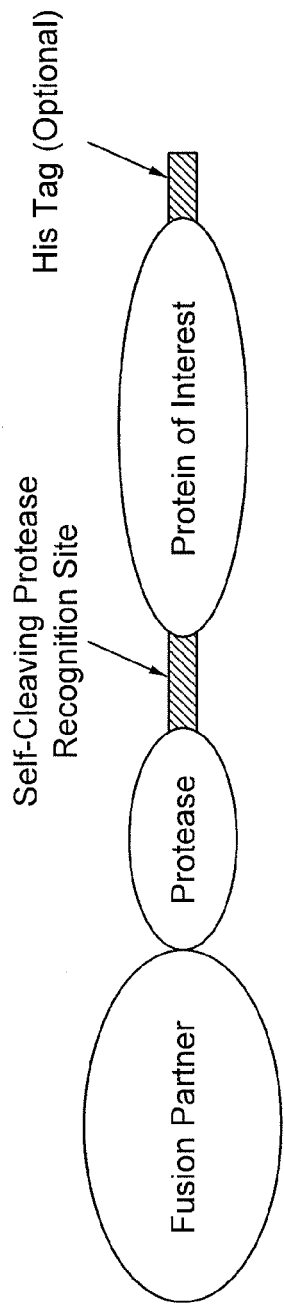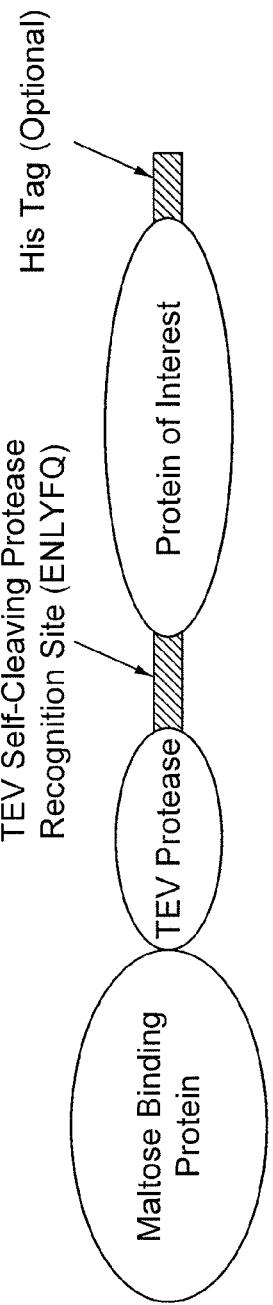

HIGH-PRESSURE INCLUSION BODY SOLUBILIZATION AND PROTEASE CLIPPING OF RECOMBINANT FUSION PROTEINS

CROSS REFERENCE TO RELATED APPLICATIONS

This application claims priority benefit of U.S. Provisional Patent Application No. 60/922,250, filed Apr. 5, 2007. The content of that application is hereby incorporated by reference herein in its entirety.

BACKGROUND OF THE INVENTION

Therapeutic proteins provide enormous potential for the treatment of human disease. Dozens of protein therapeutics are currently available, with hundreds more in clinical development (PhRMA 2004). Such proteins include human growth hormone, which is used to treat abnormal height when insufficient growth hormone is produced in the body, and interferon-gamma, which is used to treat neoplastic and viral diseases. Protein pharmaceuticals are often produced using recombinant DNA technology, which can enable production of higher amounts of protein than can be isolated from naturally-occurring sources, and which avoids contamination that often occurs with proteins isolated from naturally-occurring sources. Unfortunately, protein aggregation is a common problem that arises during all phases of recombinant protein production, specifically during fermentation, purification, and long term storage (Baneyx 1999; Carpenter et al. 1997; Chi et al. 2003; Clark 2001; Schwarz et al. 1996).

Proper folding of a protein is essential to the normal functioning of the protein. Improperly folded proteins are believed to contribute to the pathology of several diseases, including Alzheimer's disease, bovine spongiform encephalopathy (BSE, or "mad cow" disease) and human Creutzfeldt-Jakob disease (CJD), and Parkinson's disease; these diseases serve to illustrate the importance of proper protein folding.

Several proteins of therapeutic value in humans, such as recombinant human growth hormone and recombinant human interferon gamma, can be expressed in bacteria, yeast, and other microorganisms. While large amounts of proteins can be produced in such systems, the proteins are often misfolded, and often aggregate together in large clumps called inclusion bodies. The proteins cannot be used in the misfolded, aggregated state. Accordingly, methods of disaggregating and properly refolding such proteins have been the subject of much investigation.

One method of refolding proteins uses high pressure on solutions of proteins in order to disaggregate, unfold, and properly refold proteins. Such methods are described in U.S. Pat. Nos. 6,489,450, 7,064,192, U.S. Patent Application Publication No. 2004/0038333, and International Patent Application WO 02/062827. Those disclosures indicated that certain high-pressure treatments of aggregated proteins or misfolded proteins resulting in recovery of disaggregated protein retaining biological activity (i.e., the protein was properly folded, as is required for biological activity) in good yields. U.S. Pat. No. 6,489,450, U.S. 2004/0038333, and WO 02/062827 are incorporated by reference herein in their entireties. Additional studies (see U.S. Pat. App. Pub. No. 2005/0020818, Randolph et al. 2002; Seefeldt et al. 2004; St. John et al. 1999; St. John et al. 2002) have also shown that high hydrostatic pressure (c. a. 2000 bar) can be an effective refolding tool, enabling refolding at relatively high concentration and with high yield. In contrast to traditional chaotrope-based refolding, pressures can be selected that dissociate aggregates under conditions that favor the protein's native conformation (Seefeldt et al. 2004; St. John et al. 2002). High pressure refolding has been particularly effective when the aggregates contain non-native disulfide bonds, providing sufficient time for disulfide bond formation while inhibiting off-pathway aggregation reactions (Seefeldt et al. 2004; St. John et al. 2002).

High hydrostatic pressures (up to 4000 bar) have been shown to increase the catalytic activity of twelve enzymes and proteases (Hendrickx et al. 1998; Mozhaev et al. 1996). Although the mechanism remains unclear, it appears the high hydrostatic pressures increase reaction kinetics through enzymatic reactions that have negative activation volumes, while favoring or even stabilizing the native enzyme conformation (Mozhaev et al. 1996). Some proteases have also been found to be unusually stable at elevated pressures, which may be due to their low partial specific volume (Gekko 2002; Gekko and Hasegawa 1986; Seefeldt et al. 2003). These studies conclude that high hydrostatic pressures (c.a. 2000) maintain or, in some cases, increase activity of certain enzymes, although there is an upper limit and higher pressures can also inactivate enzymes through denationuration (Hendrickx et al. 1998; Mozhaev et al. 1996; Royer 2002).

For some proteins, prokaryotic expression in *E. coli*. is further complicated by the need for co-expression with fusion partners as a so-called fusion protein. Fusion proteins are often required to minimize the lethality of expressed proteins or improve solubility (Baneyx 1999; Sorensen and Mortensen 2005). For example, therapeutic recombinant human insulin and recombinant human insulin-like growth factor can also modulate bacterial cellular processes. These properties necessitate the use of fusion proteins and co-expression for industrial scale production. Fusion proteins facilitate prokaryotic expression, however they must be removed for final drug production (Baneyx 1999; Sorensen and Mortensen 2005).

Currently, the main disadvantages of fusion-protein technologies are: First, liberation of the passenger proteins requires expensive protease (e.g. Factor Xa and enterokinase). Secondly, cleavage is rarely complete, leading to reduction in yields. Thirdly, additional processing steps may be required to obtain an active product (Baneyx 1999; Sorensen and Mortensen 2005). Traditionally, chaotropes are required to facilitate solubilization, but also denature native proteins, decreasing protease stability and effectiveness (Timasheff 1993).

Thus there is a need for improved processes for efficiently and cost-effectively solubilizing and cleaving fusion protein aggregates to produce useful recombinant proteins for use in therapeutic and industrial settings. The methods provided herein use high hydrostatic pressure to solubilize fusion protein aggregates produced during prokaryotic expression and cleave the fusion protein efficiently with minimal manipulation of the fusion protein aggregates and resulting protein of interest. If protease cleavage can occur in the presence of disulfide shuffling agents or the protein of interest does not contain disulfide bonds, refolding can also occur during solubilization and cleavage process, thus providing a highly efficient and cost-effective single step method for solubilization/cleavage/refolding.

BRIEF SUMMARY OF THE INVENTION

Provided herein are methods for solubilizing and proteolytically cleaving mixtures containing fusion protein aggregates and/or fusion protein monomers at increased pressure (greater than atmospheric pressure) to yield soluble target polypeptides.

In one aspect of the invention are provided methods for producing soluble target polypeptide in samples comprising fusion protein aggregates comprising the steps of:

a) subjecting a mixture comprising an aqueous solution and/or aqueous suspension comprising protease and fusion protein aggregates and/or fusion protein monomers to increased hydrostatic pressure compared to atmospheric pressure for a time sufficient for formation of soluble target polypeptide; and, b) decreasing the pressure to atmospheric pressure, wherein a portion of the target polypeptide is soluble at atmospheric pressure.

In some variations of the methods, the target polypeptide is biologically active at atmospheric pressure. In other variations, the target polypeptide is not biologically active at atmospheric pressure.

In some embodiments of the methods, the target polypeptide is produced by specific proteolytic cleavage of a fusion partner from the fusion protein. In certain variations, the fusion protein is disaggregated in step (a).

In some variations of the methods, prior to step (a), the samples are subject to purification. In certain embodiments, purification includes sedimentation.

In some embodiments, the methods include a further step (c) comprising purifying the target polypeptide obtained in step (b). In some variations, purifying includes affinity chromatography, HPLC, dialysis, solution exchange, ion exchange chromatography, size exclusion chromatography, reverse-phase chromatography, ammonium sulfate precipitation, or electrophoresis.

In certain variations, in step (a), the increased hydrostatic pressure is from about 500 to about 10000 bar. In some variations, the increased hydrostatic pressure is from about 1500 to about 4000 bar. In particular variations, the increased hydrostatic pressure is about 2000 bar.

In some embodiments, step (b) comprises stepwise pressure reductions.

In certain variations, during at least one pressure reduction step the rate of pressure reduction is from about 5000 bar/4 days to about 5000 bar/sec.

In some variations, during at least one pressure reduction step the rate of pressure reduction is about 250 bar/5 minutes.

In certain variations there are at least 2 stepwise pressure reductions. In particular variations there are more than 2 stepwise pressure reductions.

In some variations, step (b) further comprises a hold period at constant pressure after at least one of the stepwise pressure reductions. In some embodiments, the hold period is from about 2 hours to about 50 hours. In certain embodiments, the hold period is about 6 hours.

In some embodiments, during the hold period the constant pressure is from about 500 bar to about 2000 bar. In certain variations, during the hold period the constant pressure is about 1000 bar.

In certain variations, during the hold period the constant pressure is about one-half of the pressure at which step (a) is performed. In some variations, during the hold period the constant pressure is about one-third of the pressure at which step (a) is performed.

In some embodiments, step (b) includes a continuous rate of pressure reduction. In some embodiments, the rate of pressure reduction is from about 5000 bar/1 sec to about 5000 bar/4 days. In certain embodiments, the rate of pressure reduction is 250 bar/5 minutes.

In certain variations the methods further include, after step (a) and prior to step (b) the steps of: a-1) adding one or more disulfide shuffling agent pairs to the mixture in an amount sufficient to facilitate formation of native disulfide bonds in the target polypeptide; and, a-2) subjecting the mixture to a further period of increased hydrostatic pressure compared to atmospheric pressure for a time sufficient for formation of native disulfide bonds in the target polypeptide.

In certain embodiments, prior to step (a-1), the increased hydrostatic pressure is reduced. In some of variations, the increased hydrostatic pressure is reduced to atmospheric pressure. In certain variations, prior to step (a-1), the increased hydrostatic pressure is maintained.

In some embodiments, the further period of increased hydrostatic pressure is at a pressure of from about 500 to about 3000 bar.

In certain embodiments, the further period of increased hydrostatic pressure is at a pressure of about two-thirds of the increased hydrostatic pressure in step (a).

In some variations, the further period of increased hydrostatic pressure is at a pressure of about one-half of the increased hydrostatic pressure in step (a).

In some variations the methods further include the step of reducing the amount of the disulfide shuffling agent pair present in the mixture after step (a).

In certain embodiments the methods further include the step of reducing the amount of the disulfide shuffling agent pair present in the mixture after step (a-2).

In some embodiments the methods further include performing solution exchange. In some variations, the solution exchange is performed after step (a). In certain embodiments, the solution exchange is performed during after a hold period during step (b).

In some embodiments the pH of the mixture is from about pH 4 to about pH 12. In certain embodiments, the pH of the mixture is from about pH 6 to about pH 8.5. In particular embodiments, pH of the mixture is from about pH 7 to about pH 8.5.

In some embodiments, step (a) is performed at a temperature from about 0° C. to about 100° C. In some variations, step (a) is performed at a temperature from about 0° C. to about 75° C.

In some embodiments, the mixture further includes a reducing agent. In some variations, the reducing agent is diothiothreitol, glutathione, dithioerythritol, tris(2-carboxyethyl)phosphine hydrochloride, or β-mercaptoethanol. In certain variations, the reducing agent is present in an amount sufficient to maintain activity of the protease. In some variations, the reducing agent is present in an amount sufficient to prevent the formation of non-native disulfide bonds in the target polypeptide.

In some embodiments, the method further includes addition of a target polypeptide ligand binding partner. In some variations, the ligand binding partner is selected from antibodies, receptors, peptides, peptidomimetics, vitamins, cofactors, prosthetic groups, substrates, products, competitive inhibitors, and metals. In some variations, the addition of the target polypeptide ligand binding partner is performed prior to, during or after step (a). In particular variations, the addition of the target polypeptide ligand binding partner is performed prior to step (a). In certain variations, the addition of the target polypeptide ligand binding partner is performed during or after step (b).

In some embodiments, the mixture further comprises a cleavage buffer.

In some embodiments, the cleavage buffer further comprises one or more additional agents is selected from one or more stabilizing agents, one or more buffering agents, one or more surfactants, one or more disulfide shuffling agent pairs, one or more chaotropic agents, one or more salts, and combinations of two or more of the foregoing.

In certain variations, the one or more additional agents is one or more stabilizing agents. In some embodiments, the one or more stabilizing agents is selected from one or more free amino acids, one or more preferentially excluding compounds, trimethylamine oxide, one or more cyclodextrans, one or more molecular chaperones, and combinations of two or more of the foregoing.

In some embodiments, the one or more stabilizing agents is one or more preferentially excluding compounds. In certain embodiments, the one or more one or more preferentially excluding compounds is one or more of: a sugar, glycerol, hexylene glycol, or combinations of two or more of the foregoing. In some embodiments, the one or more preferentially excluding compounds is one or more sugars. In certain embodiments, the one or more sugars is sucrose, trehalose, dextrose, mannose, or combinations of two or more of the foregoing. In some variations, the one or more sugars is present at a concentration of from about 0.1 mM to about the solubility limit of the sugar.

In some embodiments, wherein the one or more stabilizing agents is one or more free amino acids. In certain variations, the one or more free amino acids is arginine, lysine, proline, glutamine, glycine, histidine, or combinations of two or more of the foregoing. In some embodiments, the one or more free amino acids is present at a concentration of from about 0.1 mM to about the solubility limit of the free amino acid.

In some variations, the one or more stabilizing agents is a cyclodextran. In some embodiments, the cyclodextran is present at a concentration of from about 0.1 mM to about the solubility limit of the cyclodextran.

In some variations, the one or more stabilizing agents is a molecular chaperone. In certain variations the molecular chaperone is GroEs or GroEL. In some variations, the molecular chaperone is present at a concentration of from about 0.01 mg/ml to about 10 mg/ml.

In some embodiments, the one or more additional agents is one or more surfactants. In particular embodiments, the one or more surfactants is selected from polysorbates, polyoxyethylene ethers, alkyltrimethylammonium bromides, alkyltrimethyl ammonium chlorides, pyranosides and combinations of two or more of the foregoing. In some variations, the one or more surfactants is selected from polysorbate 80, polysorbate 20, Triton X-100, β-octyl-gluco-pyranoside, Brij 35, sarcosyl, octyl phenol ethoxylate, polyoxyethyleneglycol dodecyl ether, sodium dodecyl sulfate, polyethoxysorbitan, deoxycholate, sodium octyl sulfate, sodium tetradecyl sulfate, sodium cholate, octylthioglucopyranoside, n-octylglucopyranoside, octylphenoxypolyethoxy-ethanol, polyoxyethylene sorbitan, cetylpyridinium chloride, and sodium bis (2-ethylhexyl) sulfosuccinate.

In some variations, the one or more additional agents is one or more buffering agents. In certain variations, the one or more buffering agents is an organic buffer. In particular variations, the one or more buffering agents is an inorganic buffer. In some embodiments, the one or more buffering agents is selected from phosphate buffers, carbonate buffers, citrate, Tris, MOPS, MES, acetate, CHES, CAPS, and HEPES.

In some embodiments, the one or more additional agent is one or more chaotropic agents. In some variations, the one or more chaotropic agents is guanidine, guanidine sulfate, guanidine hydrochloride, urea, or thiocyanate. In some embodiments, the one or more chaotropic agents is urea in a concentration from about 0.1 mM to about 8 M. In certain embodiments, the one or more chaotropic agents is guanidine hydrochloride in a concentration of from about 0.1 mM to about 8 M. In some variations, the one or more chaotropic agents is at a concentration from about 0.01% (w/v) to about 10% (w/v).

In some variations, the one or more additional agents are one or more disulfide shuffling agent pair. In some embodiments, the disulfide shuffling agent pair include an oxidizing agent and a reducing agent. In some varations, the oxidizing agent is at least one of oxidized glutathione, cystine, cystamine, molecular oxygen, iodosobenzoic acid, sulfatalysis or a peroxide and the reducing agent is at least one of glutathione, cysteine, cysteamine, diothiothreitol, dithioerythritol, tris(2-carboxyethyl)phosphine hydrochloride, or β-mercaptoethanol. In certain variations, the disulfide shuffling agent pair is present at an oxidized concentration of from about 0.1 mM to about 100 mM oxidized thiol. In some variations, the concentration is from about 0.1 mM to about 10 mM. In certain variations, the concentration is from about 2 mM to about 6 mM.

In some variations, the time in step (a) is from about 15 minutes to about 50 hours. In some embodiments, the time is from about 6 hours to about 18 hours.

In some embodiments, the fusion partner is selected from his-tags, maltose-binding protein, thioredoxin, glutathione-s-transferase, DsbA (disulfide oxidoreductase), gphD (gamma head protein D), FLAG, calmodulin binding protein, streptag II, HA-tag, Softag1, Softag 3, c-myc, T7-tag, S-tag, NusA, chitin-binding domain, xylanase 10A, tobacco etch virus, and ubiquitin.

In some variations, the protease is a serine, cysteine or metalloprotease. In particular embodiments, the protease is a serine protease. In certain embodiments, the protease is a cysteine protease. In some variations, the cysteine protease is 3C protease.

In some embodiments, the molar ratio of protease to fusion protein is from about 1:1 to about 1:10000.

In some embodiments, the target polypeptide is a monomer.

In certain embodiments, the target polypeptide is a dimer. In particular embodiments, the dimer is a homodimer. In some variations, the dimer is a heterodimer.

In some embodiments, the target polypeptide is a trimer. In particular embodiments, the dimer is a homotrimer. In certain embodiments, the dimer is a heterotrimer.

In particular embodiments, the target polypeptide is a tetramer. In particular embodiments, the tetramer is a homotretramer. In some variations, the tetramer is a heterotetramer.

In some variations, the fusion protein comprises the protease. In some embodiments, the target polypeptide optionally includes an affinity tag.

In some variations, the total concentration of fusion protein in the fusion protein aggregate is from about 0.01 mg/mL to about 500 mg/mL. In some embodiments, the total concentration of fusion protein in the fusion protein aggregate is from about 0.01 mg/mL to about 250 mg/mL.

In certain embodiments where chaotropic agents are included, the methods further include the step of reducing the amount of the chaotropic agent present in the mixture after step (a).

In some embodiments, step (a) further includes agitation of the mixture.

In some variations, the method does not include one or more chaotropic agents.

In a further aspect are provided target polypeptides prepared by the methods described herein.

Unless specified otherwise or clearly dictated by the context, each of the methods described herein may be used in connection with the various fusion protein aggregates, fusion protein partners, target polypeptides and variations of the methods and conditions of the methods described herein.

BRIEF DESCRIPTION OF THE DRAWINGS

FIG. 8 depicts an embodiment useful for mixing solutions at high pressure.

FIG. 14A shows a schematic sequence for an autocatalytic fusion protein, with the fusion partner, autocatalytic protease, recognition (cleavage) site, target polypeptide, and optional affinity tag depicted, while FIG. 14B shows a schematic sequence of a maltose-binding protein/TEV protease autocatalytic fusion protein with optional affinity tag.

DETAILED DESCRIPTION OF THE INVENTION

Figure 1:
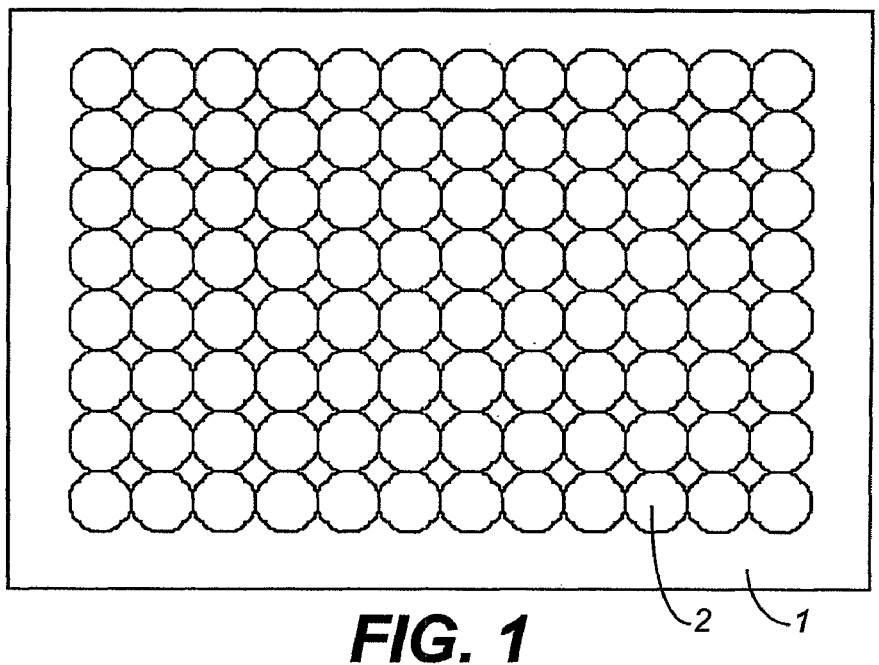
FIG. 1 depicts a top view of one embodiment of a multi-well plate design.

Recombinant polypeptides are increasingly used for many applications, from therapeutics to industrial processes and research. Many recombinant polypeptides are expressed as fusion proteins, which are often obtained in the form of inclusion bodies or other aggregated forms from the expression system. The inclusion bodies contain the target polypeptide of interest, as well as additional unwanted polypeptides. Contaminant polypeptides that are often present include the chaperones, such as GroEL (Buchner and Rudolph 1991). Additionally, comparison of reduced and non-reduced SDS-PAGE of inclusion bodies demonstrates the presence of some levels of non-native intermolecular disulfide bonds linking separate target polypeptide molecules (Buchner and Rudolph 1991). These aggregates often appear as bright spots under a phase contrast microscope. Data suggest that the secondary structure within the inclusion bodies can vary from native-like to non-native containing high levels intermolecular beta-sheet structures. Inclusion bodies of prochymosin and gamma interferon had dimensions of 1.26 and 0.8 µm respectively (Buchner and Rudolph 1991) The differences in inclusion body structure are further emphasized by the different susceptibility to guanidine denaturation or typsin protease cleavage as a function of the inclusion body location and growth conditions (Buchner and Rudolph 1991). Denaturant-based solubilization (including processes using chaotropes or other denaturants) and proteolytic cleavage of recombinant fusion proteins is an expensive multi-step process that requires significant resources, including large quantities of denaturant (e.g., chaotrope) as well as water, usually purified. After dilution of the denaturant to permit proteolytic cleavage, the yields are significantly less than 100% of the fusion protein content of the aggregate starting material and these yields are further reduced during the isolation and subsequent re-concentration of the target polypeptide. Such re-concentration of the target polypeptide can also lead to aggregation, which further decreases the overall yield and, especially for therapeutic products, must be removed from the preparation prior to use.

Fusion proteins are used to increase the expression, solubility, and purification capabilities of a recombinant target polypeptide (Amau et al. 2006; Baneyx 1999). For most applications, the fusion protein must be removed to eliminate any structural influences the fusion partner has on the target polypeptide and is especially applicable for protein structural studies and target polypeptides used as therapeutics. Typically, the fusion partner is separated from the target polypeptide by site specific proteolysis after affinity chromatography. Shih et al. report that "This step is considered to be the "Achilles heel" of the fusion protein approach" since cleavage is typically confounded by incomplete reactions (Shih et al. 2005). Consequently, there is a need to develop a protease/fusion partner system that is more effective (e.g., higher yields, etc.), efficient e.g., decreased production time, etc.), and less costly.

The current patent application describes generally the use of increased pressure in conjunction with fusion proteins and proteases (which may be included as part of the fusion protein) to prepare soluble target polypeptides. In this way, the fusion partner can be cleaved from the target polypeptide (e.g., protein of interest) while potentially preventing aggregation at elevated pressure, without necessitating the use of chaotropes or by using only very low concentrations of chaotropes. By implementing increased hydrostatic pressure with fusion cleavage, the skilled artisan has the advantage of conducting aggregate solubilization, cleavage, and refolding in fewer steps than traditional methods. For example, one processing step for aggregate solubilization, cleavage, and refolding where the target polypeptide does not contain disulfide bonds or where the protease is active in the presence of disulfide shuffling agent pairs. Additionally, increased pressure treatment minimizes detrimental reaggregation reactions that can occur due to the structural perturbations that arise from the use of a fusion partner.

In view of the challenges associated with the production of high purity recombinant target polypeptides in yields sufficient for commercial realization, it is apparent that new methods are needed for the solubilization and proteolytic cleavage of fusion protein aggregates and/or monomers (including misfolded and/or denatured monomers, etc.). Methods that reduce the quantities of reagents, and therefore the associated costs of purchasing reagents and disposing of waste materials, while providing improved yields of high purity target polypeptides in soluble and, in some cases, biologically active forms would be of great benefit.

As described in the Examples, particularly Examples 1 and 6, the cleavage protease (e.g., serine proteases, cysteine proteases (e.g., 3C protease, etc.), TEV, etc.) can be used in conjunction with the methods described herein to proteolytically cleave the fusion partner (e.g., ubiquitin, maltose binding protein, his-tag, etc.) from the target polypeptide. The kinetics of protease cleavage include the diffusion and steric limitations of the protease interacting with the cleavage site of the target polypeptide. For cleavage to occur, the protease needs to diffuse to the cleavage site, which also needs to be sterically available to enable proteolysis to occur. In the case of the systems described in Examples 1 and 5, as well other fusion proteins incorporating the proteases, fusion partners and target polypeptides described herein, this reaction should proceed in a commercially feasible time frame and high yield. However, it may also be advantageous to exploit an autocatalytic fusion partner that is effective at increased hydrostatic pressures. In these variations (e.g., such as described in Example 6), the methods would have the advantage of having a fusion partner cleavage reaction that would not be kinetically controlled by diffusion since the protease and cleavage site are both part of the fusion protein.

An exemplary protease for methods including autocatalytic fusion proteins is the tobacco etch virus (TEV) protease, which can be used as a self-cleaving fusion partner to enable autocatalytic cleavage of a fusion protein into fusion partner (in these variations the fusion partner can be a traditional fusion partner (e.g., maltose-binding protein, his-tags, etc.), protease and cleavage site, while the target polypeptide is co-expressed with the fusion partner to yield the fusion protein) at increased hydrostatic pressures (see FIGS. 14A and B). Autocatalytic proteolysis has been shown to be effective at atmospheric pressure by Shih et al. (Shih et al. 2005) (incorporated by reference herein in its entirety). As described in Example 6, the self-cleaving protease TEV is concomitantly expressed with the target polypeptide and thus decrease production costs (Shih et al. 2005). The development of an autocatalytic fusion protein would not be limited to the use of the TEV protease—other proteases can also be used, such as, but not limited to, Sortase A (Mao 2004) and Intein (Humphries et al. 2002). Additionally, different fusion partners can be incorporated. These include, but are not limited to, NusA, calmodulin binding protein (CBP), thioredoxin (Trx) (Tanaka et al. 2004), glutathione-S-tranferase (GST) (Smith and Johnson 1988), and $His_6$Tag (Chaga et al. 1999) (Shih et al. 2005) (the foregoing are incorporated by reference in their entirety).

"Denatured," as applied to a polypeptide in the present context, means that native secondary, tertiary, and/or quaternary structure is disrupted to an extent that the polypeptide does not have biological activity. In contrast to "denatured," the "native conformation" of a polypeptide refers to the secondary, tertiary and/or quaternary structures of a protein in its biologically active state.

"Refolding" in the present context means the process by which a fully or partially denatured polypeptide adopts secondary, tertiary and quaternary structure like that of the cognate native molecule. A properly refolded polypeptide has biological activity that is at least about 10% of the non-denatured molecule, preferably biological activity that is substantially that of the non-denatured molecule. In some embodiments, the biological activity is at least about 15%, about 20%, about 25%, about 30%, about 40%, about 50%, about 75%, about 90% of the non-denatured molecule. Where the native polypeptide has disulfide bonds, oxidation to form native intramolecular disulfide bonds is a desired component of the refolding process.

The "biological activity" of a polypeptide as used herein, means at least about 10% of maximal known specific activity as measured in an assay that is generally accepted in the art to be correlated with the known or intended utility of the polypeptide. For polypeptides intended for therapeutic use, the assay of choice is one accepted by a regulatory agency to which data on safety and efficacy of the polypeptide must be submitted. In some embodiments, a polypeptide having at least about 10% or greater than about 10% of maximal known specific activity is "biologically active" for the purposes of the invention. In some embodiments, the biological activity is at least about 15%, about 20%, about 25%, about 30%, about 40%, about 50%, about 75%, about 90% of the non-denatured molecule.

Provided herein are methods using hydrostatic pressures greater than atmospheric pressure to solubilize fusion protein aggregates and proteolytically cleave the fusion partner from the target polypeptide in a single process step to yield soluble target polypeptide in high yield. The methods also include steps for refolding the target polypeptide, and, in some cases, the production of biologically active target polypeptides. The processes will concomitantly also cleave and refold any fusion protein monomers (e.g., soluble forms of the fusion protein) that are present in the mixture). These methods can also be applied to soluble fusion proteins to cleave the fusion protein and produce soluble target polypeptide in high yield (e.g., by avoiding off pathway aggregation that often occurs after the cleavage process).

As an example of the methods provided herein, it can be demonstrated that increased hydrostatic pressure (e.g., 2000 bar) can be coupled with recombinant 3C protease to solubilize a protein aggregate of the target polypeptide (e.g., recombinant protein of interest) and cleave from the recombinant protein of interest its ubiquitin fusion partner. This process is advantageous in comparison to solubilization and cleavage of the same fusion protein using traditional denaturant—(e.g., chaotropes, etc.) based methods that necessarily incorporate a dilution step after solubilization in order to dilute the denaturants to a low enough level to maintain the activity of the protease.

In various embodiments, the yield of soluble (and, optionally, biologically active) target polypeptide is enhanced by 5%, 10%, 15%, 20%, 25%, 30%, 40%, 50%, 60%, 70%, 80%, 90%, or 100% over the yield of soluble (and, optionally, biologically active) target polypeptide that obtained if the target polypeptide is produced by solubilization with denaturants and subsequent dilution of denaturant and proteolytic cleavage.

In the present context, the term "a portion of a target polypeptide," and cognates thereof, recognizes that the yield of soluble target polypeptide may not be 100% and that some percentage of the target polypeptide incorporated in the fusion protein aggregate (starting material) may not be completely solubilized and cleaved. As mentioned previously, in the exemplary fusion protein studies, the yield has approximated 100%, however, it is anticipated that for some systems, a percentage of the target polypeptide may be in an insoluble form (e.g., the yield may not be 100%), for example less than about 50%, less than about 40%, less than about 30%, less than about 20%, less than about 10%, less than about 7%, less than about 5%, less than about 3%, less than about 2%, less than about 1% of the target polypeptide present may be in an insoluble form.

These methods have wide applicability and can also be used with fusion proteins that are autocatalytic. That is, the methods can be used with fusion proteins in which the fusion partner attached to the target polypeptide has proteolytic activity or incorporates a portion of sequence that is autocatalytic. In such cases, after solubilization of the fusion protein aggregates, the proteolytic fusion partner can cleave itself from the target protein without the need for additional protease.

Fusion Proteins

A wide variety of fusion protein aggregates may be solubilized and cleaved by the methods described herein. As used herein, the term "fusion protein," and cognates thereof, refers to polypeptide constructs incorporating a "fusion partner" and a "target polypeptide," designed such that there is a cleavage site between the fusion partner and the target polypeptide that can be cleaved proteolytically.

The cleavage site can be designed such that the sequence of the cleavage site is unique to the cleavage site and can be proteolytically cleaved by a protease, while leaving the target polypeptide sequence intact. The protease is thus specific for the cleavage cite. As used in this context, the term "specific" refers to the protease cleaving the fusion protein at the cleavage site while leaving the target polypeptide substantially intact (e.g., where less than about 10%, less than about 5%, less than about 3%, less than about 1% of the target polypeptide itself is cleaved by the protease).

The term "fusion partner" refers to the amino acid sequence co-expressed with a target polypeptide in order to enhance expression of the target polypeptide in a polypeptide expression system, in which the target polypeptide and fusion partner do not occur together in nature.

Recombinant DNA technology has permitted the expression of relatively large amounts of target polypeptides (for example, growth hormone) from transformed host cells such as $E. coli$. These polypeptides are often sequestered in insoluble inclusion bodies in the cytoplasm and/or periplasm of the host cell. The inclusion bodies or cytoplasmic aggregates contain, at least in part, the heterologous polypeptide to be recovered. These aggregates often appear as bright spots under a phase contrast microscope.

A host cell is a microbial cell such as bacteria and fungi (e.g., yeast) or other suitable cell including animal or a plant cell that has been transformed to express the heterologous polypeptide of interest. Host cells that can be used to provide the fusion proteins used in the methods described herein include those in which the heterologous polypeptide expressed by the cell is sequestered in inclusion bodies (also referred to as "refractile bodies"). An exemplary host cell is $E. coli$ K12, strain W31 1OG (pBGHI).

As will be appreciated by the skilled artisan, fusion partners may be selected to enhance expression or isolation of the target polypeptide by a variety of mechanisms. For example, the fusion partner may be selected for increased solubility of the fusion protein when compared to the target polypeptide sequence alone within the expression system. The fusion partner may also be selected to decrease the toxicity of the target polypeptide to the expression system itself, where toxicity is decreased compared to expression of the target polypeptide without the fusion partner. Additionally, fusion partners may also be selected to facilitate purification of the target polypeptide after expression and initial isolation (e.g., His-tags, etc.). In some cases, the fusion partner may be a combination of an two or more fusion partners as described herein, and therefore incorporate more than one cleavage site, where the two or more cleavage sites may be the same or different (i.e., specific for the same protease or different proteases). For example, one fusion partner may increase solubility or decrease toxicity of the target polypeptide, while the second or additional fusion partner(s) may facilitate purification, etc. In some embodiments, the fusion protein incorporates, e.g., one, two, three, four or more fusion partners. In some embodiments, the fusion protein incorporates e.g., one, two, three or four cleavage sites, wherein the cleavage sites may, independently, be specific for the same or different proteases. In some embodiments, the fusion protein incorporate In some cases, the fusion partner may be proteolytic. For example, when the fusion protein is solubilized, the fusion partner is able to cleave apart the fusion partner and target polypeptide, in other words, the fusion protein itself is autocatalytic. In some cases, the fusion partner may be a combination of an autocatalytic protease and an additional fusion partner as described herein, for example, in combination with a fusion partner to increase solubility or decrease toxicity to the host cell, facilitate purification, etc.

Thus, in some embodiments, the fusion partner is selected to enhance solubility, decrease toxicity, facilitate purification of the target polypeptide or is proteolytic. Where the fusion partner is said to increase or decrease a particular characteristic of the target polypeptide, the comparison is between the target polypeptide expressed without the fusion partner and the target polypeptide expressed with the fusion partner. In some embodiments, the fusion partner may facilitate the expression of a multimeric target polypeptide, where upon cleavage of the fusion partner the separate chains of the target polypeptides are able to multimerize. In some embodiments the mulimeric polypeptide is a dimer, trimer or tetramer.

As is well known to the skilled artisan, expression of a target polypeptide as a fusion protein often results in the production of fusion protein aggregates or, in some cases, a mixture of fusion protein aggregates and soluble fusion protein (e.g., fusion protein monomers, which may occur in a variety of forms, such as denatured, misfolded, etc.). The fusion protein aggregates can take many forms, including soluble aggregates and insoluble aggregates.

As used herein, a "fusion protein aggregate," and cognates thereof, are defined as being composed of a multiplicity of polypeptide molecules wherein non-native noncovalent interactions and/or non-native covalent bonds (such as non-native intermolecular disulfide bonds) hold the polypeptide molecules together. In the context of a fusion protein, a "non-native" noncovalent interaction or noncovalent bond refers to a noncovalent interaction or noncovalent bond which is not present in the naturally-occurring target polypeptide alone (without the fusion partner) or not present in the naturally-occurring fusion partner alone (without the target polypeptide); if the target polypeptide is not a naturally-occurring polypeptide, a "non-native" noncovalent interaction or non-covalent bond in the fusion protein refers to an noncovalent interaction or noncovalent bond not present in the biologically active target polypeptide alone (without the fusion partner); if the fusion partner is not naturally-occurring, a "non-native" noncovalent interaction or noncovalent bond in the fusion protein refers to a noncovalent interaction or noncovalent bond not present in the fusion partner alone (without the target polypeptide). Typically, but not always, an aggregate contains sufficient molecules so that it is insoluble; such aggregates are insoluble aggregates. There are also abnormal oligomeric polypeptides that occur in aggregates in solution; such aggregates are soluble aggregates. In addition, there is typically (but not always) a display of at least one epitope or region on the aggregate surface that is not displayed on the surface of native, non-aggregated protein. "Inclusion bodies" are a type of aggregate of particular interest to which the present methods are applicable.

Inclusion bodies of fusion proteins are often formed in expression systems and result in the sequestration of the fusion protein as an insoluble mass. While inclusion bodies are difficult to solubilize and the traditional solubilization steps (e.g., use of denaturants, including, usually, chaotropes) are expensive and time consuming, this sequestration of the fusion protein as an insoluble mass does have the side benefit that the fusion protein (and the target polypeptide it incorporates) is usually resistant to degradation by non-specific proteases within the expression system due to the inaccessibility of cleavage sites. This feature thus allows the isolation of intact fusion protein from the expression system itself with minimal non-specific protease degradation.

Exemplary fusion partners include NusA (N utilization substance protein A), DsbA, gphD, his-tags (Chaga et al. 1999), calmodulin-binding protein, FLAG (Einhauer and Jungbauer 2001), streptag II (Skerra and Schmidt 2000), HA-tag (Hage 1999), Softag1 and Softag 3 (Burgess and Thompson 2002), c-myc (Terpe 2003), T7-tag (Chatterjee and Esposito 2005), S-tag (Slootstra et al. 1997), elastin-like peptides (Meyer et al. 2001), chitin-binding domain (Humphries et al. 2002), thioredoxin (Tanaka et al. 2004), xylanase 10A (Kavoosi et al. 2004), glutathione S-transferase (Smith and Johnson 1988), maltose binding protein (Fox and Waugh 2003), tobacco etch virus (Shih et al. 2005), self-cleavable affinity tags (e.g., Humphries H E et al., (2002) *Protein Expression And Purification* 26:243-248; Mao H. (2004) *Protein Expression And Purification* 37:253-263) and ubiquitin (Kitahara et al. 2001) (the foregoing references are each incorporated by reference herein in their entirety). Additional fusion partners known to the skilled artisan can also be employed in keeping with the teachings provided herein, including, for example the affinity tags. Additional guidance is also provided in Arnau et al. 2006, which is hereby incorporated by reference in its entirety, particularly with regard to the selection and use of fusion partners.

In certain embodiments, the fusion partner is a His6Tag. In some embodiments, the fusion partner is maltose-binding protein. In other embodiments, the fusion partner is thioredoxin. In certain embodiments, the fusion partner is ubiquitin. In particular embodiments, the fusion partner is glutathione-s-transferase. In certain embodiments, the fusion partner is DsbA. In certain embodiments, the fusion partner is FLAG. In some embodiments, the fusion partner is gphD. In certain embodiments, the fusion partner is c-myc. In other embodiments, the fusion partner is TEV. In certain embodiments, the fusion partner is a streptag II. In some embodiments, the fusion partner is ubiquitin. In certain embodiments, the fusion partner is NusA. In some embodiments, the fusion partner is calmodulin binding protein. In certain embodiments, the fusion partner is an elastin-like peptide. In some embodiments, the fusion partner is a Softage 1 or Softag 3. In certain embodiments, the fusion partner is a STag. In certain embodiments, the fusion partner is chitin-binding domain.

In some variations where the fusion protein is autocatalytic, the fusion protein may include a fusion partner that comprises a fusion partner as described herein plus a protease (e.g., fusion protein=fusion partner+protease+cleavage site+target polypeptide). In other variations where the fusion protein is autocatalytic, the fusion protein may include a protease alone as the fusion partner (e.g., fusion protein=protease (acting as fusion partner)+cleavage site+target polypeptide. In some embodiments, an optional affinity tag may also be located terminal to the target polypeptide, (e.g., fusion protein=fusion partner+protease+cleavage site+target polypeptide+affinity tag; fusion protein=protease (acting as fusion partner)+cleavage site+target polypeptide+affinity tag, etc.) Certain variations where optional affinity tags are included are depicted schematically in FIGS. 14A and 14B.

In some embodiments the fusion partner is a protease. In some embodiments the fusion partner includes a protease and a fusion partner as described herein. In some of these embodiments, the protease is TEV. In certain embodiments, the fusion partner is a His6Tag and a protease. In some embodiments, the fusion partner is maltose-binding protein and a protease. In other embodiments, the fusion partner is thioredoxin and a protease. In particular embodiments, the fusion partner is glutathione-s-transferase and a protease. In certain embodiments, the fusion partner is DsbA and a protease. In some embodiments, the fusion partner is gphD and a protease. In other embodiments, the fusion partner is TEV. In some embodiments, the fusion partner is ubiquitin and a protease. In certain embodiments, the fusion partner is NusA and a protease. In some embodiments, the fusion partner is calmodulin binding protein and a protease.

The fusion protein may also optionally include an affinity tag (e.g., His-tag) attached to the target polypeptide portion of the fusion protein.

As used herein the term "target polypeptide," and its cognates, refers to the sequence of amino acids of interest, and which is expressed in an expression system along with its fusion partner. The target polypeptide may include any sequence of amino acids, including sequences comprising the sequence of a naturally occurring polypeptide, modifications of naturally occurring polypeptides (e.g., mutants of naturally occurring polypeptide sequences, etc.), sequences comprising portions of multiple naturally-occurring polypeptides, sequences combining portions of naturally-occurring polypeptides and non-naturally occurring sequences, non-naturally occurring polypeptides, etc. The target polypeptide may also comprise a fragment of a naturally occurring polypeptide. In some cases, the target polypeptides, under suitable solution conditions (e.g., conditions favoring the native state), will adopt a predominant stable or native three-dimensional fold (e.g., as in fragments of antibodies (e.g., domain antibodies, etc.), folding domains, etc.). Target polypeptides can include monomeric polypeptides; oligomeric (also referred to as "multimeric") (e.g., dimeric, (e.g., heterodimeric, homodimeric) trimeric (e.g., heterotrimeric, homotrimeric), tetrameric (e.g., heterotetrameric, homotetrameric), etc. polypeptides; disulfide bonded polypeptides; glycosylated polypeptides, etc. The target polypeptides are not limited to any particular fold or motif (e.g., they may include α-helical, β-sheet, loops, turns, etc. as secondary structure). Exemplary target polypeptides may include hormones (e.g., growth factors (e.g., insulin-like growth factors, recombinant human growth hormone, cystine-knot growth factors (e.g., vascular endothelial growth factor (VEGF)), etc.), cytokines (e.g., interferons, erythropoietin, etc.)), antibodies (e.g., monoclonal antibodies, fragments of antibodies (Fab fragments, F(ab')2 fragments, Fd fragments, Fv fragments, dAb (single domain) fragments (Ward et al., Nature 341:544 (1989)); isolated complementarity determining regions retaining specific-antigen binding activity; and scFv (recombinantly-produced single chain Fv), etc.), enzymes (e.g., phosphatases, kinases, etc.), structural proteins, receptors, metal binding proteins, prions (e.g., prion protein (PrP)), amyloids (e.g., beta amyloid, amyloid precursor protein, etc.), etc. Target polypeptides may also include mutants, chimera's, fusions, or fragments of the foregoing. Target polypeptides may include at least about 25 amino acids.

The target polypeptides may also include, but are not limited to, small monomeric polypeptides (e.g., from about 25 to about 60 amino acids) that are designed to mimic the active site of larger polypeptides. In some variations, these polypeptides may contain a portion of the amino acid sequence of a parent polypeptide (naturally occurring or engineered) with a known activity. In certain variations, the polypeptide may contain a combination of certain portions of the parent polypeptide interspersed with engineered sequences. In particular variations, the polypeptide sequence will be unrelated to the parent polypeptide sequence, however, the polypeptide sequence will have been selected through various screening methods appropriate to the activity of the parent polypeptide to mimic the activity of the parent polypeptide. In many of these variations, these polypeptides will contain fewer amino acid residues than the parent polypeptide whose activity they are mimicking.

In some embodiments, the small monomeric polypeptides may or may not adopt a predominant or stable native conformation. For example, in some of these polypeptides the multiple conformation of tertiary and/or secondary structure may exist within a population of molecules. In some variations, the small monomeric polypeptides will adopt a predominant tertiary conformation. In some variations, the small monomeric polypeptides will not adopt a predominant fold until they are in the presence of a target. For example, a receptor to which the polypeptide is an agonist or antagonist, an enzyme that the polypeptide inhibits or stimulates, etc.

In some variations, the small monomeric polypeptides are from about 30 to about 60 amino acids, from about 30 to about 58 amino acids, from about 30 to about 56 amino acids, from about 30 to about 54 amino acids, from about 30 to about 50 amino acids, from about 30 to about 45 amino acids, from about 30 to about 40 amino acids, from about 35 to about 60 amino acids, from about 35 to about 55 amino acids, from about 35 to about 50 amino acids, from about 35 to about 45 amino acids, from about 35 to about 40 amino acids, from about 40 to about 60, from about 40 to about 55, from about 40 to about 50 amino acids in length.

In some embodiments, the target polypeptide may be a monomer or an oligomer (e.g., dimer, trimer, tetramer, etc.) when in its native conformation. The oligomers may be homo-oligomers (e.g., homodimers, homotrimers, homotetramers, etc.) or hetero-oligomers (e.g., heterodimer, heterotrimer, heterotetramers, etc.).

Target polypeptides may be selected based on their utility in any of a number of fields, including, but not limited to, therapeutics (e.g., pharmaceutical drug applications, mammalian therapeutics (e.g., where the mammal is a primate (e.g., human, ape, monkey, etc.), dog, horse, mouse, etc.); research and development applications (e.g., identification of new sequences, identification of new folds, discovery of new protein structures); industrial processes (e.g., detergents, decontamination enzymes, chemical synthesis, bioremediation, etc.); consumer applications (e.g., enzymes used in home laundry or other detergents, etc.), etc. The methods provided herein should reduce the cost of production, especially large-scale production, of the targeted polypeptides for use in any field where polypeptides are employed.

As described in greater details in the examples, the target polypeptide (e.g., protein of interest) is expressed as a fusion protein linked to a truncated yeast ubiquitin sequence (FIG. 13B) as the fusion partner. The fusion protein is designed such that the ubiquitin sequence is cleaved from the target polypeptide (e.g., protein of interest) following isolation of the fusion protein from the fermentation harvest. The fusion protein consists of the first 41 amino acids from yeast ubiquitin, followed by 6 amino acids that create a 3C protease cleavage site, fused to the complete sequence of the protein of interest. Cleavage of the fusion protein by recombinant 3C protease (3CP) can then occur.

Described in Example 6, is an exemplary process for autocatalytic fusion protein in which, upon solubilization of the fusion protein aggregates, the fusion partner cleaves apart the fusion partner and target polypeptide efficiently and at reduced cost to traditional methods.

Standard techniques for cloning, DNA isolation, amplification and purification, for enzymatic reactions involving DNA ligase, DNA polymerase, restriction endonucleases and the like, and various separation techniques are those known and commonly employed by those skilled in the art for the production of fusion proteins. A number of standard techniques are described in Ausubel et al. (1992) Current Protocols in Molecular Biology, Green/Wiley, New York, N.Y.; Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) Genetic Engineering: Principles and Methods, Vols. 1-4, Plenum Press, New York; and Ausubel et al. (1992) Current Protocols in Molecular Biology, Greene/Wiley, New York, N.Y. Abbreviations and nomenclature, where employed, are deemed standard in the field and commonly used in professional journals such as those cited herein.

Proteases

A wide variety of proteases may be used in the practice of the methods described herein. In most cases the protease will be added to the mixture as a separate molecule, however, as noted previously, in some cases the fusion partner will also serve as the protease. As a class, many proteases appear to be stable and active at hydrostatic pressure greater than atmospheric. In fact, high hydrostatic pressures (up to 4000 bar) have been shown to increase the catalytic activity some proteases (Hendrickx et al. 1998; Mozhaev et al. 1996). Although the mechanism remains unclear (and not wishing to be bound by theory), it appears that the high hydrostatic pressures increase reaction kinetics through enzymatic reactions that have negative activation volumes, while favoring or even stabilizing the native enzyme conformation (Mozhaev et al. 1996). Researchers have also suggested that proteases are unusually stable at elevated pressures due to their low partial specific volume (Gekko 2002; Gekko and Hasegawa 1986;

Seefeldt et al. 2003). However, for some proteases, higher pressures (>5000 bar) may inactive enzymes and proteases by inducing protein denaturation (Hendrickx et al. 1998; Mozhaev et al. 1996; Royer 2002).

Proteases that are suitable for use in the present invention are those that can proteolytically cleave apart the fusion partner and target polypeptide at the cleavage site designed into the fusion protein sequence. Generally, proteolytic cleavage is considered the breaking of peptide bonds by a class of enzymes known as "proteases," which are well known to the skilled artisan. Selection of a particular protease will depend upon the cleavage site designed into the fusion protein, as well as the sequence of the target polypeptide. Additionally, the protease should be biologically active under the conditions used for solubilization of the fusion protein aggregates.

As will be understood by the skilled artisan in view of the teaching provided herein, a protease that cleaves apart portions of the target polypeptide sequence itself will likely be undesirable. Many proteases are available commercially and their cleavage characteristics known. For example, Factor Xa (New England BioLabs) is commonly used in conjunction with maltose-binding protein, one of the most commonly used fusion partners used to increase solubility of target polypeptides. Additional combinations of fusion partners and protease are described in Arnau et al., 2006 (incorporated by reference in its entirety herein) and can provide guidance to the skilled artisan. Additional fusion partners and proteases are also described herein.

General classes of proteases include, but are not limited to, serine proteases, cysteine proteases (e.g., 3C protease, etc.), metalloproteases, etc.

Exemplary proteases for use in the methods described herein include, but are not limited to, α-chymotrypsin (Hawley 1971; Mozhaev et al. 1996), enterokinase (Leong 1999), Factor Xa (Leong 1999), thrombin (Leong 1999), PreScission (Lichty et al. 2005), TEV protease (Nallamsetty and Waugh 2005; Shih et al. 2005), 3C protease (Leong 1999), Sortase A (Mao 2004), Granzyme B (Lorentsen et al. 2005), Intein (Humphries et al. 2002), SUMO (Butt et al. 2005), DAPase (Pedersen et al. 1999), Aminopeptidase M, Carboxypeptidase A, Carboxypeptidase B (Kenig et al. 2005), kumamolisin (Fujimoto et al. 2006), vimelysin (Ikeuchi et al. 2000), and thermolysin (Kunugi et al. 1999).

Optimal conditions (e.g., pressure, temperature, pH, etc.) conditions will vary, as previously noted, depending on the particular fusion protein and protease chosen. However, information regarding conditions for some proteases has been described. The catalytic activity of vimelysin was found to be maximized at 15° C., 1500-2000 bar, at a pH of 4.8 (Ikeuchi et al. 2000). Activity was still present up to pressures of 4000 bar (Ikeuchi et al. 2000). The protease kumamolisin was found to be active at pressures of at least 5000 bar at pH's of 5.5 (Fujimoto et al. 2006). The protease calpain is stable up to pressures of 2000 bar at a pH of 7.5 (Bessiere et al. 1999). The activity of the protease thermolysin increases at with increasing pressure up to 2000 bar at a pH of 6.2 (Kunugi et al. 1999). The above-listed references are hereby incorporated in their entirety.

Additionally, studies by Mozhaev et al. demonstrated that the protease α-chymotrypsin's chemical activity and thermal stability is increased by high pressure treatment (Mozhaev et al. 1996) (incorporated herein in its entirety). The chemical activity of α-chymotrypsin increased 100 times upon treatment to 5000 bar in comparison to samples incubated at atmospheric pressure under identical solution conditions. A similar effect was observed at studies conducted at temperatures of 50° C. In this case, pressure treatment to 4000 bar minimized the extent of thermal activation.

As is apparent from the work referenced above, many proteases will have sufficient proteolytic activity at the pressures required by the methods described herein to proteolytically cleave a wide variety of fusion proteins. These references, as well as others available to the skilled artisan, also provide the skilled artisan with guidance as to methods for testing the proteolytic activity of proteases prior to use in the present methods.

In view of the teaching provided herein, particularly in Examples 2-4, selection and optimization of particular combinations of fusion protein/protease/solution conditions is possible for the skilled artisan without undue experimentation.

Variations of the Methods

The methods described in detail herein can be broadly generalized as the solubilization of fusion protein aggregates (and fusion protein monomers) with the subsequent proteolytic cleavage of the fusion partner from the target polypeptide in a single processing step at increased pressure (e.g., step (a) of the methods) to yield soluble target polypeptide as well as solubilization (if needed) and cleavage of soluble fusion protein (if present). Subsequent to proteolytic cleavage and generation of the soluble target polypeptide, the sample is brought back to atmospheric pressure under conditions where it is soluble.

However, there are numerous variations on these methods included within the scope of the present invention which may include additional steps either before, during or after step (a) is performed and/or before, during or after step (b) is performed. Similarly, the aqueous solution and/or suspension in which the process is performed may contain additional components to optimize the solubilization and cleavage process. Variation of both method steps and components are discussed in greater detail below.

As used in the present context, the term "soluble" (as in "soluble target polypeptide"), and cognates thereof, refers to where a polypeptide (e.g., the target polypeptide) is solubilized in the medium in which it is present. In other words the polypeptide is not associated with other polypeptide molecules to form aggregates (either insoluble or soluble aggregates). Target polypeptide in its native conformation, including biologically active target polypeptide would be considered soluble target polypeptide. It should be noted that where target polypeptides are oligomeric in their native conformation (e.g., where they possess quaternary structure) they would still be soluble when associated as either homo-oligomers or hetero-oligomers.

In some embodiments, the soluble target polypeptide will be biologically active at atmospheric pressure. In other embodiments, the soluble target polypeptide will not be biologically active at atmospheric pressure. It should be noted that for certain polypeptides, they may achieve a native conformation or nearly-native conformation but will not be biologically active until a ligand binding partner is present (e.g., metal ion, target polypeptide substrate, etc.).

In some variations of the methods step (a) may be preceded by isolation and, optionally, further purification of the fusion protein aggregates from the host expression system.

As in the case where the fusion protein aggregate is an inclusion body, standard industry techniques can be used to lyse bacterial cells, and, optionally, purify inclusion bodies through a variety of techniques. Various sedimentation protocols known to the skilled artisan can be employed. For example, centrifugation and washing with, for example, Triton X-100 and 1 M NaCl (Bowden et al. 1991).

Additionally, refractile bodies, otherwise known as inclusion bodies, can be recovered using standard techniques as described, for example, in U.S. Pat. No. 4,652,630. For example, the host cell can be disrupted by mechanical means such as a Manton-Gaulin homogenizer or French press. In some cases the disruption process can be conducted so that cellular debris from the host organism is so disrupted that it fails to sediment from the homogenate solution under low speed centrifugation sufficient to sediment the refractile bodies, thus reducing the amount of impurities. The refractile bodies can then be resuspended, washed and centrifuged again. The supernatant can then be discarded to yield a substantially pure preparation of refractile bodies. Although not critical to the practice of the present invention, it may also be useful for the refractile body preparation to be homogenized again to ensure a freely dispersed preparation devoid of agglomerated refractile bodies. The preparation may be homogenized in, for example, a Manton-Gaulin homogenizer at 3000-5000 psig.

Prior to step (a), the components of the aqueous solution and/or suspension may be mixed and brought into contact with the fusion protein aggregates (e.g., the washed and purified inclusion bodies can be placed in a solubilization and protease cleavage buffer). Components added to the aqueous solution and/or suspension are selected based on a variety of criteria, including pH and ionic strength, and reduction potential. Proteases required to cleave the fusion protein are also added prior to pressurization.

In some embodiments, the fusion protein aggregates are the last component added to the aqueous solution and/or suspension. In certain embodiments, the protease is the last component added to the aqueous solution and/or suspension.

Fusion protein may be present in a concentration of from about 0.001 mg/ml to about 300 mg/ml. Thus, in some embodiments the fusion protein is present in a concentration of from about 0.001 mg/ml to about 250 mg/ml, from about 0.001 mg/ml to about 200 mg/ml, from about 0.001 mg/ml to about 150 mg/ml, from about 0.001 mg/ml to about 100 mg/ml, from about 0.001 mg/ml to about 50 mg/ml, from about 0.001 mg/ml to about 30 mg/ml, from about 0.05 mg/ml to about 300 mg/ml, from about 0.05 mg/ml to about 250 mg/ml, from about 0.05 mg/ml to about 200 mg/ml, from about 0.05 mg/ml to about 150 mg/ml, from about 0.05 mg/ml to about 100 mg/ml, from about 0.05 mg/ml to about 50 mg/ml, from about 0.05 mg/ml to about 30 mg/ml, from about 10 mg/ml to about 300 mg/ml, from about 10 mg/ml to about 250 mg/ml, from about 10 mg/ml to about 200 mg/ml, from about 10 mg/ml to about 150 mg/ml, from about 10 mg/ml to about 100 mg/ml, from about 10 mg/ml to about 50 mg/ml, or from about 10 mg/ml to about 30 mg/ml.

As part of step (a), the aqueous solution and/or suspension is incubated at increased hydrostatic pressures, (e.g., in the range of 500-10,000 bar at a temperature within 0-100° C.) for a period of time sufficient to allow solubilization and proteolytic cleavage of the fusion protein. Pressure and temperatures are selected to facilitate aggregate dissociation (also referred to as disaggregation) while favoring both the protease and the target polypeptide in their native conformations. In this processing step, fusion protein aggregates are solubilized (St. John et al. 1999) and proteolytic cleavage of the fusion protein follows.

As used in the present context the phrases "time sufficient to allow solubilization," "time sufficient for formation of soluble target polypeptide," and cognates thereof refer to the time needed for the fusion protein aggregates to be solubilized and subsequent proteolytic cleavage to take place. For example, the time period of step (a) of the methods described herein. The time needed will vary according to the characteristics of the fusion protein (and the form of aggregate in which the fusion protein is present in the mixture) and the protease. The time period may also be affected by the characteristics of the target polypeptide and whether the reaction conditions have been fully optimized. The time required for optimal solubilization and cleavage can be determined using the teachings provided herein, as will be appreciated by the skilled artisan.

Typically, the time sufficient for solubilization and cleavage is about 15 minutes to about 50 hours, or possibly longer depending on the particular fusion protein, protease and target polypeptide (e.g., up to about 1 week, about 5 days, about 4 days, about 3 days, etc.). Thus, in some embodiments of the methods, the time sufficient for formation of soluble target polypeptide may be from about 2 to about 30 hours, from about 2 to about 24 hours, from about 2 to about 18 hours, from about 1 to about 10 hours, from about 1 to about 8 hours, from about 1 to about 6 hours, from about 2 to about 10 hours, from about 2 to about 8 hours, from about 2 to about 6 hours, or about 2 hours, about 6 hours, about 10 hours, about 16 hours, about 20 hours, or about 30 hours, from about 2 to about 10 hours, from about 2 to about 8 hours, from about 2 to about 6 hours, from about 12 to about 18 hours, or from about 10 to about 20 hours.

After sufficient time is allowed for fusion protein aggregate solubilization and fusion protein cleavage to occur, yielding soluble target polypeptide, refolding steps may also be performed. The specific refolding steps conducted will be dependent upon the nature of the target polypeptide, as will be appreciated by the skilled artisan, and techniques for determining optimal conditions are described in greater detail herein.

Where the target polypeptide does not include disulfide bonds, refolding will occur after protease cleavage without the addition of any further processing steps or components. In such cases, the time period in step (a) may incorporate a period of time for refolding.

Typical refolding times are in the range of 3 hours to about 50 hours. For example, the refolding time may be from about 3 hours to about 50 hours (or longer, depending on the nature of the target polypeptide (e.g., up to about 1 week, about 5 days, about 4 days, about 3 days, etc.). In some embodiments, refolding time may be from about 3 to about 30 hours, from about 3 to about 24 hours, from about 3 to about 18 hours, from about 3 to about 10 hours, from about 3 to about 8 hours, from about 3 to about 6 hours, from about 4 to about 10 hours, from about 4 to about 8 hours, from about 4 to about 6 hours, or about 4 hours, about 6 hours, about 10 hours, about 16 hours, about 20 hours, or about 30 hours, from about 2 to about 10 hours, from about 6 to about 8 hours, from about 6 to about 18 hours, from about 12 to about 18 hours, or from about 10 to about 20 hours.

If the target polypeptide of interest includes disulfide bonds, a disulfide shuffling agent pair (e.g., 0.5-10 mM oxidized and reduced glutathione, or cystamine/cysteamine, or cysteine/cystine, etc.) may need to be added to the solubilized and cleaved target polypeptide mixture to facilitate proper disulfide formation (e.g., step a-1) or, if the protease is proteolytically active in the presence of the disulfide shuffling agent pair, the disulfide shuffling agent pair can be included in the aqueous suspension and/or solution of step (a). In this case, the solubilization/cleavage/refolding of the target polypeptide will all occur during step (a) without the need for any additional processing steps. However, it should be noted that in order to optimize the yield of refolded target polypeptide, it may be advantageous to alter the increased hydrostatic pressure of step (a) for a period of time to favor refolding. For example, in some cases after a period of time during step (a) the increased hydrostatic pressure is reduced or increased to facilitate refolding. Exemplary increased hydrostatic pressure ranges for the facilitation of refolding are described in detail herein and can be incorporated into a period of altered hydrostatic pressure for step (a). It should be noted that in some embodiments, refolding will occur when the hydrostatic pressure is maintained at the increased hydrostatic pressure of step (a).

In some embodiments, the methods can include, immediately after step (a) a step (a-3) of: altering the increased hydrostatic pressure for a time sufficient to facilitate the formation of native disulfide bonds. In some variations, the increased hydrostatic pressure of step (a) is reduced. In other variations, the increased hydrostatic pressure of step (a) is increased. The ranges applicable to the alteration of hydrostatic pressure to facilitate formation of native disulfide bonds can be as described herein in connection with performing step a-2, below.

Where the disulfide shuffling agent pair is added after step (a), (e.g., as step a-1), the addition of the disulfide shuffling agent pair may be undertaken while the mixture is maintained at increased atmospheric pressure, under a hydrostatic pressure that is reduced compared to the hydrostatic pressure of step (a), but greater than atmospheric temperature, or at atmospheric pressure. Where the addition of the disulfide shuffling agent pair is performed at increased atmospheric temperature, the devices described in more detail below may be employed, as well as those available to the skilled artisan.

Once the disulfide shuffling agent pair is present in the mixture, the mixture is again incubated at increased hydrostatic pressure for a further period of time sufficient to facilitate the formation of native disulfide bonds (e.g., step a-2). This further period of increased hydrostatic pressure can be carried out at the same hydrostatic pressure or a different hydrostatic pressure from the hydrostatic pressure of step (a). In some embodiments, the hydrostatic pressure of step (a) is maintained. In other embodiments the hydrostatic pressure for the further time period is reduced compared to the hydrostatic pressure of step (a). In still other embodiments the hydrostatic pressure for the further time period is increased compared to the hydrostatic pressure of step (a).

In some variations of the methods the further period of increased pressure may be performed at a hydrostatic pressure of from about 500 bar to about 5000 bar, from about 500 bar to about 4000 bar, from about 1000 bar to about 4000 bar, from about 1000 bar to about 3000 bar, from about 1000 bar to about 2000 bar, from about 1500 bar to about 4000 bar, from about 1500 bar to about 3000 bar, from about 2000 bar to about 4000 bar, or from about 2000 bar to about 3000 bar. In particular variations, the further period of increased hydrostatic pressure is from about four-fifths of the increased hydrostatic pressure in step (a) to about one-tenth of the increased hydrostatic pressure in step (a). For example, the further period of increased hydrostatic pressure is carried out at pressure of from about four-fifths to about one-fifth, from about two-thirds to about one-tenth, from about two-thirds to about one-fifth, from about two-thirds to about one-third, about one-half, or about one-quarter of the hydrostatic pressure of step (a).

As used in the present context the phrase "time sufficient to facilitate formation of native disulfide bonds," and cognates thereof, refers to the time needed for the target polypeptide formed by proteolytic cleavage to rearrange to eliminate non-native disulfide bonds and to allow native-disulfide bonds to form. For example, the time period of step (a-2) of the methods described herein, incorporated into step (a) (where the disulfide shuffling agent pair may be included in the initial mixture with the fusion protein aggregates and protease (where protease activity is still sufficient for cleavage in the presence of the pair)). The time needed will vary according to the characteristics of the target polypeptide (e.g., number of disulfide bonds, relative stability of non-native and native disulfide bonds, etc.), the disulfide shuffling pair, and whether the reaction has been optimized for the disulfide shuffling process. The time required for native disulfide bond formation can be determined using the teachings provided herein; as will be appreciated by the skilled artisan.

Typically the time sufficient to facilitate the formation of native disulfide bonds is from about 10 minutes to about 50 hours (or longer, depending on the nature of the target polypeptide (e.g., up to about 1 week, about 5 days, about 4 days, about 3 days, etc.)). Thus in some embodiments, the time sufficient to facilitate the formation of native disulfide bonds may be from about 2 to about 30 hours, from about 2 to about 24 hours, from about 2 to about 18 hours, from about 1 to about 10 hours, from about 1 to about 8 hours, from about 1 to about 6 hours, from about 2 to about 10 hours, from about 2 to about 8 hours, from about 2 to about 6 hours, or about 2 hours, about 6 hours, about 10 hours, about 20 hours, or about 30 hours, from about 2 to about 10 hours, from about 2 to about 8 hours, from about 2 to about 6 hours. In some embodiments, time may be from about 3 hours to about 50 hours (or longer, depending on the nature of the target polypeptide). In some embodiments, the time sufficient to facilitate the formation of native disulfide bonds may be from about 3 to about 30 hours, from about 3 to about 24 hours, from about 3 to about 18 hours, from about 3 to about 10 hours, from about 3 to about 8 hours, from about 3 to about 6 hours, from about 4 to about 10 hours, from about 4 to about 8 hours, from about 4 to about 6 hours, or about 4 hours, about 6 hours, about 10 hours, about 16 hours, about 20 hours, or about 30 hours, from about 2 to about 10 hours, from about 6 to about 8 hours, from about 6 to about 18 hours, from about 12 to about 18 hours, or from about 10 to about 20 hours.

In some embodiments, following either step (a) or step (a-2), the amount of disulfide shuffling agent pair may be reduced. Reduction of the amount of the disulfide shuffling agent pair may be undertaken while the mixture is maintained at increased atmospheric pressure, under a hydrostatic pressure that is reduced compared to the hydrostatic pressure of step (a) or step (a-2), but greater than atmospheric temperature, or at atmospheric pressure (for example, after step (b)). Where the addition of the disulfide shuffling agent pair is performed at increased atmospheric temperature, the devices described in more detail below may be employed using the knowledge of the skilled artisan in view of the teaching provided herein. Methods of reducing the concentration of the disulfide agent pair include dialysis and solution exchange. Both of these methods can either be performed at increased pressures or, alternatively, the sample can be depressurized for the performance of these steps and then repressurized. Exemplary solution exchange devices for use at high pressure are shown in FIG. 8, and are additionally described herein. An exemplary dialysis method is provided below.

To perform dialysis, approximately 6 inches of dialysis tubing per sample can be prepared by placing SpectraPor regenerated cellulose dialysis membrane (or other comparable membrane), 3.5 KDa cutoff (with appropriate cutoff selected for the target polypeptide of interest), 8 mm flat width (Spectrum Labs product #133108) into a beaker with about 250 ml purified water (Sigma) for at least one hour. Dialysis chambers (one per sample) can be prepared by heat sealing the Luer end of a syringe (LUER-LOK is a registered trademark of Becton, Dickinson and Co., Franklin Lakes, N.J. for interlocking tubing and syringe seals), and numbered for identification. 600 uL of each well-mixed sample can be quickly transferred into a knotted piece of dialysis tubing. Any air bubbles present are squeezed out of the tubing before carefully knotting the open end of the dialysis membrane and placing the tubing into the appropriately-numbered syringe. After all samples are transferred to dialysis tubing and placed in their syringes, the appropriate dialysis buffer is added to fill the syringe. The syringes are then sealed with the plunger, using a needle to vent any air bubbles. At that point, samples are ready for pressure treatment.

The process of decreasing the hydrostatic pressure to atmospheric pressure (e.g., step b or where the pressure is reduced prior to addition of disulfide shuffling pairs, etc.) can be performed in either a continuous or stepwise manner.

Where the reduction in pressure is performed in a continuous manner, the rate of pressure reduction can be constant or can be increased or decreased during the period in which the pressure is reduced. In some variations, the rate of pressure reduction is from about 5000 bar/1 sec to about 5000 bar/4 days (or about 3 days, about 2 days, about 1 day). Thus in some variations the rate of pressure reduction can be performed at a rate of from about 5000 bar/1 sec to about 5000 bar/80 hours, from about 5000 bar/1 sec to about 5000 bar/72 hours, from about 5000 bar/1 sec to about 5000 bar/60 hours, from about 5000 bar/1 sec to about 5000 bar/50 hours, from about 5000 bar/1 sec to about 5000 bar/48 hours, from about 5000 bar/1 sec to about 5000 bar/32 hours, from about 5000 bar/1 sec to about 5000 bar/24 hours, from about 5000 bar/1 sec to about 5000 bar/20 hours, from about 5000 bar/1 sec to about 5000 bar/18 hours, from about 5000 bar/1 sec to about 5000 bar/16 hours, from about 5000 bar/1 sec to about 5000 bar/12 hours, from about 5000 bar/1 sec to about 5000 bar/8 hours, from about 5000 bar/1 sec to about 5000 bar/4 hours, from about 5000 bar/1 sec to about 5000 bar/2 hours, from about 5000 bar/1 sec to about 5000 bar/1 hour, from about 5000 bar/1 sec to about 1000 bar/min, about 5000 bar/1 sec to about 500 bar/min, about 5000 bar/1 sec to about 300 bar/min, about 5000 bar/1 sec to about 250 bar/min, about 5000 bar/1 sec to about 200 bar/min, about 5000 bar/1 sec to about 150 bar/min, about 5000 bar/1 sec to about 100, about 5000 bar/1 sec to about 80 bar/min, about 5000 bar/1 sec to about 50 bar/min, or about 5000 bar/1 sec to about 10 bar/min. For example, about 10 bar/min, about 250 bar/5 minute, about 500 bar/5 minutes, about 1000 bar/5 minutes, about 250 bar/5 minutes, 2000 bar/50 hours, 3000 bar/50 hours, 40000 bar/50 hours, etc. In some embodiments, the pressure reduction may be approximately instantaneous, as in where pressure is released by simply opening the device in which the sample is contained and immediately releasing the pressure.

Where the reduction in pressure is performed in a stepwise manner, the process comprises dropping the pressure from the highest pressure used to at least a secondary level that is intermediate between the highest level and atmospheric pressure. The goal is to provide an incubation or hold period at or about this intermediate pressure zone that permits a protein to adopt a desired conformation.

In some embodiments, where there are at least two stepwise pressure reductions there may be a hold period at a constant pressure between intervening steps. The hold period may be from about 10 minutes to about 50 hours (or longer, depending on the nature of the target polypeptide). In some embodiments, the hold period may be from about 2 to about 30 hours, from about 2 to about 24 hours, from about 2 to about 18 hours, from about 1 to about 10 hours, from about 1 to about 8 hours, from about 1 to about 6 hours, from about 2 to about 10 hours, from about 2 to about 8 hours, from about 2 to about 6 hours, or about 2 hours, about 6 hours, about 10 hours, about 20 hours, or about 30 hours, from about 2 to about 10 hours, from about 2 to about 8 hours, from about 2 to about 6 hours.

In some variations, the pressure reduction includes at least 2 stepwise reductions of pressure (e.g., highest pressure reduced to a second pressure reduced atmospheric pressure would be two stepwise reductions). In other embodiments the pressure reduction includes more than 2 stepwise pressure reductions (e.g., 3, 4, 5, 6, etc.). In some embodiments, there is at least 1 hold period. In certain embodiments there is more than one hold period (e.g., at least 2, at least 3, at least 4, at least 5 hold periods).

In some variations of the methods the constant pressure after an initial stepwise reduction may be at a hydrostatic pressure of from about 500 bar to about 5000 bar, from about 500 bar to about 4000 bar, from about 500 bar to about 2000 bar, from about 1000 bar to about 4000 bar, from about 1000 bar to about 3000 bar, from about 1000 bar to about 2000 bar, from about 1500 bar to about 4000 bar, from about 1500 bar to about 3000 bar, from about 2000 bar to about 4000 bar, or from about 2000 bar to about 3000 bar.

In particular variations, constant pressure after the stepwise reduction is from about four-fifths of the pressure immediately prior to the stepwise pressure reduction to about one-tenth of prior to the stepwise pressure reduction. For example, constant pressure is at a pressure of from about four-fifths to about one-fifth, from about two-thirds to about one-tenth, from about two-thirds to about one-fifth, from about two-thirds to about one-third, about one-half, or about one-quarter of the pressure immediately prior to the stepwise pressure reduction. Where there is more than one stepwise pressure reduction step, the pressure referred to is the pressure immediately before the last pressure reduction (e.g., where 2000 bar is reduced to 1000 bar is reduced to 500 bar, the pressure of 500 bar is one-half of the pressure immediately preceding the previous reduction (1000 bar)).

Where the pressure is reduced in a stepwise manner, the rate of pressure reduction (e.g., the period of pressure reduction prior to and after the hold period) may be in the same range as that rate of pressure reduction described for continuous reduction (e.g., in a non-stepwise manner). In essence, stepwise pressure reduction is the reduction of pressure in a continuous manner to an intermediate constant pressure, followed by a hold period and then a further reduction of pressure in a continuous manner. The periods of continuous pressure reduction prior to and after each hold period may be the same continuous rate for each period of continuous pressure reduction or each period may have a different reduction rate. In some variations, there are two periods of continuous pressure reduction and a hold period. In certain embodiments, each continuous pressure reduction period has the same rate of pressure reduction. In other embodiments, each period has a different rate of pressure reduction. In particular embodiments, the hold period is from about 8 to about 24 hours. In some embodiments, the hold period is from about 12 to about 18 hours. In particular embodiments, the hold period is about 16 hours.

The methods described herein may also include a further step (e.g., step (c)) of purifying the target polypeptide. Most usually, purification will be performed after step (b) and at atmospheric pressure; however, it is possible to perform some purification methods, in particular dialysis and/or solution exchange prior to step (b). Dialysis and/or solution exchange may also be performed during step b. For example, during a hold period and/or during a period of depressurization (including where depressurization is continuous and no hold period is applied).

A wide variety of techniques are known in the art for protein separation and purification, such as affinity chromatography, high-pressure liquid chromatography (HPLC), dialysis, solution exchange, ion exchange chromatography, size exclusion chromatography, reverse-phase chromatography, ammonium sulfate precipitation, or electrophoresis. Several conditions for HPLC can be varied for enhancing separation, such as the stationary and mobile phases. HPLC can be used with ion-exchange columns, reverse-phase columns, affinity columns, size-exclusion columns, and other types of columns. FPLC, or "Fast Performance Liquid Chromatography," can also be used. Gel-filtration chromatography can be used at low solvent pressures.

As used in this context, "purification" refers to the reduction of components present in the mixture other than the target polypeptide (and, optionally, where a binding partner (e.g., co-factor, etc) is present, the binding partner may not be removed). In some embodiments, the reduction is 5%, 10%, 15%, 20%, 25%, 30%, 40%, 50%, 60%, 70%, 80%, 90%, or 100% removal of the non-target polypeptide components.

Reaction Conditions

Optimization of Reaction Conditions

The optimum conditions for solubilization/proteolytic cleavage/refolding in the context of the methods described herein are a function of the characteristics of both the target polypeptide and the protease. In standard optimization experiments, the influence of pressure, pH, temperature, ionic strength, surfactants, chaotropes, stabilizing agents, and refolding time on the cleavage of the fusion partner and refolding should be tested. Once the key process parameters are identified, a central composite design can be used to optimize the appropriate conditions for each parameter. Guidance regarding typical ranges for the various parameters is provided in more detail below.

Initial studies can be conducted to screen the effect of solution conditions, solution pH, redox environment, and high pressure treatment on the solubilization and cleavage of target polypeptide inclusion bodies. Screening studies are typically conducted, but not limited to, empirical screens that examine step-wise the effect of processing conditions on yields. Synergistic effects between different parameters are not examined in these screening studies. Exemplary screening studies that can be conducted are as described for the cases of recombinant placental bikunin, recombinant growth hormone, and malaria pfs48 (see e.g., Seefeldt et al., 2004, St. John, 2001 et al., Seefeldt (2005), the disclosures of which are herein incorporated by reference in their entirety, particularly with respect to the screening studies described therein). High pressure refolding studies of bikunin and growth hormone demonstrate the step-wise screening process for solution conditions (pH 5-9), temperature (0-60° C.), ionic strength (0-160 mM NaCl), non-denaturing concentrations of chaotropes ((0-1M urea or 0-2M guanidine) and refolding time (0-24 hours). Studies can be conducted at about 2000 bar, about 2100 bar, about 2150 bar, etc. and compared to samples treated at atmospheric pressure. Other parameters, including those described herein, that can be screened include, but are not limited to, the presence and amount of stabilizing agents, surfactants, salts, as described herein. It should be noted that statistical analysis of variance (ANOVA's) can be used to rapidly screen which solution parameters affect solubilization and cleavage yields. In addition to the teaching provided herein, U.S. 2004/0038333, Seefeldt et al., 2004, St. John et al., (2002) (incorporated herein by reference in their entirety) also provide guidance regarding empirical screening procedures for determining the optimal solubilization and refolding conditions.

In this manner, the skilled artisan can determine the effect of processing conditions on the refolding of protein aggregates through the use of high pressure. It has been shown in literature that refolding reactions can have interactions between the process conditions, which prevents single-variable screening from effectively optimizing the process. For instance, pH affects protein conformation stability, protein colloidal stability, and disulfide bond formation kinetics. To effectively optimize the effect of pH, or any other process parameter, studies need to be conducted to account for interactions. In these instances, statistical experimental designs need to be employed. As described herein, solubilization is also examined as a function of urea, by step-wise analysis in a range from 0-4.5M urea at pH 8.0. The effect of reduced and oxidized disulfide shuffling agents is screened step-wise as a function of reduced/oxidized ratio while arbitrarily setting the pH to 8.0, urea concentration to 1.5M, and protein concentration. Once the significant parameters are identified, a face-centered statistical designed experiment is used to optimize the refolding conditions, taking into account interactions.

After initial optimization studies are performed for the fusion protein of interest, more granular optimization can be used to determined the optimal conditions for performing the solubilization/cleavage and, optionally, refolding processes. This process can generally be described as an experimental optimization that takes into account synergistic interactions between the critical parameters identified in the initial step-wise studies. An effective method for conducting these studies involves using a three or five level central composite statistical analysis, which takes into account interactions between the reaction parameters while minimizing the required number of experiments.

Another useful aid for optimizing conditions and/or monitoring solubilization/cleavage/refolding is in situ spectroscopic measurement of samples under pressure. This is a well-known process for examining polypeptide stability under pressure, but it has been underutilized in protein aggregation studies. Using high pressure spectroscopic techniques to observe aggregates dissolve under pressure will help determine the optimal pressure ranges for recovering proteins from aggregates. Custom made high pressure cells have been routinely used for high pressure unfolding studies and can be adapted for use in high pressure disaggregation and refolding. Additional guidance for the skilled artisan may also be found in Paladini and Weber 1981 and Seefeldt et al. 2004, incorporated by reference herein in their entirety.

Methods that can be employed to monitor the optimization of various parameters include Fourier Transform Infrared Spectroscopy (FTIR), circular dichroism (CD) spectroscopy (far and/or near UV), UV spectroscopy, measurement of total protein concentrations (e.g., BCA assay method (Pierce Chemical Co., Rockford, Ill.), etc), activity assays to measure the activity of the target polypeptide, electrophoretic gels with molecular weight markers to visualize the appearance of fusion partner and target polypeptide under various conditions, HPLC analysis of soluble polypeptide fractions. etc.

Suitable devices for performing high pressure spectroscopy can be obtained commercially (e.g., such as fluorescence cells available from ISS Inc., Champaign, Ill. or fluorescence/ultraviolet absorbance cells available from BaroFold Inc., Boulder, Colo.) or can be fabricated by the skilled artisan. For example, Randolph et al., (U.S. Patent Application Publication No. 2004/0038333, incorporated by reference herein in its entirety) described a high-pressure W spectroscopy cell made of stainless steel, sealed with Btma-N 90 durometer O-rings and had an optical port diameter of 6 mm and pathlength of 7.65 mm. The cell utilized cylindrical sapphire windows (16 mm diameter, 5.1 mm thick) and was capable of experiments up to 250 MPa. Separation of the sample from the pressure transmitting fluid was facilitated by a piston device external to the cell.

Hydrostatic Pressure

"Increased hydrostatic pressure," for the purposes of dissociating fusion protein aggregates includes hydrostatic pressures of from about 500 bar to about 10,000 bar.

In some embodiments, the increased hydrostatic pressure may be from about 500 bar to about 5000 bar, from about 500 bar to about 4000 bar, from about 500 bar to about 2000 bar, from about 500 bar to about 2500 bar, from about 500 bar to about 3000 bar, from about 500 bar to about 6000 bar, from about 1000 bar to about 5000 bar, from about 1000 bar to about 4000 bar, from about 1000 bar to about 2000 bar, from about 1000 bar to about 2500 bar, from about 1000 bar to about 3000 bar, from about 1000 bar to about 6000 bar, from about 1500 bar to about 5000 bar, from about 1500 bar to about 3000 bar, from about 1500 bar to about 4000 bar, from about 1500 bar to about 2000 bar, from about 2000 bar to about 5000 bar, from about 2000 bar to about 4000 bar, from about 2000 bar to about 3000 bar, or about 1000 bar, about 1500 bar, about 2000 bar, about 2500 bar, about 3000 bar, about 3500 bar, about 4000 bar, about 5000 bar, about 6000 bar, about 7000 bar, about 8000 bar, about 9000 bar.

In some variations of the methods, for example, where a further period of increased pressure is performed (e.g., step (a-1) and other variations), it can be advantageous to have a lower range of increased pressure to facilitate refolding of the target polypeptide produced by the solubilization and cleavage processes (e.g., step (a)). Typical ranges for increased pressure used to facilitate refolding include, for example, from about 500 bar to about 3500 bar. Thus in some embodiments, the further period of increased hydrostatic pressure may be performed at hydrostatic pressures of from about 500 bar to about 3500 bar, from about 500 bar to about 3000 bar, from about 500 bar to about 2000 bar, from about 500 bar to about 2500 bar, from about 1000 bar to about 3500 bar, from about 1000 bar to about 3000 bar, from about 1000 bar to about 2000 bar, from about 1000 bar to about 2500 bar, from about 1000 bar to about 1500 bar, from about 1500 bar to about 3500 bar, from about 1500 bar to about 3000 bar, from about 1500 bar to about 2000 bar, or about 500 bar, about 1000 bar, about 1500 bar, about 2000 bar, about 2500 bar, about 3000 bar, about 3500 bar.

"Atmospheric," "ambient," or "standard" pressure is defined as approximately 15 pounds per square inch (psi) or approximately 1 bar or approximately 100,000 Pascals.

pH and Ionic Strength

The methods described herein can be performed at a range of pH values, depending on the particular fusion protein, target polypeptide and protease selected. The optimal pH, in concert with other factors, can be optimized as described herein. The pH should be selected to favor the native-conformation of the target polypeptide and protease (e.g., such that sufficient proteolytic activity is retained).

In certain embodiments the pH of the mixture is from about pH 4 to about pH 12. In some embodiments, the pH range is from about pH 4 to about pH 11.5, from about pH 4 to about pH 1, from about pH 4 to about pH 10.5, from about pH 4 to about pH 10, from about pH 4 to about pH 9.5, from about pH 4 to about pH 8.5, from about pH 4 to about pH 7, from about pH 5 to about pH 9.5, from about pH 5 to about pH 9, from about pH 5 to about pH 8.5, from about pH 6 to about pH 10, from about pH 6 to about pH 9.5, from about pH 6 to about pH 9, from about pH 6 to about pH 8.5, from about pH 7 to about pH 9, from about pH 7 to about pH 8.5, from about pH 7 to about pH 10, from about pH 7 to about pH 9.5, from about pH 7 to about pH 9, from about pH 8 to about pH 9, from about pH 8 to about pH 9.5. In some embodiments, the pH is from about pH 7 to about pH 9. In certain embodiments, the pH is from about pH 7 to about pH 10, from about pH 7 to about pH 11.

When the method additionally includes the use of disulphide shuffling agent pairs, the optimal pH is often around about pH 7 to about pH 10 or pH 7 to about pH 9.5. pH values in this range appear to facilitate the ability of the shuffling reagents to catalyze the breakage/reformation of strained disulfide bonds in order to facilitate formation of the native disulfide bonding pattern.

Similarly, if the protease or target polypeptide contains free cysteines (where disulfide bonds are not present in the native conformation), then the pH should be sufficient for any reducing agent included in the mixture to maintain the cysteines in a non-disulfide bonded form. In these cases, pH values of 4-12 are often advantageous.

Typical ionic strengths are from about 0 to about 2 M. In some embodiments the ionic strength may be about 1 M, about 1.5 M, about 0.75 M, about 0.5 M, about 400 mM, about 300 mM, about 150 mM, about 200 mM, about 250 mM, about 50 mM, about 10 mM NaCl equivalent. In some embodiments the ionic strength may be about 10 mM, about 100 mM, about 150 mM, about 200 mM, about 250 mM NaCl equivalent. In certain embodiments, the ionic strength may be from about 0 to about 1 M, from about 0 to about 2 M, from about 0 to about 0.5 M, from about 0 to about 400 mM, from about 0 to about 300 mM, from about 0 to about 250 mM, from about 0 to about 200 mM, from about 0 to about 100 mM, from about 0 to about 50 mM, from about 50 to about 1 M, from about 50 to about 2 M, from about 50 to about 0.5 M, from about 50 to about 400 mM, from about 50 to about 300 mM, from about 50 to about 250 mM, from about 50 to about 200 mM, from about 50 to about 100 mM, or from about 50 to about 50 mM NaCl equivalent.

Various salts may be used to adjust the ionicity, such as NaCl, KCl, lithium chloride, sodium sulfate, barium sulfate, magnesium chloride, magnesium sulfate, manganese sulfate, iron sulfate, and phosphate ions.

Ionic strength should take into account sensitivity of the protease and the target polypeptide to electrostatic shielding. The optimum ionic strength can be determined as described herein and can be varied using reagents known to the skilled artisan.

Temperature

The methods described herein can be performed at a range of temperature values, depending on the particular fusion protein, target polypeptide and protease selected. The optimal temperature, in concert with other factors, can be optimized as described herein.

In some embodiments of the methods, the temperature can range from about 0° C. to about 100° C. without adversely affecting the fusion protein, target polypeptide and protease, provided that prior to return to room temperature, the mixture is brought to a temperature at which it will not freeze.

Thus in certain embodiments, the temperature may be from about 0° C. to about 75° C., from about 0° C. to about 55° C., from about 0° C. to about 35° C., from about 0° C. to about 25° C., from about 20° C. to about 75° C., from about 20° C. to about 65° C., from about 20° C. to about 35° C., from about 20° C. to about 25° C.

Although increased temperatures are often used to cause aggregation of proteins, when coupled with increased hydrostatic pressure it has been found that increased temperatures can enhance refolding recoveries effected by high pressure treatment, provided that the temperatures are not so high as to cause irreversible denaturation. Generally, the increased temperature for refolding should be about 20° C. lower than the temperatures at which irreversible loss of activity occurs. Relatively high temperatures (for example, about 60° C. to about 125° C., about 80° C. to about 110° C., including about 100° C., about 105° C., about 110° C., about 115° C., about 120° C. and about 125° C.) may be used while the solution is under pressure, as long as the 25 temperature is reduced to a suitably low temperature before Repressurizing, Such a suitably low temperature is defined as one below which thermally-induced denaturation or aggregation occurs at atmospheric conditions.

Reagents

Reducing Agents

As mentioned previously, in some variations of the methods it is advantageous to include a reducing agent. This is particular the case where the protease or the target polypeptide incorporate cysteine residues that are not disulfide bonded in the native state. This is particular true for cysteine proteases, which are so named because they incorporate a cysteine residue in their active sites.

A wide range of reducing agents can be used (for example diothiothreitol, glutathione, dithioerythritol, tris(2-carboxyethyl)phosphine hydrochloride, or β-mercaptoethanol, etc.). The proper reducing agent should be selected to enable activity of the required protease. For example, in the case of a cysteine protease, DTT is used to maintain activity of the protease.

While the concentration of the reducing agent will vary with the target polypeptide and/or protease selected for use, in general there should be an excess of reducing agent compared to the number/molar amount of cysteine residues present in the mixture to provide an amount of reducing agent sufficient to maintain proteolytic activity of the protease and/or disfavor the formation of non-disulfide bonds in the target polypeptide (if cysteine residues are present).

Ligands for Use in Refolding

Various ligands can be used in refolding of proteins. Such ligands include, but are not limited to, antibodies, receptors, peptides, peptidomimetics, vitamins, cofactors, prosthetic groups, substrates, products, competitive inhibitors, metals and other small or large molecules.

One particular group of ligands useful in the invention is the group of small organic molecules. Small organic molecules in turn may be divided into two types: rigid small organic molecules and flexible small organic molecules. A rigid molecule typically has one predominant conformation in solution; a rigid molecule is defined as having greater than about 50%, greater than about 75%, or greater than about 90% of the molecules in solution present in a single conformation. A flexible molecule has multiple solution conformations, where a single conformation accounts for no more than about 50%, no more than about 25%, or no more than about 10% of the molecules in solution. These conformational populations are preferably measured in aqueous solution, more preferably in the refolding buffer to be used for the protein(s) of interest. A variety of methods can be used to define different conformations of a molecule for the purposes of the foregoing conditions. Experimental methods include, but are not limited to, detection of different conformations by nuclear magnetic resonance spectra (conformations that interconvert slowly on the NMR time scale can be detected by NMR, although rapidly exchanging conformations typically cannot be detected by ordinary NMR experiments), fluorescence spectroscopy, or other spectroscopic methods. Computational methods include, but are not limited to, molecular mechanics and molecular dynamics simulations where molecules display different conformations (e.g., conformations with root-mean-square deviations differing by 1, 2, 3, or 4 Angstroms, or conformations with differences of 0.25, 0.5, 0.75, 1, 2, 3, 4, or 5 kcal in free energy).

Antibodies raised against a specific protein target of interest can also be used during high-pressure refolding of proteins of interest. Antibodies can be of either polyclonal or monoclonal origin. In some instances, polyclonal antibodies will be useful, e.g., for providing antibodies which bind to distinct epitopes on the same protein and/or distinct antibodies binding to the same epitope on the protein, in order to provide multiple folding "guidance," while in other instances, monoclonal antibodies will be useful, e.g. for preparation of well-characterized folding conditions. Either intact antibodies or antibody fragments which retain the antigen-binding properties of the intact antibody can be used. Such antibody fragments include Fab fragments, F(ab')2 fragments, Fd fragments, Fv fragments, dAb (single domain) fragments (Ward et al., Nature 341:544 (1989)); isolated complementarity determining regions retaining specific-antigen binding activity; and scFv (recombinantly-produced single chain Fv) fragments.

Ligands can also include other co-factors of the target polypeptide needed to form or maintain the native confirmation. For example, metal ions, substrate, etc.

The ligands may be added to the mixture prior to, during or after step (a). Additionally, they may also be added after step (b). Addition of the ligand is as described for the addition of the disulfide shuffling agent pair with respect to addition at various pressures.

In some variations, the ligand is added prior to step (a). In certain embodiments, the ligand is added prior to step (b). In particular embodiments, the ligand is added after step (b). In some embodiments, the ligand is added after during step (a). In particular embodiments, the ligand is added during to step (a-1). In certain of these embodiments, the ligand is a target polypeptide co-factor.

Protease Cleavage Buffer

In addition to the aqueous solution or suspension that is mixed with the protease and fusion protein aggregates, the mixture may also include a protease cleavage buffer. The protease cleavage buffer may contain one or more additional agents including: one or more stabilizing agents, one or more buffering agents, one or more surfactants, one or more disulfide shuffling agent pairs, one or more salts, one or more chaotropes, or combinations of two or more of the foregoing.

The amounts of the additional agents will vary depending on the selection of the fusion protein, protease and target polypeptide, however, the effect of the presence (and amount) or absence of each additional agent or combinations of agents can be determined and optimized using the teachings provided herein.

Exemplary additional agents include, but are not limited to, buffers (examples include, but are not limited to, phosphate buffer, borate buffer, carbonate buffer, citrate buffer, HEPES, MEPS, CHES, CAPS, etc.), salts (examples include, but are not limited to, the chloride, sulfate, and carbonate salts of sodium, zinc, calcium, ammonium and potassium), chaotropes (examples include, but are not limited to, urea, guanidine hydrochloride, guanidine sulfate and sarcosine), and stabilizing agents (e.g., preferential excluding compounds, etc.).

Stabilizing Agents

Non-specific protein stabilizing agents act to favor the most compact conformation of a protein. Such agents include, but are not limited to, one or more free amino acids, one or more preferentially excluding compounds, trimethylamine oxide, cyclodextrans, molecular chaperones, and combinations of two or more of the foregoing.

Amino acids can be used to prevent reaggregation and facilitate the dissociation of hydrogen bonds. Typical amino acids that can be used, but not limited to, are arginine, lysine, proline, glycine, histidine, and glutamine or combinations of two or more of the foregoing. In some embodiments, the free amino acid(s) is present in a concentration of about 0.1 mM to about the solubility limited of the amino acid. In some variations from about 0.1 mM to about 2 M. The optimal concentration is a function of the target polypeptide and should favor the native conformation.

Preferentially excluding compounds can be used to stabilize the native confirmation of both the protease and the target polypeptide of interest. Possible preferentially excluding compounds include, but are not limited to, sucrose, hexylene glycol, sugars (e.g., sucrose, trehalose, dextrose, mannose), and glycerol. The range of concentrations that can be use are from 0.1 mM to the maximum concentration at the solubility limit of the specific compound. The optimum preferential excluding concentration is a function of the target polypeptide and protease.

In particular embodiments, the preferentially excluding compound is one or more sugars (e.g., sucrose, trehalose, dextrose, mannose or combinations of two or more of the foregoing). In some embodiments, the sugar(s) is present in a concentration of about 0.1 mM to about the solubility limit of the particular compound. In some embodiments, the concentration is from about 0.1 mM to about 2M, from about 0.1 mM to about 1.5M, from about 0.1 mM to about 1M, from about 0.1 mM to about 0.5M, from about 0.1 mM to about 0.3M, from about 0.1 mM to about 0.2 M, from about 0.1 mM to about 0.1 mM, from about 0.1 mM to about 50 mM, from about 0.1 mM to about 25 mM, or from about 0.1 mM to about 10 mM.

In some embodiments, the stabilizing agent is one or more of sucrose, trehalose, glycerol, betaine, amino acid(s), or trimethylamine oxide.

In certain embodiments, the stabilizing agent is a cyclodextran. In some embodiments, the cyclodextran is present in a concentration of about 0.1 mM to about the solubility limit of the cyclodextran. In some variations from about 0.1 mM to about 2 M.

In certain embodiments, the stabilizing agent is a molecular chaperone. In some embodiments, the molecular chaperone is present in a concentration of about 0.01 mg/ml to 10 mg/ml.

A single stabilizing agent maybe be used or a combination of two or more stabilizing agents (e.g., at least two, at least three, or 2 or 3 or 4 stabilizing agents). Where more than one stabilizing agent is used, the stabilizing agents may be of different types, for example, at least one preferentially excluding compound and at least one free amino acid, at least one preferentially excluding compound and betaine, etc.

Buffering Agents

Buffering agents may be present to maintain a desired pH value or pH range. Numerous suitable buffering agents are known to the skilled artisan and should be selected based on the pH that favors the native conformation of both protease and the target polypeptide, or, at least does not disfavor the native conformation of either. Either inorganic or organic buffering agents may be used. Suitable concentrations are known to the skilled artisan and should be optimized for the methods as described herein according to the teaching provided based on the characteristics of the target polypeptide and protease.

Thus, in some embodiments, at least one inorganic buffering agent is used (e.g., phosphate, carbonate, etc.). In certain embodiments, at least one organic buffering agent is used (e.g., citrate, acetate, Tris, MOPS, MES, HEPES, CHES, CAPS, etc.) Additional organic and inorganic buffering agents are well known to the art.

In some embodiments, the one or more buffering agents is phosphate buffer, borate buffer, carbonate buffer, citrate buffer, HEPES, MEPS, MOPS, MES, CHES, CAPS, or acetate buffer.

In some embodiments, the one or more buffering agents are phosphate buffers, carbonate buffers, citrate, Tris, MOPS, MES, acetate, CHES, CAPS, or HEPES.

A single buffering agent maybe be used or a combination of two or more buffering agents (e.g., at least two, at least 3, or 2 or 3 or 4 buffering agents).

Surfactants

A "surfactant" as used in the present context is a surface active compound which reduces the surface tension of water.

Surfactants are used to improve the solubility of certain proteins. Surfactants should generally be used at concentrations above or below their critical micelle concentration (CMC). For example, from about 5% to about 20% above or below the CMC. However, these values will vary dependent upon the surfactant chosen, for example, surfactants such as, beta-octylgluco-pyranoside may be effective at lower concentrations than, for example, surfactants such as TWEEN-20 (polysorbate 20). The optimal concentration is a function of each surfactant, which has its own CMC.

Useful surfactants include nonionic (including, but not limited to, t-octylphenoxypolyethoxy-ethanol and polyoxyethylene sorbitan), anionic (e.g., sodium dodecyl sulfate) and cationic (e.g., cetylpyridinium chloride) and amphoteric agents. Suitable surfactants include, but are not limited to deoxycholate, sodium octyl sulfate, sodium tetradecyl sulfate, polyoxyethylene ethers, sodium cholate, octylthioglucopyranoside, n-octylglucopyranoside, alkyltrimethylammonium bromides, alkyltrimethyl ammonium chlorides, and sodium bis(2 ethylhexyl) sulfosuccinate. In some embodiments the surfactant may be polysorbate 80, polysorbate 20, sarcosyl, Triton X-100, β-octyl-gluco-pyranoside, or Brij 35.

In some embodiments the one or more surfactant may be a polysorbate, polyoxyethylene ether, alkyltrimethylammonium bromide, pyranosides or combination of two or more of the foregoing. In certain embodiments, the one or more surfactant may be β-octyl-gluco-pyranoside, Brij 35, or a polysorbate.

In certain embodiments the one or more surfactant may be octyl phenol ethoxylate, β-octyl-gluco-pyranoside, polyoxyethyleneglycol dodecyl ether, sarcosyl, sodium dodecyl sulfate, polyethoxysorbitan, deoxycholate, sodium octyl sulfate, sodium tetradecyl sulfate, sodium cholate, octylthioglucopyranoside, n-octylglucopyranoside, sodium bis(2-ethylhexyl) sulfosuccinate or combinations of two or more of the foregoing.

A single surfactant maybe be used or a combination of two or more surfactants (e.g., at least two, at least 3, or 2 or 3 or 4 surfactants).

Disulfide Shuffling Agent Pairs

Where the target polypeptide contains disulfide bonds in the native conformation it is generally advantageous to include at least one disulfide shuffling agent pair in the mixture. The disulfide shuffling agent pair facilitates the breakage of strained non-native disulfide bonds and the reformation of native-disulfide bonds.

In general, the disulfide shuffling agent pair includes a reducing agent and an oxidizing agent. Exemplary oxidizing agents oxidized glutathione, cystine, cystamine, molecular oxygen, iodosobenzoic acid, sulfatalysis and peroxides. Exemplary reducing agents include glutathione, cysteine, cysteamine, diothiothreitol, dithioerythritol, tris(2-carboxyethyl)phosphine hydrochloride, or β-mercaptoethanol.

Exemplary disulfide shuffling agent pairs include oxidized/reduced glutathione, cystamine/cysteamine, and cystine/cysteine.

Additional disulfide shuffling agent pairs are described by Gilbert (Gilbert 1990; Gilbert 1995), which are hereby incorporated by reference in their entirety.

The selection and concentration of the disulfide shuffling agent pair will depend upon the characteristics of the target polypeptide and, where the disulfide shuffling agent pair is added prior to cleavage, protease that is present. Typically, concentration of the disulfide shuffling agent pair taken together (including both oxidizing and reducing agent) is from about 0.1 mM to about 100 mM of the equivalent oxidized thiol, however, the concentration of the disulfide shuffling agent pair should be adjusted such that the presence of the pair is not the rate limiting step in disulfide bond rearrangement.

In some embodiments, the concentration will be about 1 mM, about 2 mM, about 3 mM about 5 mM, about 8 mM, about 9 mM, about 10 mM, about 20 mM, about 30 mM, about 40 mM, about 50 mM, about 60 mM, about 70 mM, about 80 mM, about 90 mM, about 100 mM, or from about 80 mM to about 100 mM, from about 0.1 mM to about 20 mM, from about 10 mM to about 50 mM, from about 1 mM to about 100 mM, from about 50 mM to about 100 mM, from about 20 mM to about 100 mM, from about 0.1 mM to about 10 mM, from about 0.1 mM to about 8 mM; from about 0.1 mM to about 6 mM, from about 0.1 mM to about 7 mM, from about 0.1 mM to about 5 mM, from about 0.1 mM to about 3 mM, from about 0.1 mM to about 1 mM.

A single disulfide shuffling agent pair maybe be used or a combination of two or more disulfide shuffling agent pairs (e.g., at least two, at least 3, or 2 or 3 or 4 disulfide shuffling agent pairs).

Chaotropes

Chaotropic agents (also referred to as a "chaotrope") are compounds, including, without limitation, guanidine, guanidine hydrochloride (guanidinium hydrochloride, GdmHCl), guanidine sulfate, urea, sodium thiocyanate, and/or other compounds which disrupt the noncovalent intermolecular bonding within the protein, permitting the polypeptide chain to assume a substantially random conformation Chaotropic agents may be used in concentration of from about 10 mM to about 8 M. The optimal concentration of the chaotropic agent will depend on the components of the system (e.g., fusion protein aggregate, protease, target polypeptide) as well as on the particular chaotropes selected. The choice of particular chaotropic agent and determination of optimal concentration can be optimized by the skilled artisan in view of the teachings provided herein.

In some embodiments, the concentration of the chaotropic agent will be, for example, from about 10 mM to about 8 M, from about 10 mM to about 7 M, from about 10 mM to about 6 M, from about 0.1 M to about 8 M, from about 0.1 M to about 7 M, from about 0.1 M to about 6 M, from about 0.1 M to about 5 M, from about 0.1 M to about 4 M, from about 0.1 M to about 3 M, from about 0.1 M to about 2 M, from about 0.1 M to about 1 M, from about 10 mM to about 4 M, from about 10 mM to about 3 M, from about 10 mM to about 2 M, from about 10 mM to about 1 M, or about, 10 mM, about 50 mM, about 75 mM, about 0.1 M, about 0.5 M, about 0.8 M, about 1 M, about 2 M, about 3 M, about 4 M, about 5 M, about 6 M, about 7 M, about 8 M.

When used in the present methods, it is often advantageous to use chaotropic agents in non-denaturing concentrations to facilitate the dissociation of hydrogen bonds. While a non-denaturing concentration will vary depending on the protease and the target polypeptide, the range of non-denaturing concentrations is typically from about 0.1 to about 4 M. In some embodiments the concentration is from about 0.1 M to about 2 M.

In certain embodiments, guanidine hydrochloride or urea are the chaotropic agents.

A single chaotropic agent maybe be used or a combination of two or more chaotropic agents (e.g., at least two, at least 3, or 2 or 3 or 4 chaotropic agents).

High Pressure Devices and Materials

Commercially available high pressure devices and reaction vessels, such as those described in the examples, may be used to achieve the hydrostatic pressures in accordance with the methods described herein (see BaroFold Inc., Boulder Co.). Additionally devices, vessels and other materials for carrying out the methods described herein, as well as guidance regarding the performing increased pressure methods, are described in detail in U.S. Pat. No. 6,489,450, which is incorporated herein in its entirety. The skilled artisan is particularly directed to column 9, lines 39-62 and Examples 2-4. International Pat. App. Pub. No. WO 02/062827, incorporated herein in its entirety, also provides the skilled artisan with detailed teachings regarding devices and use thereof for high hydrostatic pressure solubilization of aggregates throughout the specification. Particular devices and teachings regarding the use of high pressure devices is also provided in U.S. pat. app. Ser. No. 60/739,094, which is hereby incorporated by reference in its entirety.

Multiple-well sample holders, such as those described herein, may be used and can be conveniently sealed using self-adhesive plastic covers. The containers, or the entire multiple-well sample holder, may then be placed in a pressure vessel, such as those commercially available from the Flow International Corp. or High Pressure Equipment Co. The remainder of the interior volume of the high-pressure vessel may than be filled with water or other pressure transmitting fluid.

Mechanically, there are two primary methods of high-pressure processing: batch and continuous. Batch processes simply involve filling a specified chamber, pressurizing the chamber for a period of time, and repressurizing the batch. In contrast, continuous processes constantly feed aggregates into a pressure chamber and soluble, refolded proteins move out of the pressure chamber. In both set ups, good temperature and pressure control is essential, as fluctuations in these parameters can cause inconsistencies in yields. Both temperature and pressure should be measured inside the pressure chamber and properly controlled.

There are many methods for handling batch samples depending upon the specific stability issues of each target polypeptide and protease. Samples can be loaded directly into a pressure chamber, in which case the aqueous solution and/or suspension would be used as the pressure medium.

Alternately, samples can be loaded into any variety of sealed, flexible containers, including those described herein. This allows for greater flexibility in the pressure medium, as well as the surfaces to which the mixture is exposed. Sample vessels could conceivably even act to protect the target polypeptide from chemical degradation (e.g., oxygen scavenging plastics are available).

With continuous processing, scale-up is simple. Small volumes under pressure can be used to refold large volumes the sample mixture. In addition, using an appropriate filter on the outlet of a continuous process will selectively release soluble target polypeptide from the chamber while retaining both soluble and insoluble aggregates.

Pressurization is a process of increasing the pressure (usually from atmospheric or ambient pressure) to a higher pressure. Pressurization takes place over a predetermined period of time, ranging from 0.1 second to 10 hours. Such times include 1 second, 2 seconds, 5 seconds, 10 seconds, 20 seconds, 1 minute, 2 minutes, 5 minutes, 10 minutes, 30 minutes, 60 minutes, 2 hours, 3 hours, 4 hours, and 5 hours.

Repressurization is a process of decreasing the pressure, from a high pressure, to a lower pressure (usually atmospheric or ambient pressure). Depressurization takes place over a predetermined period of time, ranging from 10 seconds to 10 hours, and may be interrupted at one or more points to permit optimal refolding at intermediate (but still increased compared to ambient) pressure levels. The repressurization or interruptions may be 1 second, 2 seconds, 5 seconds, 10 seconds, 20 seconds, 1 minute, 2 minutes, 5 minutes, 10 minutes, 30 minutes, 60 minutes, 2 hours, 3 hours, 4 hours, and 5 hours.

Degassing is the removal of gases dissolved in solutions and is often advantageous in the practice of the methods described herein. Gas is much more soluble in liquids at high pressure as compared to atmospheric pressure and, consequently, any gas headspace in a sample will be driven into solution upon pressurization. The consequences are two-fold: the additional oxygen in solution may chemically degrade the protein product, and gas exiting solution upon repressurization may cause additional aggregation. Thus, samples should be prepared with degassed solutions and all headspace should be filled with liquid prior to pressurization.

By "high pressure" is meant a pressure of at least about 250 bar. The pressure at which the devices described herein are used can be at least about 250 bar of pressure, at least about 400 bar of pressure, at least about 500 bar of pressure, at least about 1 kbar of pressure, at least about 2 kbar of pressure, at least about 3 kbar of pressure, or at least about 5 kbar of pressure.

By "closed system" is meant the standard chemical thermodynamic term referring to a system where matter cannot be transferred between the system and its surroundings; however, transfer of mechanical or heat energy can occur between a closed system and its surroundings. In contrast, an "open system" permits transfer of matter and/or mechanical or heat energy between the system and its surroundings. An "isolated system" is a closed system that does not permit either mechanical or thermal contact with its surroundings, i.e., no transfer of mechanical or heat energy takes place to or from an isolated system. A "substantially closed system" is a system where less than about 1%, more preferably less than about 0.5%, more preferably less than about 0.2%, more preferably less than about 0.1%, more preferably less than about 0.05%, still more preferably less than about 0.01% of the mass of the sample can be transferred between the system and its surroundings.

By "significant transfer of liquid sample" is meant a transfer of about 1% or more of the volume of liquid contained in a sample (measured at standard atmospheric pressure). When devices of the invention are designed to prevent significant transfer of liquid sample, the amount of sample transferred during the use of the device is less than about 1%, more preferably less than about 0.5%, more preferably less than about 0.2%, more preferably less than about 0.1%, more preferably less than about 0.05%, still more preferably less than about 0.01% of the unpressurized volume of the sample.

By "substantially impermeable to oxygen at high pressure," "substantially oxygen-impermeable at high pressure," or "substantially impermeable to oxygen mass transfer at high pressure" is meant a material that permits a change in oxygen concentration due to oxygen mass transfer across the material of no more than about 0.3 mM in the sample during the duration of the high pressure treatment. In another embodiment, the material permits a change in oxygen concentration due to oxygen mass transfer across the material of not more than about 0.2 mM, preferably not more than about 0.1 mM, preferably not more than about 0.05 mM, more preferably not more than about 0.025 mM, still more preferably not more than about 0.01 mM, in the sample during the duration of the high pressure treatment. In percentage terms, the material permits a change in oxygen concentration in the sample due to oxygen mass transfer across the material of no more than about 10%, preferably no more than about 5%, more preferably no more than about 2.5%, still more preferably no more than about 1%, of the initial oxygen content of the sample during the duration of the high pressure treatment.

Materials for High-Pressure Devices

The body of the high-pressure devices (containers) can be fabricated from a wide variety of materials. These materials should be flexible to enable pressure transfer. Suitable materials should not break, fracture, or otherwise undergo any failure or loss of integrity under high pressure treatment which would permit leakage of samples either from one or more sample compartments to the external surroundings, or which would permit leakage of samples between sample compartments. Such leakage, of course, is not meant to include intentional transfers between one or more sample compartments and the external surroundings, or intentional transfers between two or more sample compartments or other compartments, which are deliberately desired by the artisan.

The device must be constructed with a material that can withstand at least about 250 bar of pressure and still maintain integrity. In another embodiment, the material can withstand at least about 500 bar of pressure and still maintain integrity. In another embodiment, the material can withstand at least about 1 kbar of pressure and still maintain integrity. In another embodiment, the material can withstand at least about 2 kbar of pressure and still maintain integrity. In another embodiment, the material can withstand at least about 3 kbar of pressure and still maintain integrity. In another embodiment, the material can withstand at least 5 kbar of pressure and still maintain integrity. The specified pressures are multi-dimensional pressure on the device, not a "pressure drop" across the device.

The material used should also permit pressure transfer from the surroundings to the sample compartments, so that the pressure across the device is roughly equivalent; that is, the difference in pressure experienced by any two locations within the device is no more than about 1%, preferably no more than about 0.5%, more preferably no more than about 0.1%, of the total pressure. In other embodiments, the absolute difference in pressure experienced by any two locations within the device is less than about 5 bar, preferably less than about 2 bar, more preferably less than about 1 bar. Any difference between the external applied pressure and any interior portion of the device is no more than about 5%, preferably no more than about 2%, more preferably no more than about 1%, still more preferably no more than about 0.5%, yet more preferably no more than about 0.1%, of the total applied external pressure. Therefore, the material should be flexible in order to transmit pressure.

In one embodiment, the materials are polymers. In another embodiment, the polymeric materials can be injection molded for inexpensive mass production. Suitable polymeric materials include polyethyleneterephthalate, high-density polyethylene, and polystyrene. Other polymeric materials which can withstand high-pressure treatment, but which are not necessarily oxygen impermeable, include low-density polyethylene, polypropylene, and polycarbonate.

Considerations of Oxygen Content of Sample

Many reactions, such as refolding of cysteine-containing proteins, can be affected by the oxygen content of the sample. Typically a protein refolding experiment will entail use of a specified concentration of redox reagents such as thiols (e.g., glutathione). The concentration of oxygen in a sample can be affected by the presence of air bubbles in a sample, as air bubbles will be forced into solution at high pressures, changing the $O_2$ concentration in the sample. The concentration of oxygen in a sample can also be affected by diffusion of oxygen across the walls of the device. The sample device will typically be placed in a chamber to which pressure is applied; if the fluid used in the chamber is water, then oxygen dissolved in the chamber's water surrounding the sample device can diffuse across the walls of the device.

These considerations are addressed in the following sections, "oxygen concentration changes due to air bubbles," and "oxygen permeability at high pressure."

Oxygen Concentration Changes Due to Air Bubbles

It is estimated that about 80% of the variation in oxygen concentration will arise from air bubbles in the sample, while about 20% of the variation will arise from oxygen diffusion across the walls of a syringe-type device. This underscores the importance of removing as many air bubbles as possible from the sample vial. For every 25 µl of air in a 1 ml sample, 0.2 mmoles $O_2$ is loaded, as high pressure will dissolve the air into the liquid sample; that amount of oxygen will react with 0.8 mM reduced thiol. Typical reduced thiol concentrations range from about 1 mM to about 10 mM (Clark E. D., "Protein refolding for industrial processes," Curr. Opin. Biotechnol. 12:202-207 (2001)), and over this range a 0.8 mM change in reduced thiol concentration will cause a variation in concentration of from about 8% to about 80%. At a typical concentration of 4 mM reduced thiol, a 0.8 mM reduction of reduced thiol results in about a 20% change in solution concentration of reduced thiols. This underscores the importance of removing all air bubbles, which is difficult to accomplish with current state-of-the-art vials and which the instant invention is designed to address.

Figure 12:
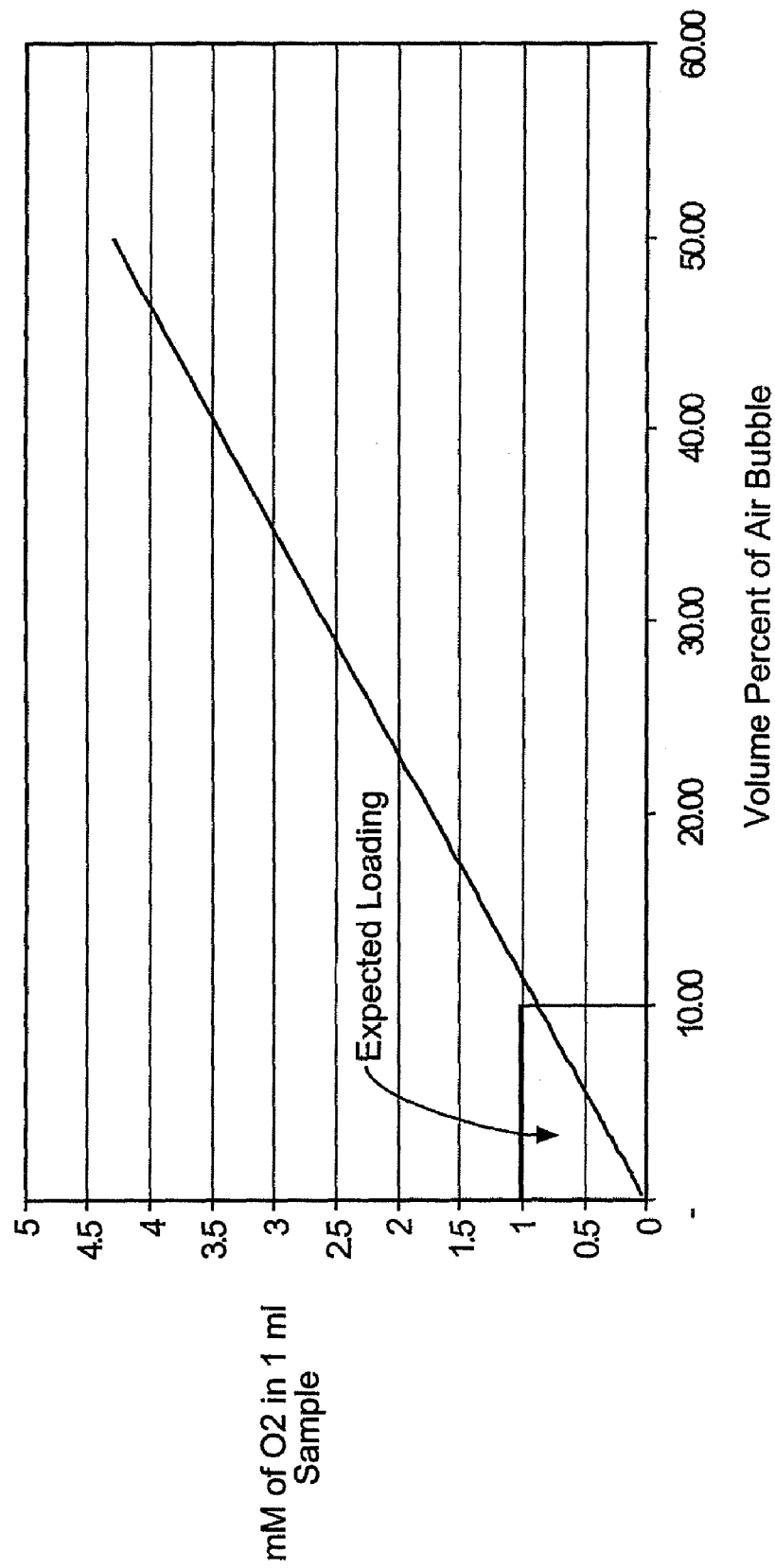
FIG. 12 depicts the amount of oxygen loaded in a sample containing an air bubble as a function of the bubble size in the sample, where the bubble size is calculated as the volume percent of the sample.

FIG. 12 shows the oxygen loading caused by air bubbles of various sizes. The volume percent of air bubbles should be kept as low as possible, to no more than about 10% of the sample volume, more preferably no more than about 5% of the sample volume, still more preferably no more than about 2.5% of the sample volume, yet more preferably no more than about 1% of the sample volume.

Oxygen Permeability at High Pressure

The materials used in the devices should be substantially impermeable to oxygen mass transfer at high pressure. Optionally, the materials used are also substantially impermeable to transfer of other gases at high pressure, such as carbon dioxide. Materials which are substantially impermeable to oxygen mass transfer at high pressure include, but are not limited to, polyethylene-terephthalate (PET), Mylar® (Mylar is a registered trademark of DuPont, designating a biaxially-oriented polyethylene terephthalate polyester film), high-density polyethylene, and polystyrene.

Figure 10:
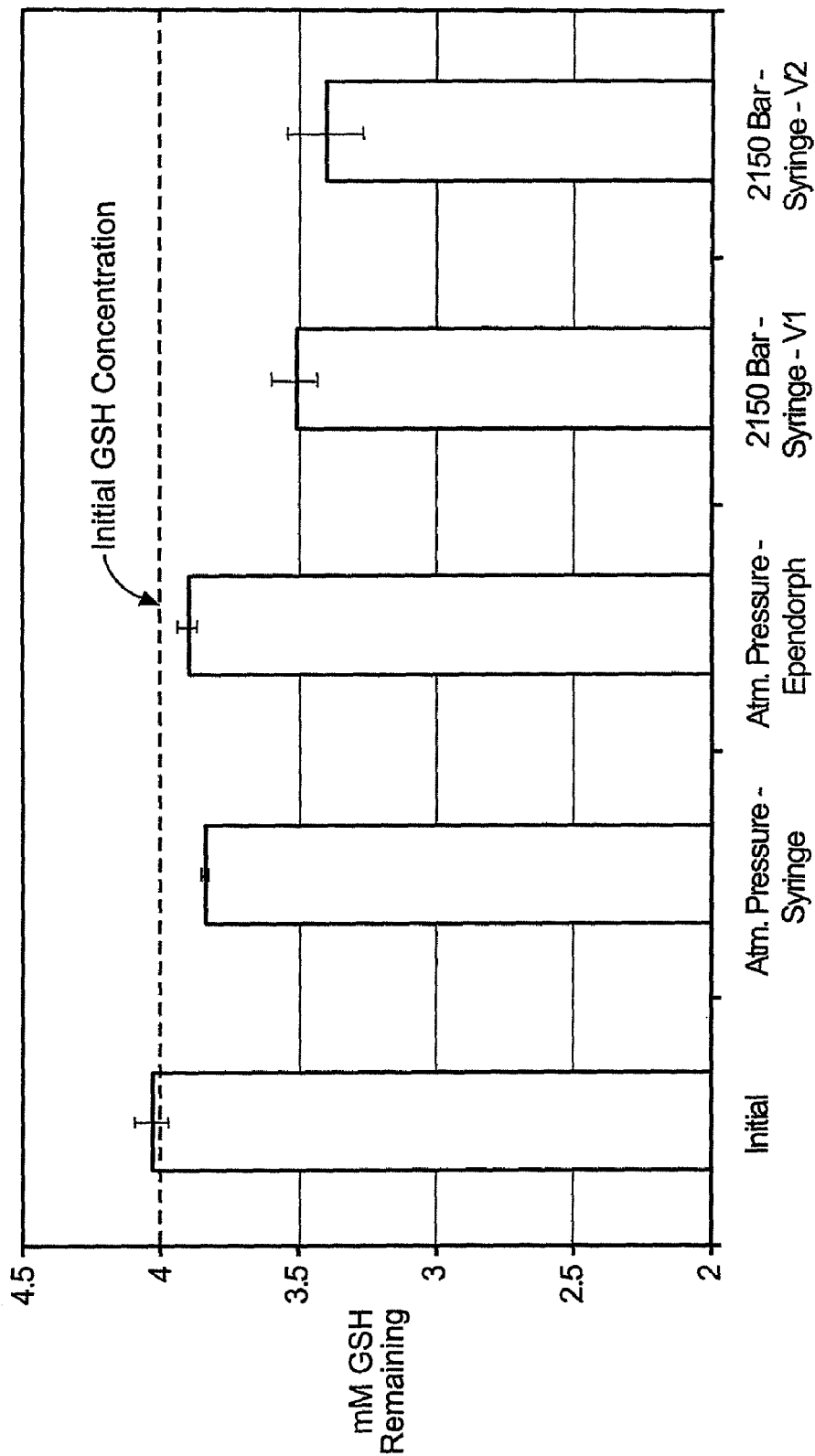
FIG. 10 depicts an experiment demonstrating oxygen transfer through materials that are not substantially oxygen-impermeable at high pressure.

Experimental evidence confirms the importance of using substantially oxygen-impermeable materials at high pressure. 0.35 micromoles of $O_2$ can be transferred during a typical pressure experiment, enough to significantly alter the redox environment of a solution. FIG. 10 depicts an experiment done with conventional syringes currently used for high-pressure treatment. The syringes used were 1 ml low-density polyethylene syringes from Becton Dickinson. A 500 ml aqueous solution at pH 8.0, 4 mM GSH (reduced glutathione), 2 mM GSSG (oxidized glutathione), was kept at 2150 bar for 17 hours. As indicated in FIG. 10, enough oxygen was transferred to lower the concentration of reduced glutathione from 4.0 mM to 3.5 mM or less.

Figure 11:
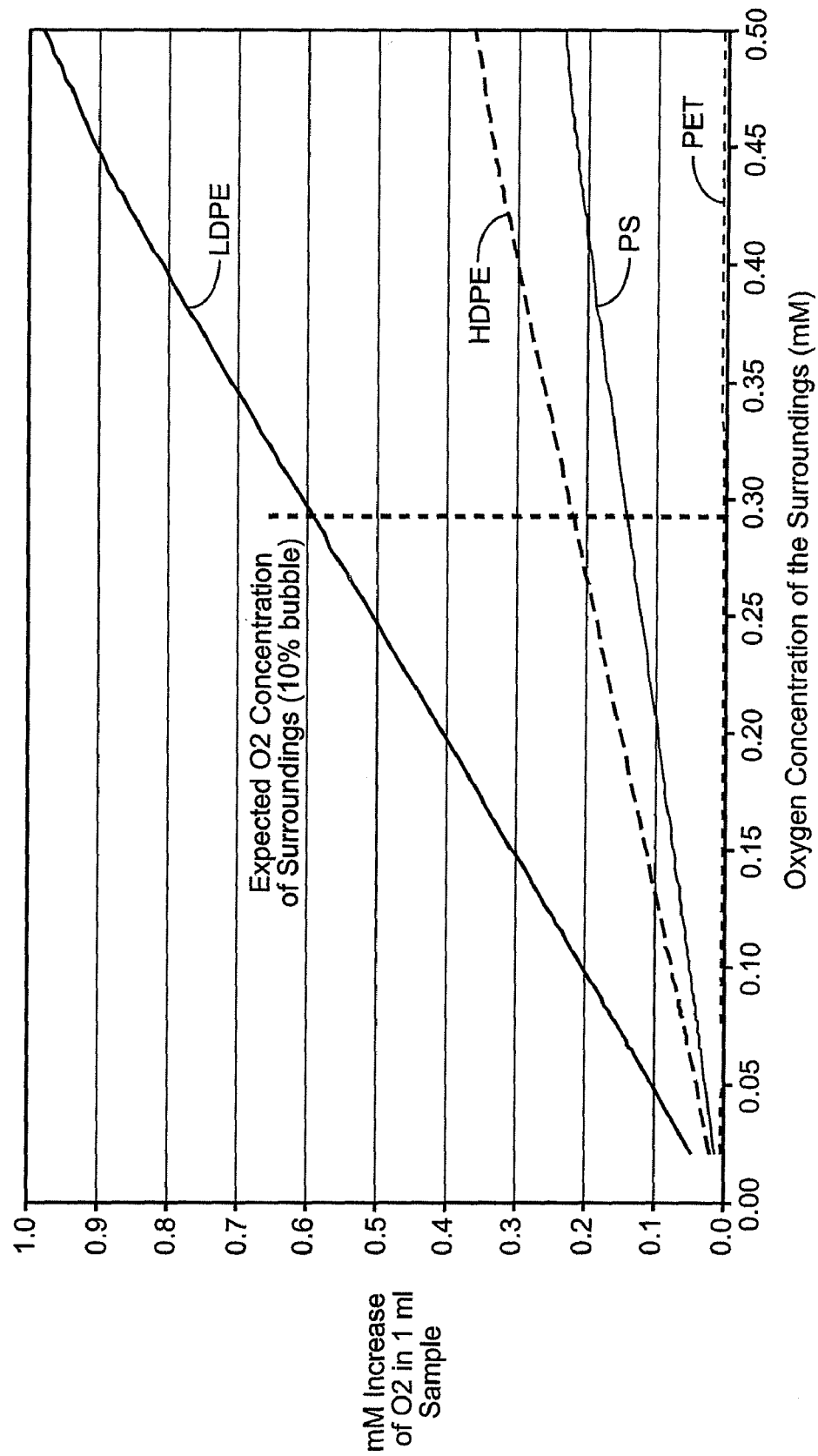
FIG. 11 depicts the calculated transfer of oxygen through the walls of a syringe made from various polymers (LDPE, low density polyethylene, top curve; HDPE, high density polyethylene, second curve from top; PS, polystyrene, third curve from top and second curve from bottom; PET, polyethylene-terephthalate, bottom curve), as a function of the oxygen concentration of the surroundings.

FIG. 11 depicts calculations of the amount of oxygen transfer across the walls of a syringe used under high pressure. The calculations are for a syringe of 1/16 inch thickness, 1.5 inch length, and 0.25 inch outer diameter. The calculation assumed a 24 hour experiment at 2000 bar with a variable surrounding oxygen concentration; the expected oxygen concentration in the surrounding fluid will likely be about 0.3 mM (under the assumption that about 10% of the volume of the surroundings is made up of an air bubble before compression), and is indicated with a vertical dashed line in FIG. 11. The oxygen in the bubble is calculated by simply using the ideal gas law to calculate the amount of air in the bubble at standard temperature and pressure; at higher pressure, the air will dissolve into the solution. The calculation is performed using Fick's law of diffusion at steady-state; diffusion coefficients are used instead of permeability coefficients, as the solubility of $O_2$ in polymers increases dramatically at high pressures. The diffusion coefficients were taken from the *Polymer Handbook*, $4^{th}$ Edition; editors, J. Brandup, E. H. Immergut, and E. A. Grulke; associate editors, A. Abe, D. R. Bloch; New York: Wiley, 1999.

With these assumptions, the calculations indicate that, at the likely value of oxygen concentration in the surrounding liquid, approximately 0.2 mM equivalents of $O_2$ is transferred in tubes made of HDPE, and 0.6 mM equivalents of $O_2$ with LDPE. Oxygen transfer across a polypropylene device was not calculated, but based on relative permeability values, is believed to lie between the values for HDPE and LDPE. Polyethylene terephthalate (PET) is calculated to have almost no transfer of oxygen under the conditions assumed. Consequently, this calculation demonstrates that materials can be judiciously chosen to significantly reduce or almost eliminate oxygen transfer through the polymeric walls of the devices.

Device Embodiments

In one embodiment, the high-pressure device comprises a plurality of wells in a body or plate ("multi-well plate"). One example of such an embodiment is shown in FIG. 1. The embodiment shown is a 96-well plate; a body (1) made of a flexible material substantially impermeable to oxygen mass transfer at high pressure has ninety-six wells (2) for holding liquid samples. The material is preferably (but not necessarily) chosen so that the plate can be formed by injection molding.

Once a suitable material has been chosen for the body of the multi-well plate embodiment, the samples must be introduced into the sample compartments. The inclusion of air pockets in the sample wells is undesirable, as the air will be driven into solution under high pressure, altering the redox environment of the sample, and the presence of air pockets may also cause excessive strain on the material. The wells are thus designed so as to eliminate, to the greatest extent possible, any residual air left in the wells.

Figure 2A:
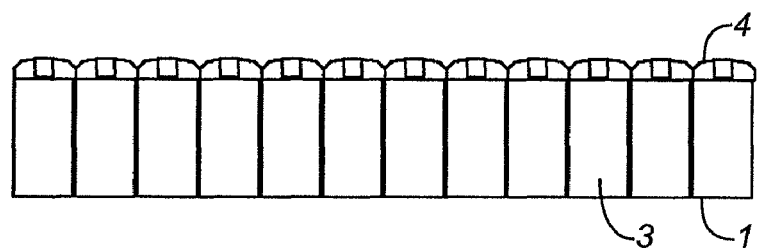
FIG. 2A depicts a side view of one possible embodiment of the multi-well design. The tops of the wells are partially covered in a "dome" to ensure venting of all air.
Figure 2B:
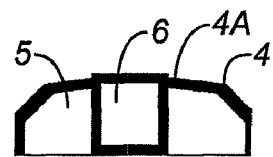
FIG. 2B depicts a side view of the "dome" covering the wells in FIG. 2A. The white section designates the inlet for sample loading. The inlet should be large enough to enable insertion of the appropriate sized pipette tip for reagent delivery and the venting of air.

FIG. 2A depicts a side view (3) of one possible embodiment of the well design. The top of the wells is partially covered in a "dome" (4) to ensure venting of all air. The dome (4) is shown in larger detail in FIG. 2B. The unshaded inlet (6) is the inlet for sample loading, and is surrounded by solid material (5). The inlet should be large enough to enable insertion of the appropriate sized pipet tip for reagent delivery and the venting of air. This domed design enables overfilling to vent all air in the well prior to sealing. Additionally, during the overfill, excess sample will drain down the sides of the dome and will eliminate cross-contamination between samples. The dome (4) has a substantially flat surface on top, in an area closely surrounding the inlet, in order to provide an adequate sealing surface. The dimensions are selected to enable sample loading with standard-sized pipet tips, to enable sample venting, to have sufficient troughs at the base of the domes to prevent cross-contamination, and to provide the previously mentioned flat top to provide an adequate sealing surface.

Figure 3:
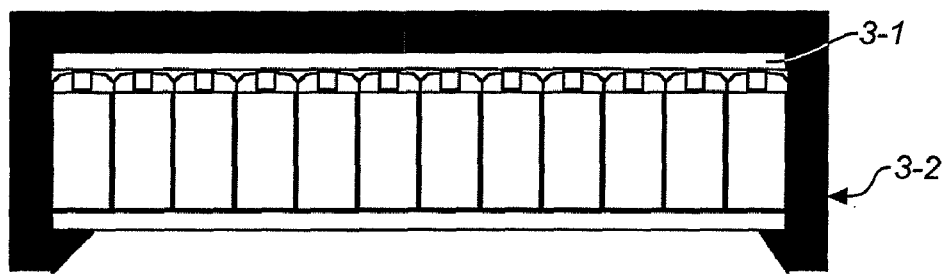
FIG. 3 depicts an example of the 96-well plate embodiment with sealing mat and clamp assembly that can be used to seal the "dome" inlets of FIG. 2A and FIG. 2B.

In one embodiment of the multi-well device, a mat is placed on the top of the multi-well plate to seal the wells. Materials suitable for such a mat include, but are not limited to, silicone rubber. In one embodiment, the mat has a thickness of approximately ⅛ inch, with length and width substantially identical to that of the multi-well plate it is to be used with. The mat should be made from a material of sufficient flexibility to enable a good seal on top of the domes, and to allow deformation due to pressure-induced volumetric changes within the sample. As there is no pressure drop across the sealing surface in this embodiment—that is, the pressure experienced by the sample inside the well is substantially similar to the pressure experienced by the mat—the sealing mat need not provide any additional sealing capacity than that expected at atmospheric pressure. If the sealing material used is not substantially impermeable to oxygen at high pressure, a film which is substantially impermeable to oxygen at high pressure is placed on the sealing mat to inhibit oxygen transfer. The film can be made from materials including, but not limited to, Mylar®. In this embodiment of the multi-well device using a sealing mat, a clamp is affixed on the plate in order to place force on the sealing mat and enable sealing of the wells. The clamp should provide uniform force across the device, and sufficient force to ensure an adequate seal. The clamp should also provide constant force throughout the pressurization cycle, which requires a constant tension clamp (not a constant force clamp) due to the contraction of materials (especially the sealing mat) at high pressure. FIG. 3 depicts the 96-well plate embodiment with sealing mat (3-1) and clamp assembly (3-2).

Figure 4:
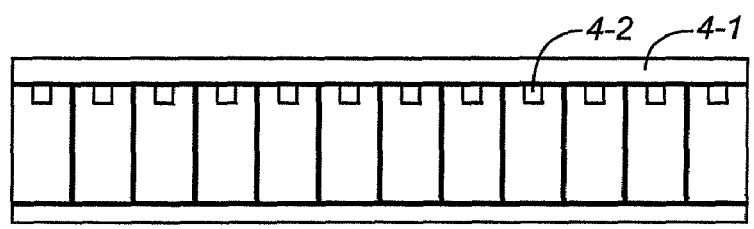
FIG. 4 depicts another embodiment of the multi-well plate design, where a heat-sealed septum is used to seal the wells of a multi-well embodiment of the invention.

In another embodiment of the multi-well plate, depicted in FIG. 4, the wells of the plate are not covered by a dome and sealing mat; instead, the wells are covered by a heat-sealed septum prior to loading the wells with samples. Such septums are commonly used when sealing medical vials. The heat sealed septum ensures a sealed well and prevents sample contamination. Samples are loaded into this embodiment of the multi-well plate by injection with a multi-channel pipetter equipped with needles rather than pipettes. The needles penetrate the septum in order to fill the sample wells. A secondary needle also pierces the sample concurrently with filling, in order to vent air and to allow the well to fill completely. Multi-channel pipetters are available commercially which are designed for pipetting solutions into multi-well plates; such a pipetter can be easily adapted to use a needle for sample loading instead of a pipet tip. After sample loading, the septum is covered with a secondary, adhesive polymeric membrane (4-1). The membrane seals the pierced holes created during sample loading. The membrane should also inhibit oxygen diffusion across the septum; that is, the membrane should be substantially impermeable to oxygen. Potential materials for the adhesive polymeric membrane include, but are not limited to, Mylar®.

Figure 5:
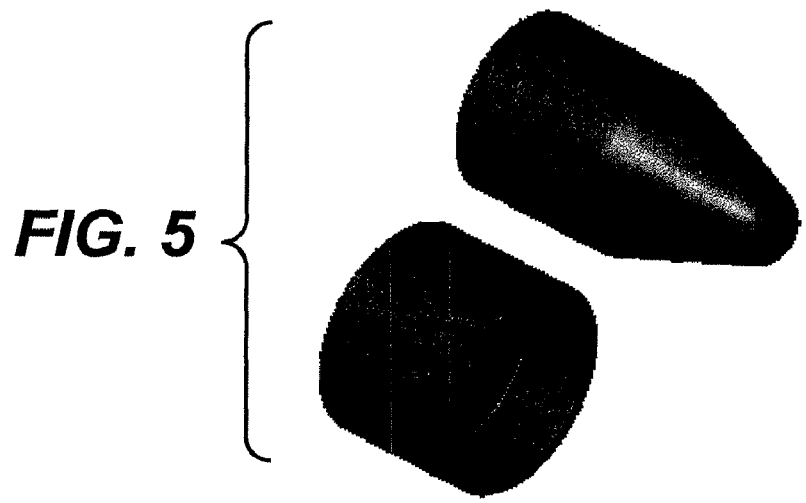
FIG. 5 depicts an embodiment of the constant loading volume container.

In another embodiment, the high-pressure device comprises a container where the volume of the container is fixed at standard pressure; this embodiment is designated the constant loading volume device. The entire container shrinks proportionally upon exposure to high pressure; typically, the container will shrink by about 10% of its volume at 2 kbar, and by about 20% of its volume at 4 kbar; hence, for fabricating this device, a flexible material should be used. One example of such an embodiment is shown in FIG. 5. This device consists of a cylindrical barrel which has a conical bottom. The container can be fabricated with a wide variety of internal volumes; examples of dimensions for containers having 250 µL, 500 µL, 750 µL, or 1000 µL are specified in Table 1. The interior of the container can be graduated, for example at 50 µL increments. The top of the cylindrical barrel can be threaded for seal with a screw cap (which can be shaped as the conical bottom in FIG. 5, or which can also be cylindrical). The threaded screw cap should be capable of maintaining a seal when there is at least about 5 psig pressure differential between the interior and exterior (note that this is a differential pressure, not a total pressure; pressure differentials of this magnitude are similar to those of commercial soda bottles). Typical sizes of embodiments of the constant loading volume device are given in Table 1 (the thickness of the walls of these particular embodiments of the constant loading volume device is 1/16 inch).

TABLE 1

Dimensions for Internal Volume specified

| | Internal Volume | | | |
|---|---|---|---|---|
| | 250 µL | 500 µL | 750 µL | 1000 µL |
| Length (cm) | 0.94 | 0.90 | 1.07 | 1.21 |
| Inner Diameter (cm) | 0.5 | 0.720793 | 0.825102 | 0.908142 |
| Total Height (cm) | 2.44 | 2.40 | 2.57 | 2.71 |
| Cone Volume (mL) (1 cm height) | 0.064795 | 0.134656 | 0.176449 | 0.213753 |

Figure 6:
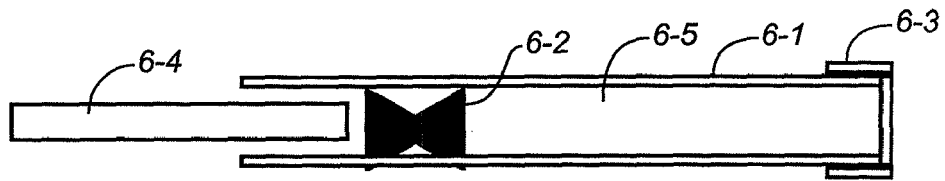
FIG. 6 depicts an embodiment the variable loading volume container.

In another embodiment, the high-pressure device comprises a container of variable loading volume. An example of this embodiment is shown in FIG. 6. In this embodiment, a cylinder with a moveable plug and a removable cap is provided, in a fashion similar to a syringe. When the cylinder is vertically oriented, the plug forms the bottom of the sample compartment, and acts as a seal between the sample compartment and the external environment. The plug can have an attached plunger rod, or a separate plunger rod, which can be used to move the plug to the desired volume before filling the cylinder. The cylinder can be graduated, for example in 50 µL increments, in order to guide placement of the plug to the desired volume. The cylinder can then be filled with the desired sample, with care taken to remove as much residual air as possible. The removable cap is then placed on the top of the cylinder. In one embodiment, the removable cap is threaded, and can simply be screwed on to the top of the cylinder. The threaded removable cap should be capable of maintaining a seal when there is at least about 5 psig pressure differential between the interior and exterior (note that this is a differential pressure, not a total pressure; pressure differentials of this magnitude are similar to those of commercial soda bottles). The sample can then be treated under pressure; after the pressure treatment, the cap can be removed and the contents of the cylinder are poured out, or pushed out by pushing the plug with the plunger rod.

In an alternative embodiment, the closed end of the cylinder is heat sealed. The heat sealed tip is kept intact during the high-pressure treatment. After the treatment, the tip is broken off, and the contents of the cylinder are poured out, or pushed out by pushing the moveable plug with the plunger rod.

In an alternative embodiment, the removable cap is replaced with a breakable tip on the closed end of the cylinder. The breakable tip is kept intact during the high-pressure treatment. After the treatment, the tip is broken off, and the contents of the cylinder are poured out, or pushed out by pushing the moveable plug with the plunger rod.

In another alternative embodiment, a needle can be run between the moveable plug and the cylinder wall to insert the sample into the cylinder. In some embodiments, a one-way valve on the moveable plug allows expulsion of air in the cylinder as the sample is introduced (see FIG. 7A, FIG. 7B, and discussion of a one-way valve assembly below).

It should be noted that, as the moveable plug will move in response to applied pressure, the material used to fabricate the variable loading volume device need not be as flexible as the material used in the other devices of the invention.

Figure 7A:
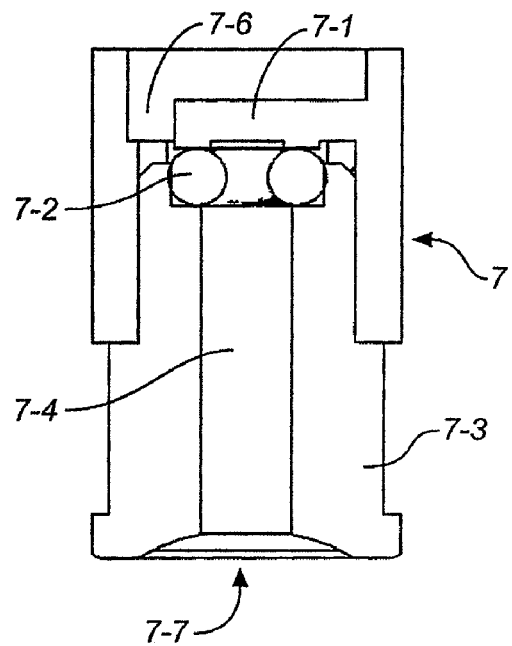
FIG. 7A depicts a sectional view of a one-way valve assembly for use in the variable loading volume container.
Figure 7B:
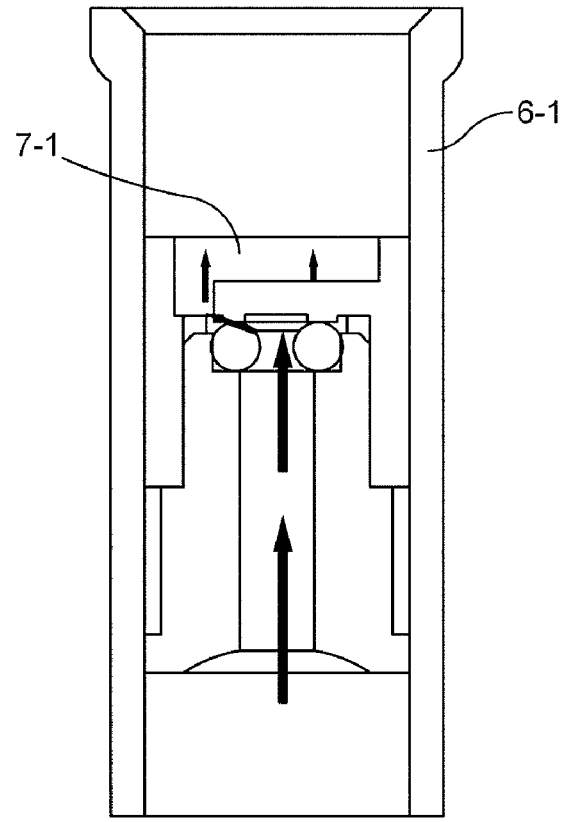
FIG. 7B depicts the one-way valve assembly as installed in the variable loading volume container.

A moveable plug particularly adapted for high-pressure applications is shown in FIG. 7A and FIG. 7B, and is designated a one-way valve plug. In FIG. 7A flexible flap (7-1) forms a seal with the O-ring (7-2). The flap (7-1) and O-ring (7-2) seal the external environment (7-6) from the internal passage (7-4), which opens to the interior of the variable loading volume device at opening (7-7). Area (7-3) is solid. When the one-way valve plug is inserted into the variable loading volume device as depicted in FIG. 7B, the plug can be pressed down until sample begins to bleed out of the one-way valve. This occurs as the flexible flap (molded flap) bends to allow sample to escape via the path indicated by the arrows in FIG. 7B. Pressing down until sample bleeds out of the valve ensures exclusion of as much air as possible from the sample, and also allows adjustment of the amount of sample in the device. As the flap can bend only in one direction (away from the O-ring), neither air nor any other substance present external to the sample can flow back into the sample.

In another embodiment, the high-pressure device comprises a plurality of compartments, where the contents of the compartments can be kept separate or can be mixed together. When treating a liquid sample at high pressure, the contents of the containers can be mixed to alter the chemical solution conditions of the liquid sample. The chemical solution conditions which can be changed include, but are not limited to, any one or more of pH, salt concentration, reducing agent concentration, oxidizing agent concentration, chaotrope concentration, concentration of arginine, concentration of surfactant, or the concentration of any compounds originally present in the liquid sample. In another embodiment, the chemical solution conditions are changed by adding an additional reagent or reactant to the liquid sample. Such a reagent or reactant may comprise an enzyme inhibitor, a drug, a small organic molecule (of molecular weight below about 1000 Daltons), or a protein derivatization reagent.

Figure 8A:
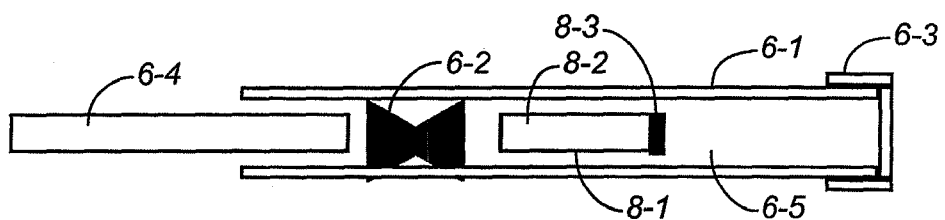
In FIG. 8A, the secondary container is depicted in closed position.
Figure 8B:
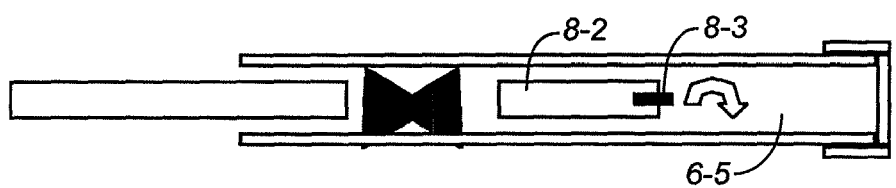
In FIG. 8B, the secondary container is depicted in open position.

In one such embodiment comprising a plurality of compartments where the contents of the compartments can be kept separate or can be mixed together, the high-pressure device comprises a primary compartment enclosing one or more secondary compartments, where the one or more secondary compartments can be opened without opening the primary compartment, whereby the contents of the one or more secondary compartments are released into the contents of the primary compartment. An example of this embodiment is shown in FIG. 8A and FIG. 8B. The variable loading volume container of FIG. 6 is used as the primary compartment, while a secondary container is placed within the variable loading volume container. (It should be noted that the variable loading volume container is used simply as an example; any of the other devices of the invention, such as the constant loading volume container, can be used as the primary compartment.) One end of the secondary container is sealed. A magnetic disk is placed on the other end of the secondary container, which will have an axle built which passes through one wall or side of the secondary container, through the center of the disk, and into the facing wall or side of the secondary container. The disk should be designed with a tolerance so as to fit as precisely as possible inside the secondary container. The disk is designed to freely rotate on the axle, effectively opening and closing the secondary container in a manner analogous to a conventional butterfly valve. A chamfer or beveled edge is used to enable free rotation of the magnetic disk with as tight of tolerance as possible on the rear of the disk. This design enables the magnetic disk to freely rotate, while providing an effective seal when the disk is in the closed position. When this design is used, it is preferable to maintain the primary container in a position such that the secondary container is in a vertical position, in order for gravity to assist in maintaining the magnetic disk in its closed position. The switch is actuated by electric coils placed in a vertical and horizontal fashion around the exterior of the high pressure vessel in which the primary compartment (which contains the secondary compartment) is placed. The horizontal coils are essentially parallel to the magnetic disks within the pressure vessel, in order to generate a magnetic field which maintains the magnetic disks in the closed or sealed position. This is depicted in FIG. 8A. As pressure vessels are commonly made of stainless steel, the coils are designed with the appropriate number of loops, gauge thickness, and current to enable the generation of a magnetic field strong enough penetrate into the interior of the pressure vessel. Alternatively, the pressure vessel could be made out of a material that does not attenuate the magnetic field as much as steel or other such ferromagnetic materials. Another arrangement of electric coils for control of the magnetic disks involves placing coils around the sample rack in a horizontal and vertical manner. In this design, the magnetic field would not have to penetrate the steel walls of the pressure vessel; however, the wires carrying the current would have to run into the interior of the pressure vessel. This can be accomplished by fabricating the base of a sealing plug of a conventional pressure vessel out of an insulating ceramic, rather than steel.

When the magnetic disks are to be kept in the closed position, the horizontal field is turned on, maintaining the magnetic disks in the horizontal position and sealing the solution contents of the secondary container from those of the primary container. To enable solution exchange, current in the horizontal and vertical coils is alternated, with alternating current, to generate a rotating electromagnetic field and spin the magnetic disk. This opens the contents of the secondary container to the primary container, while the motion of the disk enables convection and solution exchange. This is depicted in FIG. 8B.

Figure 9:
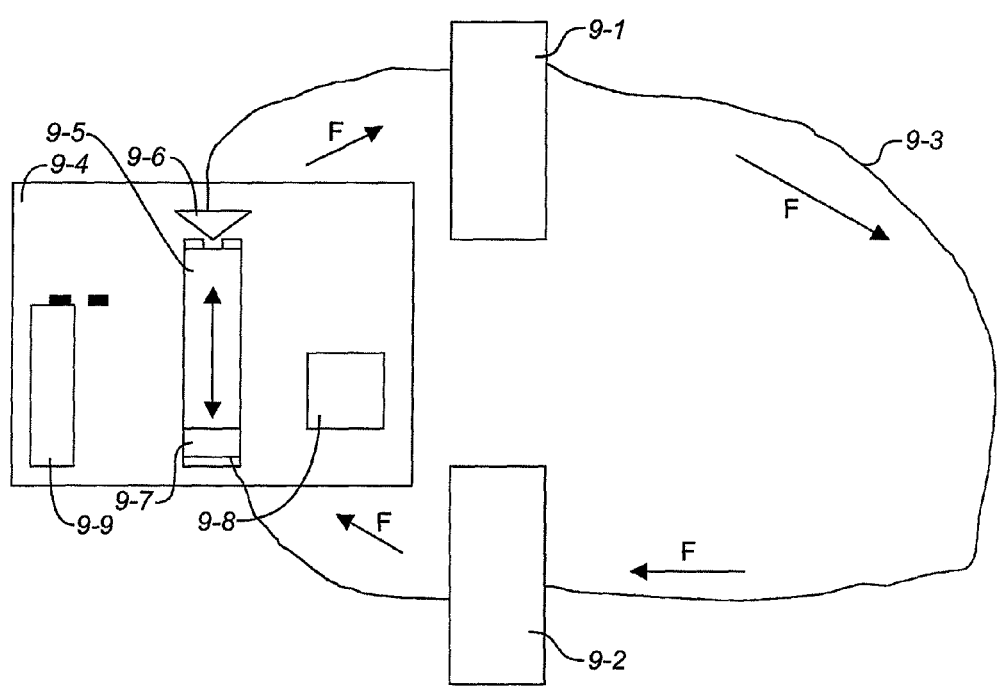
FIG. 9 depicts another embodiment useful for mixing solutions at high pressure.

In another such embodiment comprising a plurality of compartments where the contents of the compartments can be kept separate or can be mixed together, the high-pressure device comprises at least two compartments connected by flow paths, where the compartments and the flow paths form a closed circular loop with at least one pump. An example of this embodiment is shown in FIG. 9. A liquid sample is placed in the "dissociation" chamber, while a second solution is placed in the "refolding" chamber. Additional dissociation chambers, refolding chambers, and flow paths can be added as desired. The device is then placed in the pressure chamber and pressurized. When mixing of the liquid sample with the second solution is desired, a piston pump is turned on, circulating the liquids through the closed circular loop. The piston can be made of a magnetized material, enabling control of the pump rate by a magnetic field. Microprocessor-controlled battery-powered coils can be placed inside the pressure chamber, along with the chambers and flow loop, in order to control the piston pump. (The microprocessor is preferably embedded in epoxy to reduce pressure transfer to the microprocessor itself.) Alternatively, the arrangement of metal coils for control of the secondary compartment metal disk in the primary container/secondary container device can be used to control the piston. Check valves enable unidirectional flow.

These embodiments can be used for refolding of proteins under various conditions. For example, pressure-modulated refolding (pressures of 250-5000 bar) can be conducted in non-denaturing chaotrope solutions at alkaline pH (near 10.0) and then the pH of the solution can be gradually decreased in step-wise fashion until a value of pH 8.0 is obtained. The use of high hydrostatic pressure will remove the need to use high concentrations of chaotropes to promote aggregate dissociation. By combining pressure and chaotrope/pH modulated refolding methods, higher refolding yields are expected to be achieved.

Introduction of Samples into the Sample Compartments

Once a suitable material has been chosen for the body of the device, the samples must be introduced into the sample compartments. The device is adapted to receive liquid samples, and thus a variety of standard methods for liquid transfer can be employed. Hand-held or robotic pipettes, syringes, pumps, and other liquid transfer instruments well-known in the art can be employed. Care should be taken to exclude as much residual air as possible from any of the devices prior to pressurization, which helps prevents material failure and prevents the oxygen contained in the air from being dissolved in the system. The devices can be filled in an inert atmosphere, such as nitrogen or argon, in order to prevent residual air that cannot be excluded from altering the oxygen content of the liquid when pressure is applied.

In certain additional embodiments, prior to loading a liquid sample into the compartment, one or more gases will be sparged through the sample. Such gases include, but are not limited to, relatively unreactive gases such as helium, nitrogen, neon, argon, or krypton, where it is desirable to displace as much dissolved oxygen as possible. Usually rigorous exclusion of oxygen is desired, but in certain circumstances where a higher-than-normal oxygen content is desired in the solution, air or oxygen itself can be sparged through the sample. In yet additional embodiments, vacuum may be applied to the sample in order to de-gas the sample. In yet additional embodiments, sparging with unreactive gas can be followed by vacuum treatment in order to remove as much dissolved oxygen as possible; the sparge-pump cycle can be repeated as necessary.

Sealing of the Sample Compartments and Sample Introduction

Sample compartments can be sealed with seals fabricated from silicone, rubber or other material. In one embodiment, the seal material is inert to the contents of the sample well, since the liquid sample may come into contact with the seal during the experiment. When a seal such as rubber is used which is not substantially impermeable to oxygen at high pressure, a second seal which is substantially oxygen-impermeable at high pressure is applied over the first seal to reduce or prevent oxygen mass transfer.

The sample compartments can be sealed before or after introduction of the liquid sample. If the sample compartment is sealed after the introduction of the liquid sample, then the necessity of penetrating the seal is avoided. However, if the sample compartment is sealed before introduction of the liquid sample, the seal must allow introduction of the sample. A seal made of materials such as rubber or silicone can be pierced with a needle in order to introduce liquid sample; a second needle can be used to vent air from the compartment. The second, venting needle is inserted only to the extent needed to penetrate the seal and minimally extend into the chamber, in order to withdraw as much air as possible. Filling of the chamber is complete once air is completely expelled and liquid begins to be expelled from the chamber.

Since rubber and certain silicones are relatively permeable to oxygen at high pressure, a second sealing layer can be applied in order to prevent mass transfer of oxygen at high pressure. A layer of Mylar® or other suitable material which is substantially oxygen-impermeable at high pressure can be laid down over the first seals.

In view of the teachings provided herein, the skilled artisan will also be able to further modify the methods described herein as well as devices, materials and conditions for optimizing these for particular fusion protein systems.

EXAMPLES

The present invention is further described with reference to the following Examples; however, these Examples are not limiting the scope of the present invention.

Example 1

Figure 13A:
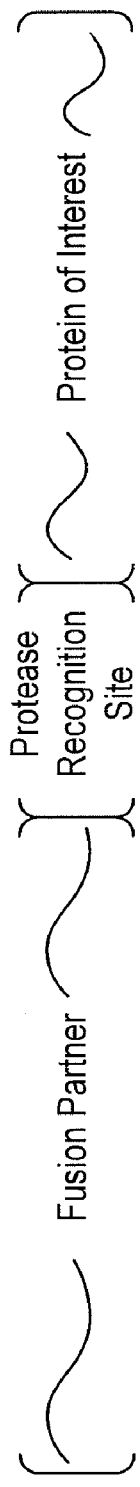
FIG. 13A shows an example of a protein of interest coupled with a fusion partner that can be cleaved via a protease recognition site.
Figure 13B:
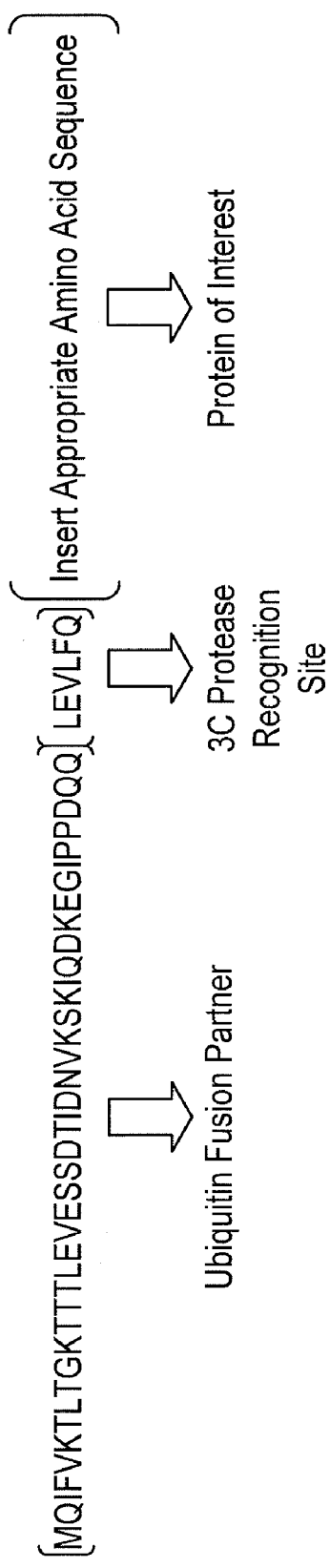
FIG. 13B shows a protein of interest/ubiquitin fusion protein, with the 3C protease recognition (cleavage) site also indicated.

Preparation of a Recombinant Protein of Interest Cleaved by a Protease from a Fusion Protein at High Pressure A recombinant protein is expressed as a fusion protein linked to a fusion partner (FIG. 13A). In a more specific example, the fusion partner is an ubiquitin sequence that is cleaved by a 3C protease (FIG. 13B). The recombinant protein is designed such that the ubiquitin sequence could be cleaved from the protein of interest sequence following isolation of the fusion protein from the fermentation harvest. The fusion protein consists of the first 41 amino acids from yeast ubiquitin, followed by 6 amino acids that create a 3C protease cleavage site, fused to the complete sequence of the protein of interest. Cleavage of the fusion protein by recombinant 3C protease (3CP) generates the proper protein sequence with the correct amino-terminus.

High hydrostatic pressure, at but not limited to 2150 bar, is applied to solubilize the recombinant protein of interest from the ubiquitin fusion partner from inclusion bodies. The refolding buffer comprising one or more additional agents is selected from one or more stabilizing agents, one or more buffering agents, one or more surfactants, one or more disulfide shuffling agent pairs, one or more chaotropic agents, one or more salts, and combinations of two or more of the foregoing. Solubilization yield is calculated using the following equation:

Solubilizing Yield(%)=Mass of Fusion Complex in the Supernatant/(Mass of Fusion Complex in the Supernatant and the Precipitate)*100

Where the mass of protein is quantified by RP-HPLC analysis using the Porous method (see methods).

Cleavage yield is calculated using the following equation:

Cleavage Yield(%)=Mass of Cleaved Fusion Complex/(Total Mass of Cleaved and Uncleaved Fusion Partner in the Supernatant)*100

The mass of protein (both cleaved and non-cleaved) is quantified by RP-HPLC analysis using the Porous method (see below).

The protocols for obtaining these optimal refolding solution conditions of refolding buffer comprising one or more additional agents (selected from one or more stabilizing agents, one or more buffering agents, one or more surfactants, one or more disulfide shuffling agent pairs, one or more chaotropic agents, one or more salts, and combinations of two or more of the foregoing) are described in Examples 2-4.

Unless otherwise noted, the protocols for sample preparation, pressure treatment, sample analysis, and statistical analysis described below are used for the experiments described in the present example and throughout the Examples. Similarly, the identity and sources of all reagents are as listed in the "Materials" section, below.

Sample Preparation

The recombinant protein of interest solubilization and cleavage solutions are prepared by the dilution of stock solutions into microcentrifuge tubes with 500 uL final volume. All sample preparation is conducted within a nitrogen hood to reduce oxygen partial pressures to no greater than 1% of atmospheric levels. To ensure sample integrity, any chaotropes or redox stock solutions are made fresh prior to use. All other stock solutions are stored at 4° C.

During sample preparation, reagents are added in the following order: buffer, chaotrope, EDTA, other non-oxidizing compounds, oxidized disulfide shuffling agent, reduced disulfide shuffling agent, water, inclusion bodies, and protease solution. The sample is then mixed and the appropriate amount of protein is added to achieve the desired final protein concentration. The samples are loaded into 1 ml heat-sealed syringes (Becton-Dickenson Inc., USA). The plunger is put in place, and residual air is vented by running a 21-gauge needle alongside the plunger until the plunger is flush with the sample (described in greater detail below). The samples are removed from the nitrogen hood. Samples are prepared in this manner for both pressure treatment and atmospheric controls.

High pressure refolding devices, described as variable volume sample vials, (one per sample) are prepared by heat-sealing the Luer end of a 1 ml polypropylene syringe (LUER-LOK is a registered trademark of Becton, Dickinson and Co., Franklin Lakes, N.J. for interlocking tubing and syringe seals), and numbered for identification. The end of the syringe is trimmed so that the final volume of the syringe was 800 μL. Samples are prepared in 1.5 ml microcentrifuge tubes as previously described and then placed in the heat-sealed syringes (St. John 1999). The syringes are then sealed with the plunger, using a 21-gauge needle along the side of the plunger to vent all air from the sample. At that point, samples are ready for pressure treatment (Seefeldt et al. 2004).

Pressure Treatment

Manually driven, 4000 bar high pressure generators are used with water as a pressure transmitting fluid (High Pressure Equipment Co., Erie, Pa.). The sealed syringes are placed in custom-built pressure cells, which are commercially available (BaroFold Inc, Boulder, Colo.), and pressurized to the appropriate pressure over a period of two to five minutes.

The refolding reaction is conducted overnight (typically sixteen hours). For depressurization, the pressure is reduced by 250 bar every five minutes until atmospheric pressure is reached. All testing is conducted at room temperature (approximately 25° C.) unless otherwise stated. The samples are removed from the pressure vessels and syringes and placed into microcentrifuge tubes in the nitrogen hood to prevent oxidation.

Sample Analysis

All sample analysis/chromatography, peak integration, and yield analysis is conducted as described below. The percentage of the recombinant protein of interest that is solubilized and cleaved is calculated by the method discussed below and, additionally, the presence of the truncated ubiquitin folding partner is tracked to further confirm protease cleavage. The chromatography methods are as follows:

Refolding and cleavage of the recombinant protein of interest is monitored by reverse phase HPLC using a Poros R2/10 column (4.6×100 mm; Applied Biosystems). Protein elution is detected at 220 nm. Elution is accomplished using 0.1% TFA (solvent A) in water and 0.1% TFA (solvent C) in acetonitrile according to Table 2 below.

TABLE 2

| Time (min) | % solvent A | % solvent C | Flow (ml/min) |
|---|---|---|---|
| 0.00 | 82.0 | 18.0 | 3.00 |
| 1.00 | 82.0 | 18.0 | 3.00 |
| 14.00 | 40.0 | 60.0 | 3.00 |
| 15.00 | 10.0 | 90.0 | 3.00 |
| 16.00 | 10.0 | 90.0 | 3.00 |
| 16.50 | 82.0 | 18.0 | 3.00 |
| 18.00 | 82.0 | 18.0 | 3.00 |

Statistical Analysis

The software program Design Expert 6.0 (Stat-Ease Inc., Minneapolis, Minn.) is used to develop all SED designs and to analyze significant model factors.

Materials

Inclusion bodies containing the recombinant protein of interest, fusion partner, and cleavage site are manufactured using known methods described Sambrook J., Fritsch, E. F. and Maniatis, T. (1989) in *Molecular Cloning: a Laboratory Manual*, Second Ed., Cold Spring Harbor Laboratory Press, Cold Spring Harbor, N.Y. (incorporated herein by reference in its entirety) and applied as described in Example 6. Recombinant 3C protease is purchased for use (CN# TB420, EMD Chemicals, San Diego, Calif.).

The other reagents are obtained as follows:

| Chemical Name | Vendor | Cat# |
|---|---|---|
| Arginine HCL | Sigma | A5131 |
| CAPS | Sigma | C2632 |
| CHES | Sigma | C2885 |
| Concentrated HCl | VWR | VW3110-3 |

-continued

| Chemical Name | Vendor | Cat# |
|---|---|---|
| Cystamine | Sigma | C8707 |
| DTT | Sigma | D9779 |
| EDTA | Sigma | EDS |
| Guanidine HCl | Sigma | G4505 |
| HEPES | Sigma | H3375 |
| MOPS | Sigma | M3183 |
| NaOH 10N | VWR | VW3247-1 |
| Nitrogen NF grade | General Air | 1201809 |
| Sodium Chloride | Fisher | BP358-1 |
| TAPS | Sigma | T5130 |
| Tris HCl | Sigma | T65941 |
| Urea | Fluka | 51458 |
| Water | Sigma | W3500 |

Example 2

Initial Selection and Optimization of Solution Conditions for Solubilization and Cleavage of the Recombinant Protein of Interest Experiments are conducted to examine the effect of pressure treatment (2150 bar) on the solubilization and protease 3C cleavage of the recombinant protein of interest inclusion bodies at urea concentrations ranging from 1.5-4.5M and inclusion bodies concentrations of up to 2 mg/ml of the recombinant protein of interest at alkaline pH's in a reducing environment (to enable 3C protease cleavage). Studies are conducted to determine if 3C protease cleavage can occur during pressure-modulated solubilization at 2150 bar. These conditions are selected for the first screening studies based on previous work conducted at atmospheric pressure and the standard protocols in the field.

DTT concentrations are screened to determine the minimum concentration that can still reduce the sample and while allowing for 3C protease cleavage of the recombinant protein of interest during pressure treatment.

Studies are conducted to determine that the solubilization reaction is facilitated preferentially by pressure, rather than solution conditions. The recombinant protein of interest inclusion bodies, at a constant total inclusion body protein concentration, are solubilized at pressures of 0, 1000, 2150, and 3000 bar in a specific refolding solution.

Example 3

Effect of Solution Conditions on the Pressure Enabling Manufacturing Technology (PreEMT) Solubilization and Cleavage of the Recombinant Protein of Interest Six Parameter, Full Central Composite Design A statistically engineered design (SED) is developed to test the effect of pH (7.5-10), DTT concentration (0.8-10 mM), total protein concentration (6-30 mg/ml), pressure (1750-3000 bar), urea (0-2M), and ionic strength (0-250 mM), on the pressure-enhanced solubilization and cleavage of the recombinant protein of interest from inclusion bodies. A rotatable, full, central composite design is developed which tests each factor over five levels, taking into account interactions, resulting in 78 experimental points and 10 center points. The solubilization yield and mass of solubilized and cleaved recombinant protein of interest is monitored by the methods described in Example 1.

The randomized set of experiments developed in the SED are shown in Table 3. Center points are highlighted in black. Center points (replicates) are defined as replicates in the center of the experimental design space which are used to calculate the experimental error and accuracy of the resulting model output. The SED model design is used to determine the interactions of pH, urea, ionic strength, redox ratio, and redox concentration on the solubilization, refolding and cleavage yield, in the form of multi-dimensional plots.

TABLE 3

Full central composite SED for optimization of process conditions on the solubilization and cleavage of the recombinant protein of interest.

| Variables: Run ID# | pH | DTT mM | Prot. Conc. mg/ml | Pressure kbar | Urea M | Ionic Strength mM |
|---|---|---|---|---|---|---|
| 43 | 8.8 | 5.4 | 30 | 2.4 | 1.0 | 125 |
| 44 | 8.0 | 2.5 | 26 | 2.8 | 1.6 | 45 |
| 45 | 8.8 | 5.4 | 18 | 2.4 | 1.0 | 125 |
| 46 | 9.5 | 8.3 | 26 | 2.8 | 0.4 | 45 |
| 47 | 8.8 | 5.4 | 18 | 2.4 | 1.0 | 125 |
| 48 | 9.5 | 8.3 | 26 | 2.0 | 0.4 | 205 |
| 49 | 8.0 | 2.5 | 26 | 2.8 | 1.6 | 205 |
| 50 | 9.5 | 2.5 | 10 | 2.0 | 0.4 | 45 |
| 51 | 8.0 | 8.3 | 26 | 2.8 | 0.4 | 205 |
| 52 | 8.8 | 5.4 | 18 | 2.4 | 1.0 | 125 |
| 53 | 8.0 | 2.5 | 10 | 2.8 | 1.6 | 45 |
| 54 | 9.5 | 2.5 | 10 | 2.8 | 0.4 | 45 |
| 55 | 8.8 | 5.4 | 18 | 2.4 | 1.0 | 0 |
| 56 | 9.5 | 2.5 | 10 | 2.0 | 1.6 | 45 |
| 57 | 9.5 | 2.5 | 10 | 2.0 | 1.6 | 205 |
| 58 | 8.8 | 5.4 | 6 | 2.4 | 1.0 | 125 |
| 59 | 9.5 | 8.3 | 26 | 2.0 | 0.4 | 45 |
| 60 | 9.5 | 2.5 | 26 | 2.0 | 0.4 | 205 |
| 61 | 8.8 | 5.4 | 18 | 2.4 | 1.0 | 125 |
| 62 | 8.8 | 5.4 | 18 | 2.4 | 1.0 | 125 |
| 63 | 8.0 | 2.5 | 10 | 2.0 | 1.6 | 205 |
| 64 | 9.5 | 8.3 | 10 | 2.8 | 0.4 | 45 |
| 65 | 9.5 | 8.3 | 26 | 2.8 | 1.6 | 205 |
| 66 | 9.5 | 8.3 | 10 | 2.0 | 1.6 | 205 |
| 67 | 8.0 | 2.5 | 26 | 2.8 | 0.4 | 205 |
| 68 | 9.5 | 8.3 | 10 | 2.0 | 1.6 | 45 |
| 69 | 8.0 | 2.5 | 26 | 2.0 | 0.4 | 45 |
| 70 | 8.8 | 5.4 | 18 | 2.4 | 1.0 | 250 |
| 71 | 9.5 | 8.3 | 26 | 2.0 | 1.6 | 45 |
| 72 | 8.0 | 8.3 | 10 | 2.8 | 0.4 | 45 |
| 73 | 9.5 | 2.5 | 26 | 2.0 | 1.6 | 45 |
| 74 | 8.8 | 5.4 | 18 | 2.4 | 0.0 | 125 |
| 75 | 8.8 | 0.8 | 18 | 2.4 | 1.0 | 125 |
| 76 | 9.5 | 8.3 | 10 | 2.0 | 0.4 | 45 |
| 77 | 8.0 | 2.5 | 10 | 2.8 | 0.4 | 205 |
| 78 | 8.0 | 2.5 | 10 | 2.0 | 0.4 | 45 |
| 79 | 9.5 | 2.5 | 26 | 2.0 | 1.6 | 205 |
| 80 | 8.0 | 2.5 | 26 | 2.0 | 0.4 | 205 |
| 81 | 8.0 | 8.3 | 10 | 2.0 | 1.6 | 45 |
| 82 | 10.0 | 5.4 | 18 | 2.4 | 1.0 | 125 |
| 83 | 8.0 | 8.3 | 26 | 2.8 | 1.6 | 205 |
| 84 | 8.0 | 2.5 | 10 | 2.8 | 1.6 | 205 |
| 85 | 9.5 | 8.3 | 10 | 2.8 | 1.6 | 45 |
| 86 | 8.8 | 5.4 | 18 | 2.4 | 1.0 | 125 |

After the first SED is conducted, statistical analysis is used to examine the significant model terms. At this point, subsequent solubilization, refolding and cleavage studies are conducted with the statistically significant parameters identified in the SED. These studies are conducted with replicates and designed around the SED conditions, to confirm the model predictions and experimental error. In some cases, the conditions and ranges defined in the initial SED are too broad to confirm the development of an optimum process. In these cases, subsequent SED's are employed to further fine tune the process parameters (Example 4).

Example 4

Central Composite SED Experiments using pH, Urea and Total Protein Solubilization as Parameters An example of a subsequent SED to further optimize the effect of pH (9-9.5), urea concentration (1.5-2M), and total protein concentration (24-40 mg/ml) on the refolding, solubilization and cleavage yield of the recombinant protein of interest is shown in Table 4.

TABLE 4

Experimental conditions for a subsequent SED: An example of the examination of the effect of total protein concentration, pH and urea concentration on the solubilization, refolding and cleavage of the recombinant protein of interest. Center points are highlighted.

| Sample # | Total Protein Concentration (mg/ml) | pH | Urea Concentration [M] |
|---|---|---|---|
| 1 | 33 | 9.25 | 1.75 |
| 2 | 33 | 9.25 | 1.75 |
| 3 | 40 | 9 | 2 |
| 4 | 26 | 9 | 2 |
| 5 | 40 | 9 | 1.5 |
| 6 | 26 | 9.5 | 2 |
| 7 | 33 | 9.5 | 1.75 |
| 8 | 40 | 9.5 | 1.5 |
| 9 | 33 | 9.25 | 1.75 |
| 10 | 33 | 9.25 | 1.5 |
| 11 | 33 | 9.25 | 1.75 |
| 12 | 26 | 9.5 | 1.5 |
| 13 | 40 | 9.25 | 1.75 |
| 14 | 33 | 9.25 | 1.75 |
| 15 | 33 | 9 | 1.75 |
| 16 | 33 | 9.25 | 1.75 |
| 17 | 26 | 9 | 1.5 |
| 18 | 40 | 9.5 | 2 |
| 19 | 26 | 9.25 | 1.75 |
| 20 | 33 | 9.25 | 2 |

Example 5

Confirmation of the Recombinant Protein of Interest Solubilization, Refolding and Cleavage After SED Optimization Inclusion bodies of the recombinant protein of interest are incubated at the optimum pressure, time, buffer, redox agents, non-denaturing chaotropes, surfactants, amino acids or coagents determined by SED analysis, in triplicate with atmospheric controls. The samples are analyzed by HPLC to determine the appropriate refolding yields and confirm solubilization and cleavage of the fusion protein. Yield are calculated with 95% confidence intervals to confirm the statistical significance of the refolded and cleaved material as well as determine that that the yield was statistically significantly improved in comparison to inclusion body samples incubated in identical solution conditions at atmospheric pressure.

Example 6

Solubilization and Cleavage of Autocatalytic Fusion Protein Expression of the Fusion Partner to the Protein of Interest cDNA of the target polypeptide is amplified by PCR from the pEGFP-N2 vector (Clonetech) (Shih et al. 2005). The target polypeptide is any polypeptide that the skilled artisan desires to produce recombinantly. Alternative fusion partners are NusA, Trx, GST, CBP, or $His_6$Tag (Shih et al. 2005). Parallel sticky-end PCR cloning, protein induction, and solubility testing is carried out as previously described (Shih et al. 2002) (herein incorporated by reference in its entirety). Cloning generates a fusion protein with the sequence: Maltose Binding Protein—TEV protease—cleavage site of TEV—target polypeptide as described by Shih et al. (Shih et al. 2005) (herein incorporated by reference in its entirety). In this example, the cleavage site of TEV is glutathione—P5-P4-Tyrosine—P2-Glycine—P1', where P2, P4, and P5 are non-conserved acids. The P1' amino-acid can be any amino acid except for proline (Shih et al. 2005). It should be noted that the autocatalytic fusion partner is not limited to only using this protease. The fusion partner thus contains a cleaving protease and the specific cleavage sequence, enabling the autocatalytic cleavage of the fusion partner once it is solubilized or disaggregated though high pressure treatment.

After the sequence of the fusion protein is generated, the plasmid is expressed using standard prokaryotic expression. For fusion protein induction, bacterial cultures are induced with 0.1 mM IPTG at a cell density of $OD_{600}$ of 0.6. Fermentation and solution conditions and temperatures can be optimized to maximize the formation of inclusion bodies (see Shih et al. 2005 (herein incorporated by reference in its entirety).

Purification of Inclusion Bodies after *E. Coli* Fermentation

*E. coli* cell paste containing the inclusion bodies is suspended in a buffer composed of 50 mM Tris (pH 7.8), 20 mM EDTA, and 0.25 mg/ml lysozyme for one hour at 25° C. for cell lyses (Buchner and Rudolph, 1991 (incorporated herein by reference). Triton-X-100 detergent and NaCl are added to achieve a final concentration of 2% (v/v) and 0.5 M, respectively. After thirty minutes at room temperature and after homogenization sonication, the solution is centrifuged at 25,000×g for one hour at 4° C. The supernatant is then discarded and the pellets are suspended and sonicated in 50 mM Tris (pH 7.8) buffer containing 20 mM EDTA. (If a $His_6$Tag is used, the solutions are made EDTA free.) This solution is centrifuged again at 25,000×g for an additional hour at 4° C. The suspension, sonication, and centrifugation steps are repeated until the supernatant is clear of any mucosal, dark debris, and the remaining pellet retained a clean, white, grainy texture, otherwise commonly known as washed inclusion bodies. After the purified pellet is obtained, 25 ml of the wash buffer (50 mM Tris (pH 7.8) and 20 mM EDTA) is added to resuspend the inclusion body. No protease inhibitors are added to this processing step to prevent inhibition of the TEV protease. The inclusion body suspension is separated into 1 ml aliquots and stored at −80° C. until used.

Sample Preparation Prior to Pressure Treatment

The expressed inclusion bodies or soluble aggregates are placed in buffer at a fusion protein concentration of approximately 0.5- to 2 mg/ml. The cleavage buffer is prepared to optimize the conditions in accordance with Examples 1-4. Accordingly, testing is performed to examine solubilization, cleavage, and refolding yield as a function of buffer salts, pH, ligands, stabilizing agents (including preferential excluding compounds, surfactants, and amino acids), and chaotropes. Refolding pressure, temperature, hold times, and depressurization rates are also optimized. Five different vials can be used to contain the sample during pressure treatment: 96-well plates, variable volume sample vials, constant volume sample vials, containers that enable dialysis and/or solution exchange under pressure, and containers that enable solution exchange under pressure. Where TEV is used as the fusion protease/partner, the buffer is includes a reducing agent (such as TCEP or DTT) to prevent the oxidation of the free cysteine that is present in the active site. Additionally, the reaction is conducted at a sufficiently alkaline pH to maintain the deprotonated conformation of the free cysteine that is present in the catalytic triad of the protease. Samples are slowly pressurized (over approximately 10 minutes) to minimize system heating and then held at the selected optimal temperature and pressure. During this time the inclusion body is solubilized and cleaved by the autocatalytic fusion partner. Soluble target polypeptide is thus recovered. If the target polypeptide has disulfide bonds, it is unlikely that the native structure is formed due to the reducing environment preventing the formation of disulfide bonds in the protease. If this is the case, active target polypeptide is obtained by decreasing the pressure in the sample to 1 bar and adding reduced and oxidized disulfide agents and repressurizing. The second pressurization step is not always required to enable refolding. Additionally, dialysis and/or solution exchange at elevated pressure can be used to add disulfide shuffling agents or alter further solution conditions without depressurization to facilitate refolding and formation of the native disulfide bonds.

Pressure Generation

Pressure is generated by using either a hydraulic intensifier equipment driven by high-pressure nitrogen (200-400 bar) with oil as a pressure transmitting fluid (High Pressure Equipment, Erie, Pa.). A cloverleaf reactor is used in conjunction with the hydraulic intensifier. Additionally, manually or mechanically driven 4000 bar and 6750 bar High Pressure Generators can be used with water as a pressure transmitting fluid. (High Pressure Equipment, Erie, Pa.) Custom-built pressure cells are used with these pressure generators (Baro-Fold Inc.).

Analysis of Solubilization Yield

The analysis of the solubilization yield is conducted by running reverse-phase high performance liquid chromatography (RP-HPLC), SDS-PAGE, and BCA total protein assays to identify the amount of target polypeptide in the supernatant and pellets remaining after the autocatalytic solubilization and cleavage of the fusion protein contained in the inclusion bodies and cell lysate paste. Where applicable, other analytical methods can also be used, such as: size exclusion chromatography (SEC-HPLC), capillary electrophoresis, fraction flow field chromatography, anionic or cationic exchange chromatography. It should be noted that if any insoluble material remains, it will be analyzed by first solubilizing it in an approximately 2% SDS solution prior to analysis by RP-HPLC, SDS-PAGE, and BCA total protein assays. Additionally, denaturing solutions containing chaotropes (such as 8M guanidine) can be used to solubilize insoluble material after pressure treatment for analysis by RP-HPLC. Solubilization yield is calculated through the following equation:

Solubilizing Yield(%)=Mass of Target Polypeptide in the supernatant (cleaved and uncleaved)/(Mass of Target polypeptide in the supernatant and the precipitate (cleaved and uncleaved))*100

Analysis of Cleavage Yield

An assay is developed to quantify the cleavage yield of the target polypeptide solubilized during pressure treatment. Possible assay techniques would include, but are not limited to, SDS-PAGE, RP-HPLC, and SEC-HPLC. Cleavage yield is calculated through the following equation:

Cleavage Yield(%)=Mass of Cleaved Target Polypeptide/(Total Mass of Cleaved and Uncleaved target polypeptide in the Supernatant)*100

Analysis of Refolding Yield

An assay is developed to quantify the refolding yield of the target polypeptide yielded from fusion protein aggregate treatment with high hydrostatic pressure. Possible assay techniques would include, but are not limited to, SDS-PAGE, activity assays, and RP-HPLC if the protein of interest contains disulfide bonds. Refolding yield is calculated through the following equation:

Refolding Yield(%)=Mass of Refolded Target Polypeptide/(Total Mass of Target Polypeptide (all forms: including Cleaved, Uncleaved, or Misfolded))*100

REFERENCES

Arnau J, Lauritzen C, Petersen G E, Pedersen J. (2006). "Current strategies for the use of affinity tags and tag removal for the purification of recombinant proteins." *Protein Expression And Purification* 48(1):1-13.

Balny, C. (2002). "High pressure and protein oligomeric dissociation." *High Pressure Research* 22(3-4): 737-741.

Baneyx, F. (1999). "Recombinant protein expression in *Escherichia coli*." *Current Opinion in Biotechnology* 10(5): 411-421.

Bessiere B A, Cottin P, Balny C, Ducastaing A, Bancel F. (1999). "Hydrostatic pressure and calcium-induced dissociation of calpains." *Biochimica Et Biophysica Acta-Protein Structure and Molecular Enzymology* 1430(2):254-261.

Blondel A, Nageotte Ru, Bedouelle H (1996) *Protein Engineering* 9(2): 231-238.

Bowden G A, Paredes A M, Georgiou G. (1991). "Structure and Morphology of Protein Inclusion-Bodies in *Escherichia-Coli*." *Bio-Technology* 9(8):725-730.

Buchner J, Rudolph R. (1991). "Renaturation, Purification and Characterization of Recombinant Fab-Fragments Produced in *Escherichia-Coli*." *Bio*-Technology 9(2):157-162.

Burgess R R, Thompson N E. (2002). "Advances in gentle immunoaffinity chromatography." *Current Opinion in Biotechnology* 13:304-308.

Butt T R, Edavettal S C, Hall J P, Mattern M R. (2005). "SUMO fusion technology for difficult-to-express proteins." *Protein Expression And Purification* 43:1-9.

Carpenter J F, Pikal M J, Chang B S, Randolph T W. (1997). "Rational design of stable lyophilized protein formulations: Some practical advice." *Pharmaceutical Research* 14(8):969-975.

Chaga G, Bochkariov D E, Jokhadze G G, Hopp J, P. N. (1999). "Natural poly-histidine affinity tag for purification of recombinant proteins on cobalt(II)-carboxymethyaspartate crosslinked agarose." *Journal of Chromatography B* 864:247-256.

Chatterjee D K, Esposito D. (2005). "Enhanced soluble protein expression using two new fusion tags." *Protein Expression And Purification* 35:In press.

Chi E Y, Krishnan S, Kendrick B S, Chang B S, Carpenter J F, Randolph T W. (2003). "Roles of conformational stability and colloidal stability in the aggregation of recombinant human granulocyte colony-stimulating factor." *Protein Science* 12(5):903-913.

Clark E D. (2001). "Protein refolding for industrial processes." *Current Opinion in Biotechnology* 12(2):202-207.

Corchero J L, Villayerde A, (1999) *Biotechnol. Bioeng.* 64: 644-649.

Corcheror J L, Cubarsi R, Enfors S-O, Villayerde A (1997) *Biochem. Biophys. Res. Comm.* 237: 325-330.

Corcheror J L, Viaplana E, Benito A., Villayerde A (1996) *J. Biotechnol.* 48: 191-200.

Degraeve, P., P. Delorme, et al. (1996). "Pressure-induced inactivation of *E-coli* beta-galactosidase: Influence of pH and temperature." *Biochimica Et Biophysica Acta-Protein Structure and Molecular Enzymology* 1292(1): 61-68.

Einhauer A, Jungbauer A. (2001). "The FLAG peptide, a versatile fusion tag for the purification of recombinant proteins." *Journal of Biochemistry and Biophysics* 49:455-465.

Foguel, B., M. C. Suarez, et al. (2003). "Dissociation of amyloid fibrils of alpha-synuclein and transthyretin by pressure reveals their reversible nature and the formation of water-excluded cavities." *Proceedings of the National Academy of Sciences of the United States of America* 100 (17): 9831-9836.

Foguel, D., C. R. Robinson, et al. (1999). "Hydrostatic pressure rescues native protein from aggregates." *Biotechnology and Bioengineering* 63(5): 552-558.

Fox J D, Waugh D S. (2003). "Maltose-binding proteins as a solubility enhancer." *Methods in Molecular Biology* 205: 99-117.

Frey, B., S. Franz, et al. (2004). "Hydrostatic pressure induced death of mammalian cells engages pathways related to apoptosis or necrosis." *Cellular and Molecular Biology* 50(4): 459-467.

Fujimoto Y, Ikeuchi H, Tada Y, Oyama H, Oda K, Kunugi S. (2006). "Synergetic effects of pressure and chemical denaturant on protein unfolding: Stability of a serine-type carboxyl protease, kumamolisin." *Biochemica et Biophysica Acta* 1764:364-371.

Furukawa, S, and I. Hayakawa (2000). "Investigation of desirable hydrostatic pressure required to sterilize *Bacillus stearothermophilus* IFO 12550 spores and its sterilization properties in glucose, sodium chloride and ethanol solutions." *Food Research International* 33(10): 901-905.

Gekko K, Hasegawa Y. (1986). "Compressibility Structure Relationship of Globular-Proteins." *Biochemistry* 25(21): 6563-6571.

Gekko K. (2002). "Compressibility gives new insight into protein dynamics and enzyme function." *Biochimica Et Biophysica Acta-Protein Structure and Molecular Enzymology* 1595(1-2):382-386.

Gilbert H F. (1990). "Molecular and Cellular Aspects of Thiol Disulfide Exchange." *Advances in Enzymology and Related Areas of Molecular Biology* 63:69-172.

Gilbert H F. (1995). "Thiol/Disulfide Exchange Equilibria and Disulfide Bond Stability." *Biothiols, Pt A*. p 8-28.

Guise A D, West S M, Chaudhuri J B (1996) *Molecular Biotech.* 6:53-64.

Hage D S. (1999). "Affinity chromatography: a reivew of clinical applications." *Clinical Chemistry* 45:593-513.

Hawley S A. (1971). "Reversible Pressure-Temperature Denaturation of Chymotrypsinogen." *Biochemistry* 10(13):2436-&.

Hendrickx, M., L. Ludikhuyze, et al. (1998). "Effects of high pressure on enzymes related to food quality." *Trends in Food Science & Technology* 9(5): 197-203.

Hesterberg, L. K., M. B. Seefeldt, et al. (2005). "High-Hydrostatic pressure refolding of proteins." *Genetic Engineering News* 25(4): 46-47.

Humphries H E, Christodoulides J E, Heckels J E. (2002). "Expression of the class 1 outer-membrane protein of *Neisseria meningitidis* in *Escherichia coli* and purification using a self-cleavable affinity tag." *Protein Expression And Purification* 26:243-248.

Hunugi S, Fujiwara S, Kidokoro S, Endo K, Hanzawa S. (1999) *FEBS Lett.* 462: 231-235.

Ikeuchi H, Kunugi S, Oda K. (2000). "Activity and stability of a neutral protease from *Vibrio* sp (vimelysin) in a pressure-temperature gradient." *European Journal Of Biochemistry* 267(4):979-983.

Kavoosi M, Meijer J, Kwan E, Creagh A L, Kilburn D G, Haynes C A. (2004). "Inexpensive one-step purifiaction of polypeptides expressed in *Escherichia coli* as fusion with the family 9 carbohydrate-binding module of xylanase 10A from *T. maritima*." *Journal of Chromatography B* 807:87-94.

Kenig M, Peternel V, Gaberc-Porekar V, Menart V. (2005). "Influence of the protein oligomericity on final yield after affinity tag removal of recombinant proteins." *Journal of Chromatography In Press*.

Kitahara R, Yamada H, Akasaka K. (2001). "Two folded conformers of ubiquitin revealed by high-pressure NMR." *Biochemistry* 40(45):13556-13563.

Korn, A., B. Frey, et al. (2004). "High hydrostatic pressure inactivated human tumour cells preserve their immunogenicity." *Cellular and Molecular Biology* 50(4): 469-477.

Kunugi S, Fujiwara S, Kidokoro S, Endo K, Hanzawa S. (1999). "Single-point amino acid substitutions at the 119th residue of thermolysin and their pressure-induced activation." *Febs Letters* 462(3):231-235.

Kunugi, S., Y. Yamazaki, et al. (1999). "Effects of ionic additives and ionic comonomers on the temperature and pressure responsive behavior of thermoresponsive polymers in aqueous solutions." *Langmuir* 15(12): 4056-4061.

Leong L E. (1999). "The use of recombinant fusion proteases in the affinity purification of recombinant proteins." *Molecular Biotechnology* 12:269-274.

Lichty J J, Malecki J L, Agnew H D, D. J. M-H, Tan S. (2005). "Comparison of affinity tags for protein purification." *Protein Expression And Purification* 205:98-105.

Lorentsen R H, Fynbo C H, Thogersen H C, Etzerodt M, Holtet T L. (2005). "Expression, refolding, and purification of recominant human granzyme B." *Protein Expression And Purification* 39:18-26.

Macleod, R. M. and S. A. Hawley (1975). "Pressure-Temperature Stability Of Dna In Neutral Salt-Solutions." *Biopolymers* 15(2): A95-A95.

Mao H. (2004). "A self-cleavable sorase fusion for one-step purification of free recombinant proteins." *Protein Expression And Purification* 37:253-263.

Meyer D E, Trabbic-Carlson K, Chilkoti A. (2001). "Protein purification by fusion with an environmentally responsive elastin-like polypeptide: effect of polypeptide length on the purification of thioredoxin." *Biotechnology Progress* 17:720-728.

Mozhaev, V. V., R. Lange, et al. (1996). "Application of high hydrostatic pressure for increasing activity and stability of enzymes." *Biotechnology and Bioengineering* 52(2): 320-331.

Nallamsetty S, Waugh D S. (2005). "Solubility-enhancing proteins MBP and NusA play a passive role during the folding of their fusion partners." Protein Expression And Purification. Otzen D E, Knudsen B R, Aachmann F, Lambertsen Larsen K, Wimmer R (2002) *Protein Science* 11: 1779-1787.

Paladini A A, Weber G. (1981). "Pressure-Induced Reversible Dissociation of Enolase." *Biochemistry* 20(9):2587-2593.

Pedersen J, Lauritzen C, Madsen P, Dahl S W. (1999). "Removal of N-terminal polyhistidine tags from recombinant proteins using engineered aminopeptidases." *Protein Expression And Purification* 15:389-400.

PhRMA. (2004). "324 Biotechnology Medicines in Testing Promise to Bolster the Arsenal Against Disease." http://www.phrma.org/newmedicines/resources/2004-10-25.145.pdf.

Randolph T W, Seefeldt M, Carpenter J F. (2002). "High hydrostatic pressure as a tool to study protein aggregation and amyloidosis." *Biochimica Et Biophysica Acta-Protein Structure and Molecular Enzymology* 1595(1-2):224-234.

Royer, C. A. (2002). "Revisiting volume changes in pressure-induced protein unfolding." *Biochimica Et Biophysica Acta-Protein Structure and Molecular Enzymology* 1595 (1-2): 201-209.

Sambrook, J., Fritsch, E. F. and Maniatis, T. (1989) "Molecular Cloning: a Laboratory Manual, Second Edition", Cold Spring Harbor, N.Y.

Sasahara, K. and K. Nitta (1999). "Pressure-induced unfolding of lysozyme in aqueous guanidinium chloride solution." *Protein Science* 8(7): 1469-1474.

Schwarcz, W. D., S. P. C. Barroso, et al. (2004). "Virus stability and protein-nucleic acid interaction as studied by high-pressure effects on nodaviruses." *Cellular and Molecular Biology* 50(4): 419-427.

Schwarz E, Lilie H, Rudolph R. (1996). "The effect of molecular chaperones on in vivo and in vitro folding processes." *Biological Chemistry* 377(7-8):411-416.

Seefeldt M B, Kim Y S, Kendrick B S, Tolley K, Carpenter J F, Randolph T W. (2003). "Pressure-induced aggregation of interleukin-1 receptor antagonist (IL-1RA)—Mechanism and thermodynamics." *Abstracts of Papers of the American Chemical Society* 226:U175-U175.

Seefeldt M B, Ouyang J, Froland W A, Carpenter J F, Randolph T W. (2004). "High-pressure refolding of bikunin: Efficacy and thermodynamics." *Protein Science* 13(10): 2639-2650.

Seefeldt, M. B. (2005). "High Pressure Refolding of Protein Aggregates: Efficacy and Thermodynamics." *Department of Chemical and Biological Engineering*. Boulder, University of Colorado—Boulder: 220.

Shih Y P, Kung W M, Chen J C, Yeh C H, Wang A H, T. F. W. (2002) High-throughput screening of soluble recombinant proteins. *Protein Science* 11:1714-1719.

Shih Y P, Wu H C, Hu S M, Wang T F, Wang A H J. (2005) Self-cleavage of fusion protein in vivo using TEV protease to yield native protein. *Protein Science* 14(4):936-941.

Skerra A, Schmidt T G M. (2000). "Use of the Strep-tag and streptavidin for detection and purification of recombinant proteins." *Methods of Enzymology* 326:271-304.

Slootstra J W, Kuperus D, Pluckthun A, Meloen R H. (1997). "Identification of new tag sequences with differential and selective recognition properties for the anti-FLAG monoclonal antibodies M1, M2 and M5." *Molecular Diversity* 2:156-164.

Smeller, L. (2002). "Pressure-temperature phase diagrams of biomolecules." *Biochimica Et Biophysica Acta-Protein Structure and Molecular Enzymology* 1595(1-2): 11-29.

Smith D B, Johnson K S. (1988). "Single-step purification of polypeptides expressed in *Escherichia coli* as fusions with glutathione S-transferase." *Gene* 67:31-40.

Sorensen, H. P. and K. K. Mortensen (2005). "Advanced genetic strategies for recombinant protein expression in *Escherichia coli*." *Journal of Biotechnology* 115(2): 113-128.

St. John R J, Carpenter J F, Randolph T W. (1999). "High pressure fosters protein refolding from aggregates at high concentrations." *Proceedings of the National Academy of Sciences of the United States of America* 96(23): 13029-13033.

St. John, R. J., J. F. Carpenter, et al. (2001). "High pressure refolding of recombinant human growth hormone from insoluble aggregates—Structural transformations, kinetic barriers, and energetics." *Journal of Biological Chemistry* 276(50): 46856-46863.

St. John, R. J., J. F. Carpenter, et al. (2002). "High-pressure refolding of disulfide-cross-linked lysozyme aggregates: Thermodynamics and optimization." *Biotechnology Progress* 18(3): 565-571.

Suwa, K., K. Yamamoto, et al. (1998). "Effects of salt on the temperature and pressure responsive properties of poly(N-vinylisobutyramide) aqueous solutions." *Colloid and Polymer Science* 276(6): 529-533.

Tanaka R, Kosugi M, Mizukami M, Ishibashi H, Tokunaga M. (2004). "Expression and purification of thioredoxin (TrxA) and thioredoxin reductase (TrxB) from *Brevibacillus choshinensis*." *Protein Expression And Purification* 37:385-391.

Tauc, P., C. R. Mateo, et al. (1998). "Pressure effects on the lateral distribution of cholesterol in lipid bilayers: A time-resolved spectroscopy study." *Biopysical Journal* 74(4): 1864-1870.

Tauc, P., C. R. Mateo, et al. (2002). "Investigation of the effect of high hydrostatic pressure on proteins and lipidic membranes by dynamic fluorescence spectroscopy." *Biochimica Et Biophysica Acta-Protein Structure and Molecular Enzymology* 1595(1-2): 103-115.

Terpe K. (2003). "Overview of tag protein fusions: from molecular and biochemical fundamentals to commercial systems." *Applied Microbiology and Biotechnology* 60:523-533.

Timasheff S N. (1993). "The Control of Protein Stability and Association by Weak-Interactions with Water—How Do Solvents Affect These Processes." *Annual Review of Biophysics and Biomolecular Structure* 22:67-97.

Van Opstal, I., S. C. M. Vanmuysen, et al. (2003). "High sucrose concentration protects *E-coli* against high pressure inactivation but not against high pressure sensitization to the lactoperoxidase system." *International Journal of Food Microbiology* 88(1): 1-9.

Wolf E D, Gill R, Geddes S, Pitts J, Wollmer A, Grotzinger J. (1996). "Solution structure of a mini IGF-I." *Protein Science* 5:2193-2202.

The disclosures of all publications, patents, patent applications and published patent applications referred to herein by an identifying citation are hereby incorporated herein by reference in their entirety.

Although the foregoing invention has been described in some detail by way of illustration and example for purposes

What is claimed as new and desired to be protected by Letters Patent of the United States is:

1. A method for producing soluble target polypeptide in samples comprising fusion protein aggregates comprising the steps of:
   a) subjecting a mixture comprising an aqueous solution and/or aqueous suspension comprising protease and fusion protein aggregates to increased hydrostatic pressure compared to atmospheric pressure for a time sufficient for formation of soluble target polypeptide; and,
   b) decreasing the pressure to atmospheric pressure,
wherein said target polypeptides are produced by specific proteolytic cleavage of said target polypeptides from the fusion protein and a portion of the target polypeptide is soluble at atmospheric pressure.

2. The method of claim 1, further comprising a step (c) comprising:
   c) purifying the target polypeptide obtained in step (b).

3. The method of claim 1, wherein in step (a), the increased hydrostatic pressure is from about 500 to about 10000 bar.

4. The method of claim 1, wherein step (b) comprises stepwise pressure reductions.

5. The method of claim 1, wherein step (b) comprises a continuous rate of pressure reduction.

6. The method of claim 1, wherein the pH of the mixture is from about pH 4 to about pH 12.

7. The method of claim 1, wherein step (a) is performed at a temperature from about 0° C. to about 100° C.

8. The method of claim 1, wherein the mixture further comprises a reducing agent.

9. The method of claim 1, wherein the method further comprises addition of a target polypeptide ligand binding partner.

10. The method of claim 1, wherein the mixture further comprises a cleavage buffer.

11. The method of claim 10, wherein the cleavage buffer further comprises one or more additional agents selected from the group consisting of one or more stabilizing agents, one or more buffering agents, one or more surfactants, one or more disulfide shuffling agent pairs, one or more chaotropic agents, one or more salts, and combinations of two or more of the foregoing.

12. The method of claim 11, wherein the one or more additional agents is one or more stabilizing agents.

13. The method of claim 11, wherein the one or more additional agents is one or more surfactants.

14. The method of claim 11, wherein the one or more additional agents is one or more buffering agents.

15. The method of claim 11, wherein the one or more additional agent is one or more chaotropic agents.

16. The method of claim 11, wherein the one or more additional agents are one or more disulfide shuffling agent pair.

17. The method of claim 1, wherein the time in step (a) is from about 15 minutes to about 50 hours.

18. The method of claim 1, wherein the fusion partner is selected from the group consisting of his-tags, maltose-binding protein, thioredoxin, glutathione-s-transferase, DsbA, gphD, FLAG, calmodulin binding protein, streptag II, HA-tag, Softag1, Softag 3, c-myc, T7-tag, S-tag, NusA, chitin-binding domain, xylanase 10A, tobacco etch virus, and ubiquitin.

19. The method of claim 1, wherein the protease is a serine, cysteine or metalloprotease.

20. The method of claim 1, wherein the fusion protein comprises the protease.

21. The method of claim 1, wherein the total concentration of fusion protein in the fusion protein aggregate is from about 0.01 mg/mL to about 500 mg/mL.

22. The method of claim 1, wherein step (a) further comprises agitation of the mixture.

23. The method of claim 1, wherein the method does not include one or more chaotropic agents.

24. The method of claim 1, further comprising performing solution exchange.

* * * * *